US010984891B2

(12) United States Patent
Fu et al.

(10) Patent No.: US 10,984,891 B2
(45) Date of Patent: Apr. 20, 2021

(54) METHODS FOR GLOBAL RNA-CHROMATIN INTERACTOME DISCOVERY

(71) Applicant: The Regents of the University of California, Oakland, CA (US)

(72) Inventors: Xiang-Dong Fu, La Jolla, CA (US); Bing Zhou, La Jolla, CA (US); Xiao Li, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 273 days.

(21) Appl. No.: 15/669,113

(22) Filed: Aug. 4, 2017

(65) Prior Publication Data

US 2018/0039729 A1 Feb. 8, 2018

Related U.S. Application Data

(60) Provisional application No. 62/371,429, filed on Aug. 5, 2016.

(51) Int. Cl.
*C12Q 1/6874* (2018.01)
*C40B 20/00* (2006.01)
*G16Z 99/00* (2019.01)
*G16B 30/00* (2019.01)
*C12Q 1/6816* (2018.01)

(52) U.S. Cl.
CPC ........... *G16B 30/00* (2019.02); *C12Q 1/6816* (2013.01); *C12Q 1/6874* (2013.01)

(58) Field of Classification Search
CPC .................................. G06F 19/22; C12Q 1/68
See application file for complete search history.

(56) References Cited

U.S. PATENT DOCUMENTS

| | | | |
|---|---|---|---|
| 7,601,492 B2 * | 10/2009 | Fu | B82Y 5/00 435/6.12 |
| 2015/0056615 A1 * | 2/2015 | Kingston | C12Q 1/6809 435/6.11 |
| 2017/0362649 A1 * | 12/2017 | Lieberman-Aiden | C40B 30/04 |

OTHER PUBLICATIONS

Li et al., Molecular Mechanisms of Long Noncoding RNAs on Gastric Cancer, Oncotarget, 2016, 7(8), 8601-8612. (Year: 2016).*
Morgan et al., MmeI: A Minimal Type II Restriction-Modification System That Only Modifies One DNA Strand for Host Protection, Nucleic Acids Research, 2008, 36(20), 6558-6570. (Year: 2008).*
Servant et al., HiC-Pro: An Optimized and Flexible Pipeline for Hi-C Data Processing, Genome Biology, 2015, 16(259), 1-11. (Year: 2015).*
Wang et al., Characterization of Denaturation and Renaturation of DNA for DNA Hybridization, Environmental Health and Toxicology, 2014, 29, Article e2014007, 1-8. (Year: 2014).*
Cusanovich et al., Multiplex Single-Cell Profiling of Chromatin Accessibility by Combinatorial Cellular Indexing, Epigenetics, 2015, 348(6237), 910-914. (Year: 2015).*
Minoche et al., Evaluation of High-Throughput Sequencing Data Generated on Illumina HiSeq and Genome Analyzer Systems, Genome Biology, 2011, 12(8112), 1-15. (Year: 2011).*

* cited by examiner

*Primary Examiner* — Amy M Bunker
(74) *Attorney, Agent, or Firm* — Gavrilovich, Dodd & Lindsey LLP

(57) ABSTRACT

A method to detect chromatin-interacting RNAs in any given state of a cell or tissue by examining global RNA interactions with DNA by deep sequencing. A method to generate a global view of chromatin-RNA interactome by mapping the binding locations on the genome of each detected chromatin interacting RNA.

18 Claims, 39 Drawing Sheets

Specification includes a Sequence Listing.

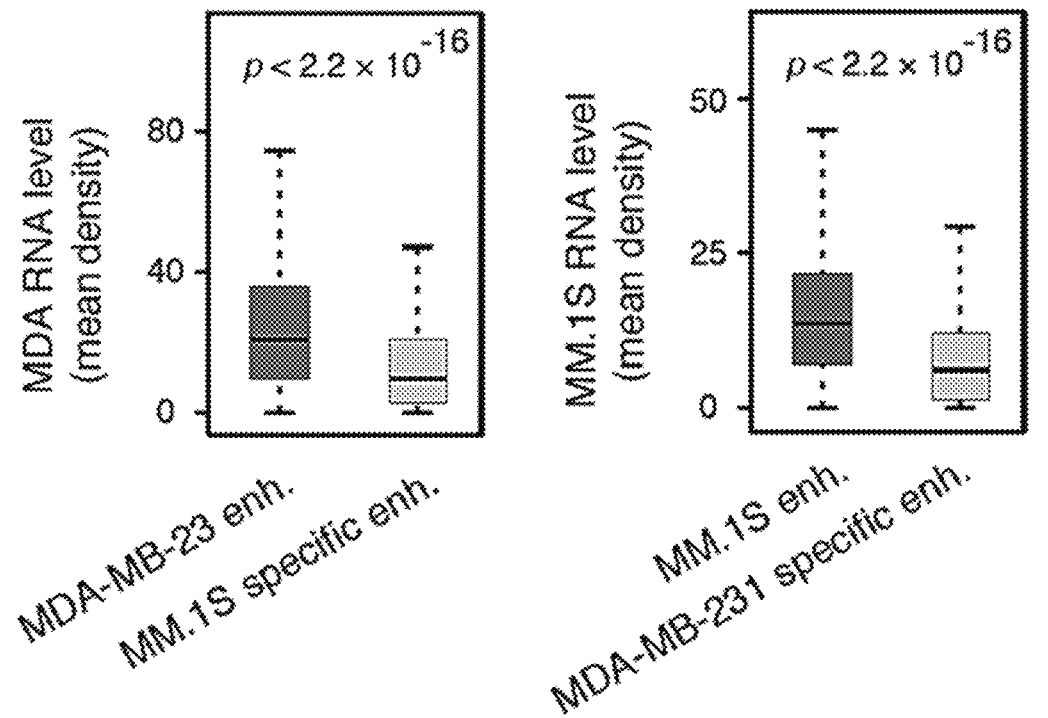
FIG. 12E
FIG. 12F
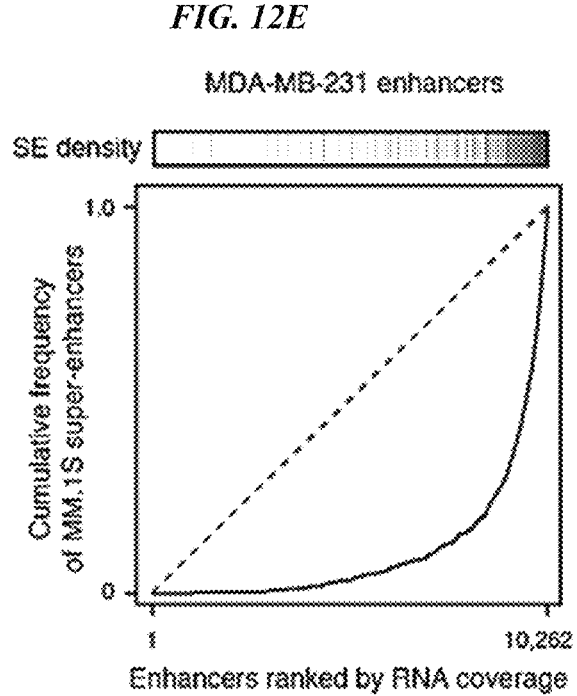
FIG. 12G
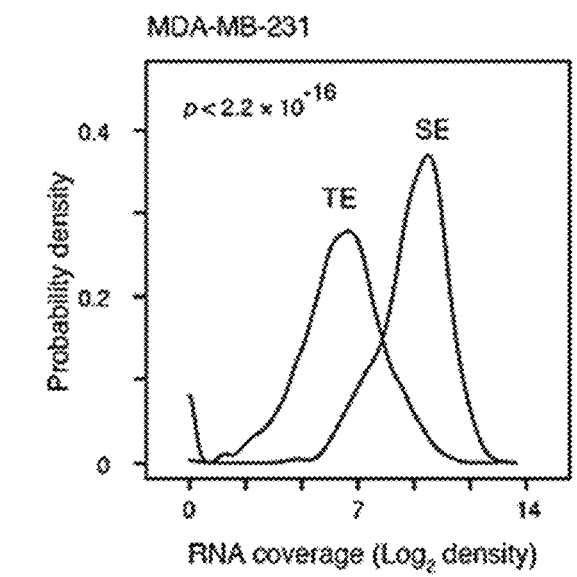
FIG. 12H

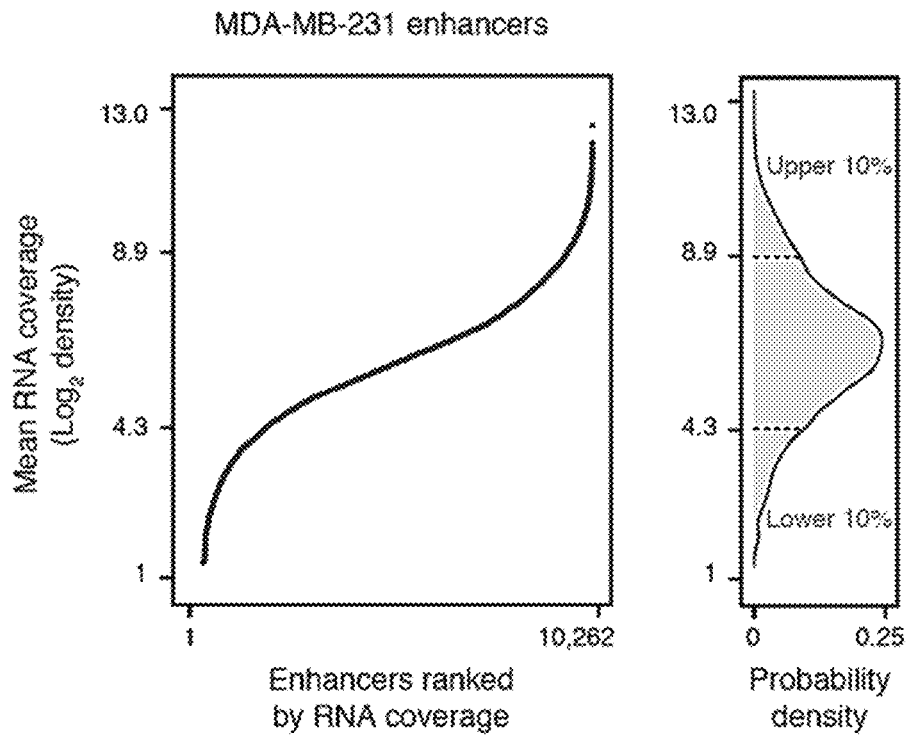
FIG. 12I
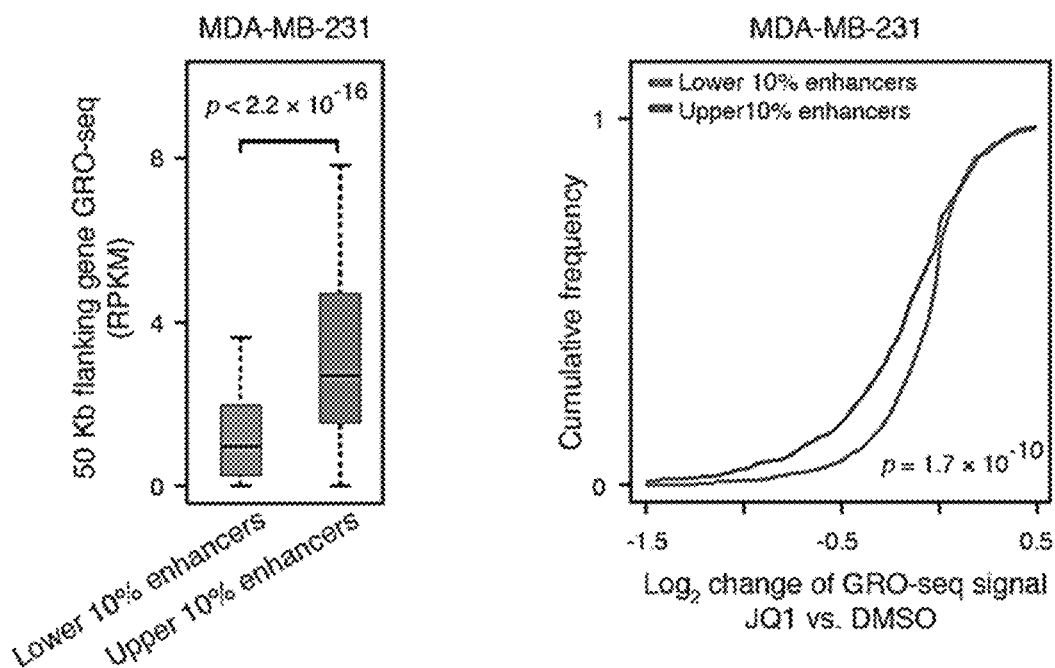
FIG. 12J
FIG. 12K

METHODS FOR GLOBAL RNA-CHROMATIN INTERACTOME DISCOVERY

CROSS REFERENCE TO RELATED APPLICATIONS

This application claims priority under 35 U.S.C. § 119 from Provisional Application Ser. No. 62/371,429, filed Aug. 5, 2016, the disclosure of which is incorporated herein by reference.

STATEMENT OF GOVERNMENT SUPPORT

This invention was made with government support under Grant Nos. DK098808, GM049369, HG004659, and HG007005 awarded by the National Institutes of Health. The government has certain rights in the invention.

TECHNICAL FIELD

The disclosure provides methods that detect chromatin-interacting RNAs in any given state of a cell or tissue by examining global RNA interactions with DNA by deep sequencing. The disclosure further provides methods to generate a global view of the chromatin-RNA interactome by mapping the binding locations on the genome of each detected chromatin interacting RNA.

BACKGROUND

Decades of genomic research reveal that mammalian genomes are more prevalently transcribed than previously anticipated. It is now quite clear that mammalian genomes express not only protein-coding RNAs but also a large repertoire of non-coding RNAs that have regulatory functions in different layers of gene expression. Many of those regulatory RNAs appear to directly act on chromatin, as exemplified by various long non-coding RNAs (lncRNAs). Some of those regulatory RNAs mediate genomic interactions only in cis, while others, such as MALAT1 and NEAT1, are capable of acting in trans.

SUMMARY

High eukaryotic genomes are populated with enhancers, but it has been a major challenge in defining specific enhancer-promoter relationship. Enhancers can also be divided into typical and super-enhancers, yet their functional distinctions remain to be understood. Described herein are methods to capture in situ Global RNA Interactions with DNA by deep sequencing (GRID-seq).

It was unexpectedly found that the methods of the disclosure were able to detect a highly selective set of RNAs (including both lncRNAs and protein-coding pre-mRNAs) decorated on enhancers, particularly super-enhancers. Based on the origins of these RNAs and functional perturbation of enhancer activities, the methods disclosed herein allow for deducing global enhancer-promoter connectivity, which is significantly beyond the traditional framework. Thus, the methods of disclosure provide for deducing the functional RNA-chromatin interactome in the 3D genome.

The disclosure provides a method to determine global RNA Interactions with DNA, comprising (1) ligating a bivalent linker to RNA crosslinked with genomic DNA and protein (RNA-DNA-protein) obtained from nuclei of a cell, wherein the bivalent linker comprises a stretch of double stranded DNA (dsDNA), a stretch of single stranded RNA (ssRNA), one or more recognition sites for restriction enzymes, one or more capture moieties, and one or more barcode sequences; (2) extending the bivalent linker with a reverse transcriptase into the ligated RNA region; (3) ligating the bivalent linker to genomic DNA to form a dsDNA capture probe comprising the bivalent linker paired with the RNA-DNA-protein; (4) reversing the crosslinking of the dsDNA capture probe; (5) purifying the dsDNA capture probe by using a capture agent that is bound to a solid support that binds with the one or more capture moieties; (6) denaturing the dsDNA capture probe to form two single stranded DNA products, wherein one single stranded product remains attached to the capture agent while the second single stranded DNA product is in solution; (7) converting the second single stranded DNA product into a double stranded DNA product using a polymerase; (8) cutting the double stranded DNA product using restriction enzymes that recognize the one or more recognition sites of the bivalent linker; (9) isolating double stranded DNA products that comprises an RNA-related segment and a genomic DNA-related segment; (10) attaching an adapter to the isolated double stranded DNA products and deep sequencing the isolated double stranded DNA products to generate raw sequencing reads; (11) sorting the one or more raw sequencing reads using the one or more barcode sequences to form library of sequencing reads; and (12) aligning and mapping the library of sequencing reads to determine global RNA Interactions with DNA, wherein the method determines both protein-coding RNAs and non-coding RNAs interactions with DNA.

In a particular embodiment, the disclosure provides a method to determine global RNA Interactions with DNA, comprising: (1) fixing cells with one or more fixative agents; (2) isolating nuclei from the fixed cells, wherein the nuclei comprise genomic DNA and RNA; (3) digesting the genomic DNA of the nuclei with one or more restriction enzymes; (4) ligating a bivalent linker to the RNA of the nuclei, wherein the bivalent linker comprises a stretch of double stranded DNA (dsDNA), a stretch of single stranded RNA (ssRNA), one or more recognition sites for restriction enzymes, one or more capture moieties, and one or more barcode sequences; (5) extending the bivalent linker with a reverse transcriptase into the ligated RNA region; (6) ligating the bivalent linker to genomic DNA of the nuclei thus creating a dsDNA capture probe; (7) purifying the dsDNA capture probe using a capture agent that is bound to a solid support that binds with the one or more capture moieties; (8) denaturing dsDNA capture probe that is attached to the capture agent to form two single stranded DNA products, wherein one single stranded product remains attached to the capture agent while the second single stranded DNA product is in solution; (9) converting the second single stranded DNA product into a double stranded DNA product using a polymerase; (10) cutting the double stranded DNA product using restriction enzymes that recognize the one or more recognition sites of the bivalent linker; (11) isolating double stranded DNA products that comprise RNA-related and genomic DNA-related segments obtained from the nuclei; (12) attaching an adapter to the isolated double stranded DNA products and deep sequencing the isolated double stranded DNA products to generate raw sequencing reads; (13) sorting the one or more raw sequencing reads using the one or more barcode sequences to form library of sequencing reads; and (14) aligning and mapping the library of sequencing reads to determine global RNA Interactions with DNA, wherein the method determines both protein-coding RNAs and non-coding RNAs interactions with DNA. In a further embodiment steps (1)-(6) are performed in situ. In yet a further embodiment, steps (7)-(12) are performed in vitro. In another embodiment, a method disclosed herein comprise fixing cells with one or more fixative agents are selected from the group consisting of disuccinimidyl glutarate, formaldehyde, glutaraldehyde, acrolein, glyoxal, carbodiimides, osmium tetroxide, diimidoesters, choro-s-triazides, mercuric chloride, ethanol, methanol, and acetone. In a certain embodiment, cells are doubly fixed with formaldehyde and disuccinimidyl glutarate. In yet another embodiment, a method disclosed herein comprises digesting genomic DNA of nuclei with one or more restriction enzymes selected from the group consisting of AciI, AluI, BfaI, BfuCI, BstUI, CviAII, CviKI-1, CviQI, DpnI, DpnII, FatI, HaeIII, HhaI, HinP1I, HpaII, HpyCH4IV, HpyCH4V, LpnPI, MboI, MluCI, MnlI, MseI, MspI, MspJI, NlaIII, PhoI, RsaI, Sau3AI, TaqαI, Tsp509I, AccII, AfaI, AluBI, AoxI, AspLEI, BscFI, Bsh1236I, BshFI, BshI, BsiSI, BsnI, Bsp143I, BspACI, BspANI, BspFNI, BssMI, BstENII, BstFNI, BstHHI, BstKTI, BstMBI, BsuRI, CfoI, Csp6I, CviJI, CviRI, CviTI, FaeI, FaiI, FnuDII, FspBI, GlaI, HapII, Hin1II, R9526, Hin6I, HpySE526I, Hsp92II, HspAI, Kzo9I, MaeI, MaeII, MalI, MvnI, NdeII, PalI, RsaNI, SaqAI, SetI, SgeI, SgrTI, Sse9I, SsiI, Sth132I, TaiI, TaqI, TasI, ThaI, Tru1I, Tru9I, TscI, TspEI, TthHB8I, and XspI. a method disclosed herein comprises digesting genomic DNA of nuclei with AluI.

In yet a further embodiment, a method disclosed herein comprises a bivalent linker which comprises two strands, a top strand and bottom strand, wherein the top strand comprises DNA and the 5' end of the top strand is phosphorylated, wherein the bottom strand comprises a stretch of RNA and a stretch of DNA, wherein the stretch of RNA is found at the 5' end of the bottom strand and is pre-adenylated. In a further embodiment, the bottom strand comprises a DNA nucleotide that is conjugated to a capture moiety. In yet a further embodiment, the capture moiety is a biotin residue and the capture agent bound to a solid support is streptavidin beads. In another embodiment, the stretch of RNA of the bivalent linker comprises a bar code sequence. In further embodiment, the bar code sequence is from 3 to 8 base pairs in length.

In a certain embodiment, the disclosure provides for a method comprising denaturing a bivalent linker that is ligated to nuclei which is bound to the capture agent by the addition of a denaturant. In a further embodiment, the denaturant is sodium hydroxide.

In another embodiment, the disclosure also provides for a method comprising cutting a double stranded DNA product with MmeI.

In yet another embodiment, the disclosure also provides for a method comprising isolating a double stranded DNA product comprising RNA and genomic DNA from the nuclei by using a native gel.

In a certain embodiment, the disclosure also provides for use of human cells in a method disclosed herein.

In another embodiment, the disclosure provides for the generation of >200 million 100 nucleotide raw sequencing reads using a method disclosed herein. In a further embodiment, a method disclosed herein generates ~40 million uniquely mapped read mates. In yet a further embodiment, raw sequencing reads are sorted, mapped and visualized with Cytoscape using a self-organized layout.

In a particular embodiment, the disclosure further provides for a method that can determine trans-chromosomal interactions by subtracting out a background generated from a method disclosed herein utilizing pre-mRNAs of protein-coding genes, wherein signals above the background reflect RNAs that engage in trans-chromosomal interactions or engage with chromatin in spatial proximity to their sites of transcription. In a further embodiment, the identifies RNAs that interact with enhancers and/or super enhancers.

In a certain embodiment, the disclosure provides for a method disclosed herein which detects and discovers molecular markers associated with a disease or disorder.

DESCRIPTION OF DRAWINGS

FIG. 12A-K shows RNA-chromatin interactions on cell type-specific enhancers. Scatter plots of background (A) and foreground (B) GRIP-seq signals between MDA-MD-231 and MM.1S cells in the 1 Kb-binned human genome. (C) and (D) Violin plots showing co-enrichment of specific RNA-chromatin interactions and key chromatin marks in MDA-MB-231 cells (C) and MM.1S (D). Left: Enrichment of mean chromatin interaction signals of hit RNAs relative to ChIP-seq peaks of RNA Pol II, H3K4me3, H3K27ac and H3K27me3 (all based on the published ChIP-seq data, methods presented herein). Right: Background signals. Bars represent the range from 25 to 75 percentile. (E) and (F) Quantification of mean hit RNA densities on enhancers in the same cell type (left bars) relative to specific enhancers in a different cell type (right bars). (G) Superenhancers relative to RNA-chromatin interactions signals detected by GRID-seq. Enhancers in MDA-MD-231 cells were defined based on the mapped H3K27ac signals (from the data in GSM1204474 and GSM1204475). Each bar on top represents a super-enhancer. Curved line: The cumulative curve of rank-ordered RNA-chromatin interactions; Grey dashed line: Random distribution. (H) Probability density map of hit RNA coverage on super-enhancers (SE) versus typical enhancers (TE). (I) Left: Rank-ordered RNA-chromatin interaction levels on all active enhancers. Right: Upper (SE enriched) and lower (TE enriched) 10 percentiles of enhancers selected for functional analysis. (J) Expression of genes associated with top 10% RNA-interacting enhancers (right box) relative to those associated with bottom 10% RNA-interacting enhancers (left box), both within the ±50 Kb range based on the GRO-seq assay performed on the same cell type. (K) Fold changes in GRO-seq plotted in the accumulative fashion for the two groups of genes as defined in (C) in response to functional perturbation of enhancers on MDAMD-231 cells by using the BRD4 inhibitor JQ1. Statistical significance of comparison is estimated by t-test in panel (H), (J) and (K).

DETAILED DESCRIPTION

Figure 1A:
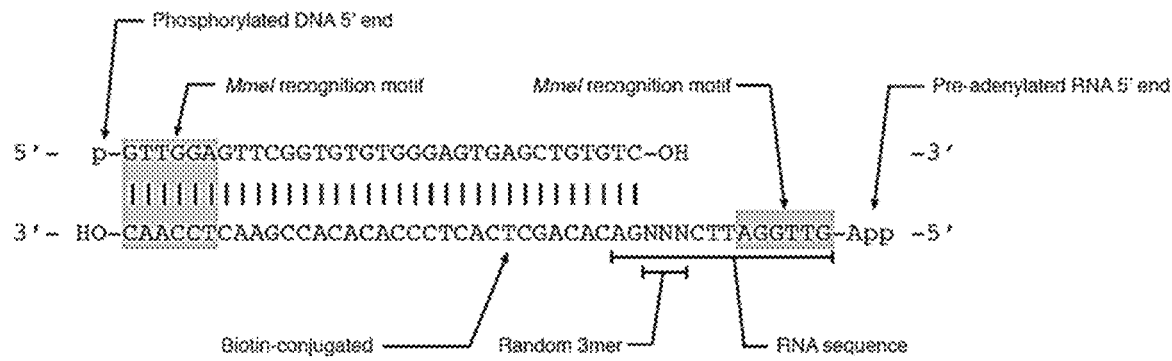
FIG. 1A-C provides an example of a GRID-seq linker design and demonstrates the reproducibility of RNA capture. (A) An embodiment of a design for a bivalent linker for GRID-seq. The top strand is a 5' phosphorylated DNA sequence (black) (SEQ ID NO:1) and the bottom strand comprises both DNA and RNA bases with a biotinylated T residue in the middle (SEQ ID NO:2). Randomized bases (N) could serve as barcodes for filtering PCR duplicates generated during library amplification and both ends of the linker also carry the MmeI restriction site (grey-shaded). The linker is pre-adenylated for ligation to RNA in the absence of ATP. (B) and (C) Reproducibility of RNAs captured by GRID-seq. RNA reads corresponding to individual annotated genes were plotted to compare between the biological replicates of human MDA-MB-231 cells (B) or *Drosophila* S2 cells (C).

As used herein and in the appended claims, the singular forms "a," "an," and "the" include plural referents unless the context clearly dictates otherwise. Thus, for example, reference to "a biomarker" includes a plurality of such biomarkers and reference to "the metabolic feature" includes reference to one or more metabolic features and equivalents thereof known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although many methods and reagents are similar or equivalent to those described herein, the exemplary methods and materials are disclosed herein.

All publications mentioned herein are incorporated by reference in full for the purpose of describing and disclosing methodologies that might be used in connection with the description herein. Moreover, with respect to any term that is presented in one or more publications that is similar to, or identical with, a term that has been expressly defined in this disclosure, the definition of the term as expressly provided in this disclosure will control in all respects.

Mammalian genomes express not only protein-coding RNAs but also a large repertoire of non-coding RNAs that have regulatory functions in different layers of gene expression. Many of those regulatory RNAs appear to directly act on chromatin, as exemplified by various lncRNAs. Some of those regulatory RNAs mediate genomic interactions only in cis, while others, such MALAT1 and NEAT1, are capable of acting in trans. These findings suggest an emerging paradigm in regulated gene expression via specific RNA-chromatin interactions.

Various techniques have been developed to localize specific RNAs on chromatin. These methods, such as Chromatin Isolation by RNA Purification (ChIRP), Capture Hybridization Analysis of RNA Targets (CHART), and RNA Affinity Purification (RAP), all rely on using complementary sequences to capture a specific RNA followed by deep sequencing to identify targets on chromatin. Importantly, all of these methods only allow analysis of one known RNA at a time, and up to date, a global view is lacking on all RNA-chromatin interactions, which is critical to address a wide range of functional genomics questions.

One of the most pressing questions is which enhancers interact with individual gene promoters to regulate gene expression. Current approaches to this problem rely on long distance DNA-DNA interactions detected by Hi-C or ChIA-PET coupled with immunoprecipitation of RNA polymerase II (RNA Pol II) and DNA-DNA interaction mediators. However, such interactions are often embedded in numerous static physical interactions confined within largely cell type-independent topologically associating domains (TADs), which would thus impede accurate assignment. Another pressing question concerns the newly introduced concept of super-enhancers. As super-enhancers may be argued as a set of stitched typical enhancers, it has been unclear whether super-enhancers are indeed superior over typical enhancers in action range, potency or both in activating promoters.

To fill these important gaps, a general approach for systematic localization of all potential chromatin-interacting RNAs in an unbiased fashion was developed. Presented herein are methods that allow for mapping Global RNA Interactions with DNA by deep sequencing (GRID-seq) via using a bivalent linker to ligate RNA to DNA in situ. In a particular embodiment, a method disclosed herein utilizes a bivalent linker comprising a stretch of single stranded RNA and a stretch of double stranded DNA that allows for capturing the physical proximity of chromatin-interacting RNAs. The single stranded RNA stretch of the bivalent liner can be ligated by RNA ligase with endogenous RNAs found in the cell nucleus. The double stranded DNA portion of the bivalent linker can be ligated to nearby chromatin thus forming a covalently connected molecule for deep sequencing. Thus, the GRID-seq methods disclosed herein can detect all chromatin-interacting RNAs (both protein-coding RNAs and non-coding RNAs) in any given cell state or type of tissue. By implementing in situ ligation, chromatin-RNA interactions can be preserved in their original state with minimal disruption.

While techniques have been developed to localize specific RNAs on chromatin. These methods, such as Chromatin Isolation by RNA Purification or ChIRP, Capture Hybridization Analysis of RNA Targets or CHART, and RNA Affinity Purification or RAP, all rely on using complementary sequences to capture a specific RNA followed by deep sequencing to identify targets on chromatin. Importantly, all of these methods only allow analysis of one known RNA at a time, and up to date, a global view is lacking on all RNA-chromatin interactions, which is important to address a wide range of functional genomics questions. In contrast to ChIRP, CHART, RAP, etc., the GRID-seq methods disclosed herein use a bivalent linker to ligate RNA to DNA in situ and present an unbiased global picture on RNA-chromatin interactions. Thus, the methods disclosed herein provide a global picture on RNA-chromatin interactions, exposing distinct classes of cis- and trans-acting RNAs in one or more subject genomes. For example, the methods presented herein allowed for elucidation of global RNA-chromatin interactions in both human and *Drosophila* genomes. The data presented herein, revealed a large set of both coding and non-coding RNAs that are prevalently associated with enhancers, particularly super-enhancers, which allow for deducing enhancer-promoter connectivity in 3D genomes.

The methods of the disclosure can be used to detect which RNAs are capable of engaging in trans-chromosomal interactions in a genome. In the studies presented herein it was found that relatively few RNAs were capable of engaging in trans-chromosomal interactions in the human genome, MALAT1 and NEAT1 being the major lncRNAs. However, unlike human cells, a large number of small nucleolar RNAs (snoRNAs) appear to participate in chromatin interactions in *Drosophila* S2 cells, raising an intriguing possibility that various snoRNAs may have important roles at the chromatin levels in *Drosophila*. The identification of many unannotated chromatin-interacting transcripts provides rich resources for future functional studies.

Besides trans-chromosomal chromatin-interacting RNAs, a large set of chromatin-interacting RNAs were detected using the methods disclosed herein, many of which were not from the most highly expressed genes in the cell. Further, it was found using the methods disclosed herein that many of these RNAs are able to reach out to chromatin that are megabases away in linear DNA distance, and in some extreme cases, specific RNAs can decorate the entire chromosome arm or the full chromosome, which has only one precedent XIST in human and one precedent roX1/2 in *Drosophila* cells, both of which are involved in X-chromosome dosage compensation. The findings presented herein beg yet another intriguing question as to whether some RNAs are involved in dosage compensation or involved in other large-scale regulatory activities in autosomes. Accordingly, the methods presented herein provide an unbiased global detection and analysis of RNA-chromatin interactions. The methods of the disclosure are powerful tools for studying regulatory RNAs on chromatin.

In a particular embodiment, a GRID-seq method disclosed herein comprises a step of fixing cells with one or more fixative agents so as to stabilize RNAs on chromatin. As used herein, "fixative" or "cross-linker" can generally refer to an agent that can fix or cross-link cells. Fixed or cross-linking cells can stabilize protein-nucleic acid complexes in the cell. Suitable fixatives and cross-linkers can include, formaldehyde, glutaraldehyde, ethanol-based fixatives, methanol-based fixatives, acetone, acetic acid, osmium tetraoxide, potassium dichromate, chromic acid, potassium permanganate, mercurials, picrates, formalin, paraformaldehyde, amine-reactive NHS-ester crosslinkers such as bis[sulfosuccinimidyl] suberate (BS3), 3,3'-dithiobis[sulfosuccinimidylpropionate] (DTSSP), ethylene glycol bis [sulfosuccinimidylsuccinate (sulfo-EGS), disuccinimidyl glutarate (DSG), disuccinimidyl suberate, dithiobis[succinimidyl propionate] (DSP), disuccinimidyl subcrate (DSS), ethylene glycol bis[succinimidylsuccinate] (EGS), NHS-ester/diazirine crosslinkers such as NHS-diazirine, NHS-LC-diazirine, NHS-SS-diazirine, sulfo-NHS-diazirine, sulfo-NHS-LC-diazirine, acrolein, glyoxal, carbodiimides, diimidoesters, choro-s-triazides, mercuric chloride, and sulfo-NHS-SS-diazirine. In a further embodiment, a GRID-seq method disclosed herein comprises fixing cells with formaldehyde. In an alternate embodiment, a GRID-seq method disclosed herein comprises fixing cells with disuccinimidyl glutarate. In yet another alternate embodiment, a GRID-seq method disclosed herein comprises fixing cells with formaldehyde and disuccinimidyl glutarate.

The cells can be obtained from any number of sources or samples. Samples comprising cells containing target nucleic acids can be obtained from a subject by any number of means, including by taking bodily fluids (e.g., blood, urine, serum, lymph, saliva, anal and vaginal secretions, perspiration and semen), taking tissue, or by collecting cells/organisms. The sample may be from a mammal, non-mammal or environmental sample comprising prokaryotic or eukaryotic organisms. The sample obtained may be comprised of a single type of cell/organism, or may be comprised multiple types of cells/organisms.

In a certain embodiment, a GRID-seq method disclosed herein comprises a step of isolating nuclei from fixed cells. Suitable methods to isolate nuclei from fixed cells include those taught herein, and those described in Kihlmark et al. (Preparation of Nuclei and Nuclear Envelopes, *Cell Biology: A Laboratory Handbook*, Vol. 2, Celis, J. E. (Ed.) pp. 152-158 (Academic Press, San Diego, 1998); Marzluff et al. (Transcription of RNA in Isolated Nuclei, *Transcription and Translation: A Practical Approach*, Hames, B. D. and Higgens, S. J. (Eds.) pp. 89-129 (IRL Press, Oxford, UK 1984)); Greenberg et al. (Identification of Newly Transcribed RNA, in Current Protocols in Molecular Biology, Ausbel, F. M., et al. (Eds.) pp. 4.10.1-4.10.11 (John Wiley and Sons, New York, 1997). In a particular embodiment, the nuclei isolated from fixed cells comprises intact nucleic acids, including DNA, RNA, proteins and/or various small nucleotide/nucleoside species.

In a further embodiment, a GRID-seq method disclosed herein comprises a step of fragmenting nucleic acids. Fragmentation can be accomplished using established methods for fragmenting chromatin, including, for example, sonication, shearing and/or the use of restriction enzymes. The restriction enzyme can have a restriction site of 1, 2, 3, 4, 5, or 6 bases long. Examples of restriction enzymes include but are not limited to AatII, Acc65I, AccI, AciI, AclI, AcuI, AfeI, AflII, AflII, AflIII, AgeI, AhdI, AleI, AluI, AlwI, AlwNI, ApaI, ApaLI, ApeKI, ApoI, AscI, AseI, AsiSI, AvaI, AvaII, AvrII, BaeGI, BaeI, BamHI, BanI, BanII, BbsI, BbvCI, BbvI, BccI, BceAI, BcgI, BciVI, BclI, BfaI, BfuAI, BfuCI, BglI, BglII, BlpI, BmgBI, BmrI, BmtI, BpmI, Bpu10I, BpuEI, BsaAI, BsaBI, BsaHI, BsaI, BsaJI, BsaWI, BsaXI, BscRI, BscYI, BsgI, BsiEI, BsiHKAI, BsiWI, BslI, BsmAI, BsmBI, BsmFI, BsmI, BsoBI, Bsp1286I, BspCNI, BspDI, BspEI, BspHI, BspMI, BspQI, BsrBI, BsrDI, BsrFI, BsrGI, BsrI, BssHII, BssKI, BssSI, BstAPI, BstBI, BstEII, BstNI, BstUI, BstXI, BstYI, BstZ17I, Bsu36I, BtgI, BtgZI, BtsCI, BtsI, Cac8I, ClaI, CspCI, CviAII, CviKI-1, CviQI, DdcI, DpnI, DpnII, DraI, DraIII, DrdI, EacI, EagI, EarI, EciI, Eco53kI, EcoNI, EcoO109I, EcoP15I, EcoRI, EcoRV, FatI, FauI, Fnu4HI, FokI, FseI, FspI, HaeII, HaeIII, HgaI, HhaI, HincII, HindIII, HinfI, HinP1I, HpaI, HpaII, HphI, Hpy166II, Hpy188I, Hpy188III, Hpy99I, HpyAV, HpyCH4III, HpyCH4IV, HpyCH4V, KasI, KpnI, MboI, MboII, MfeI, MluI, MiyI, MmeI, MnlI, MscI, MseI, MslI, MspA1I, MspI, MwoI, NaeI, NarI, Nb.BbvCI, Nb.BsmI, Nb.BsrDI, Nb.BtsI, NciI, NcoI, NdeI, NgoMIV, NheI, NlaIII, NlaIV, NmeAIII, NotI, NruI, NsiI, NspI, Nt.AlwI, Nt.BbvCI, Nt.BsmAI, Nt.BspQI, Nt.BstNBI, Nt.CviPII, PacI, PaeR7I, PciI, PflFI, PflMI, PhoI, PleI, PmeI, PmlI, PpuMI, PshAI, PsiI, PspGI, PspOMI, PspXI, PstI, PvuI, PvuII, RsaI, RsrII, SacI, SacII, SalI, SapI, Sau3AI, Sau96I, SbfI, ScaI, ScrFI, SexAI, SfaNI, SfcI, SfiI, SfoI, SgrAI, SmaI, SmlI, SnaBI, SpeI, SphI, SspI, StuI, StyD4I, StyI, SwaI, T, TaqαI, TfiI, TliI, TseI, Tsp45I, Tsp509I, TspMI, TspRI, Tth111I, XbaI, XcmI, XhoI, XmaI, XmnI, and ZraI. The resulting fragments can vary in size. The resulting fragments may also comprise a single-stranded overhand at the 5' or 3' end. In one embodiment, the method comprises incubating isolated nuclei with one or more restriction enzymes so as to digest DNA in situ. In a particular embodiment, the isolated nuclei are incubated with one or more frequent cutting restriction enzymes, e.g., a 4-bp cutter. Examples of such restriction enzymes, include but are not limited to, AciI, AluI, BfaI, BfuCI, BstUI, CviAII, CviKI-1, CviQI, DpnI, DpnII, FatI, HaeIII, HhaI, HinP1I, HpaII, HpyCH4IV, HpyCH4V, LpnPI, MboI, MluCI, MnlI, MseI, MspI, MspJI, NlaIII, PhoI, RsaI, Sau3AI, TaqαI, Tsp509I, AccII, AfaI, AluBI, AoxI, AspLEI, BscFI, Bsh1236I, BshFI, BshI, BsiSI, BsnI, Bsp143I, BspACI, BspANI, BspFNI, BssMI, BstENII, BstFNI, BstHHI, BstKTI, BstMBI, BsuRI, CfoI, Csp6I, CviJI, CviRI, CviTI, FaeI, FaiI, FnuDII, FspBI, GlaI, HapII, Hin1II, R9529, Hin6I, HpySE526I, Hsp92II, HspAI, Kzo9I, MaeI, MaeII, MalI, MvnI, NdeII, PalI, RsaNI, SaqAI, SetI, SgeI, SgrTI, Sse9I, SsiI, Sth132I, TaiI, TaqI, TasI, ThaI, TruII, Tru9I, TscI, TspEI, TthHB8I, and XspI.

In a particular embodiment, isolated nuclei are incubated and cut with AluI. It should be noted that restriction enzymes cut dsDNA so as to leave blunt or sticky ends. In the case of the latter, the sticky ends can be filled in or removed by blunting. Blunting is the elimination of incompatible 3' or 5' overhangs for the promotion of blunt-end ligation. Several approaches may be used for DNA end blunting. Terminal unpaired nucleotides may be removed from DNA ends by using an enzyme with exonuclease activity, which hydrolyzes a terminal phosphodiester bond, thereby removing the overhang one base at a time. DNA fragments with 5' overhangs may be blunted by filling in a recessed 3' terminus with DNA polymerase in the presence of dNTPs. End removal or fill-in can be accomplished using a number of enzymes, including DNA Polymerase I Large (Klenow) Fragment, T4 DNA Polymerase or Mung Bean Nuclease. Once blunted, DNA is universally compatible with other blunt-ended fragments and vectors.

In another embodiment, the disclosure provides a GRID-seq method disclosed herein that comprises a step of ligating the RNA of isolated nuclei with a bivalent linker, wherein the bivalent linker comprises a segment of single stranded RNA and a segment of double stranded DNA. In a further embodiment, the 5'-end of the single stranded RNA segment of the bivalent linker is polyadenylated ("App" in FIG. 1A). In a further embodiment, the bivalent linker may further comprise a segment of DNA bound to RNA. Generally, the bivalent linker is comprised of two strands, a first/top strand and a second/bottom strand (referring to FIG. 1A). The top strand of the bivalent linker comprises DNA, while the bottom strand of the bivalent linker comprises DNA and RNA, or vice versa. In another embodiment, the top strand comprises a phosphorylated 5'-DNA end ("p" in FIG. 1A). A specific, but not limiting example of a bivalent linker includes a bivalent linker shown in FIG. 1A. In regards to the bivalent linker presented in FIG. 1A, it should be noted that this bivalent linker is presented as an example to show various elements that can make up the bivalent linker, and not that the particular sequence for the bivalent linker must or necessarily be identical to the sequence presented in FIG. 1A (see the discussion below).

In a certain embodiment, the bivalent linker may further comprise one or more recognition motifs for restriction enzymes. In a further embodiment, the recognition motifs may have the same sequence or alternatively have different sequence. In case of the former, the recognition motifs is cut by the same restriction enzyme; in the case of the latter, the recognition motifs are cut by different restriction enzymes. A list of possible restriction enzymes was presented above. For example, such restriction enzymes include, but are not limited to, AatII, AccI, AccIII, Acc65I, AccB7I, AgeI, AluI, Alw26I, Alw44I, ApaI, AvaI, AvaII, BalI, BamHI, BanI, BanII, BbuI, BclI, BglI, BglII, BsaMI, BsaOI, Bsp1286I, BsrBRI, BsrSI, BssHII, Bst71I, Bst98I, BstEII, BstOI, BstXI, BstZI, Bsu36I, CfoI, ClaI, CspI, Csp45I, DdeI, DpnI, DraI, Ec1HKI, Eco47III, Eco52I, EcoICRI, EcoRI, EcoRV, FokI, HaeII, HaeIII, HhaI, HincII, HindIII, HinfI, HpaI, HpaII, Hsp92I, Hsp92II, I-PpoI, KpnI, MboI, MboII, MluI, MmeI, MspI, MspA1I, NaeI, NarI, NciI, NcoI, NdeI, NdeII, NgoMIV, NheI, NotI, NruI, NsiI, PstI, PvuI, PvuII, RsaI, SacI, SacII, SalI, Sau3AI, Sau96I, ScaI, SfiI, SgfI, SinI, SmaI, SnaBI, SpeI, Sphi, SspI, StuI, StyI, TaqI, Tru9I, Tth111I, VspI, XbaI, XhoI, XhoII, XmaI, and XmnI.

In a certain embodiment, the bivalent linker may further comprise one or more barcode sequences which is used to identify amplified products. A "barcode" as used herein refers to a known nucleic acid sequence that allows some feature of a polynucleotide with which the barcode is associated to be identified. In some embodiments, the feature of the polynucleotide to be identified is the sample from which the polynucleotide is derived. In some embodiments, barcodes can be at least 2, 3, 4, 5, 6, 7, 8, 9, 10, 11, 12, 13, 14, 15, or more nucleotides in length. For example, barcodes can be at least 10, 11, 12, 13, 14, or 15 nucleotides in length. In some embodiments, barcodes can be shorter than 10, 9, 8, 7, 6, 5, or 4 nucleotides in length. For example, barcodes can be shorter than 10 nucleotides in length. In one embodiment, the barcode is between 2 to 7 nucleotides in length. In some embodiments, barcodes associated with some polynucleotides are of different length than barcodes associated with other polynucleotides. In general, barcodes are of sufficient length and comprise sequences that are sufficiently different to allow the identification of samples based on barcodes with which they are associated. In some embodiments, a barcode, and the sample source with which it is associated, can be identified accurately after the mutation, insertion, or deletion of one or more nucleotides in the barcode sequence, such as the mutation, insertion, or deletion of 1, 2, 3, 4, 5, 6, 7, 8, 9, 10, or more nucleotides. In some examples, 1, 2 or 3 nucleotides can be mutated, inserted and/or deleted. In some embodiments, each barcode in a plurality of barcodes differ from every other barcode in the plurality at least two nucleotide positions, such as at least 2, 3, 4, 5, 6, 7, 8, 9, 10, or more positions. In some examples, each barcode can differ from every other barcode by in at least 2, 3, 4 or 5 positions. In some embodiments, both a first site and a second site comprise at least one of a plurality of barcode sequences. In some embodiments, barcodes for second sites are selected independently from barcodes for first adapter oligonucleotides. In some embodiments, first sites and second sites having barcodes are paired, such that sequences of the pair comprise the same or different one or more barcodes. In some embodiments, the methods of the disclosure further comprise identifying the sample from which a target polynucleotide is derived based on a barcode sequence to which the target polynucleotide is joined. In general, a barcode may comprise a nucleic acid sequence that when joined to a target polynucleotide serves as an identifier of the sample from which the target polynucleotide was derived. In a particular embodiment, a stretch of RNA nucleotides comprises a barcode sequence. In an alternate embodiment, a stretch of DNA nucleotides comprises a barcode sequence.

As described above, the bivalent linker comprises combinations of deoxyribo- and ribo-nucleotides, and combinations of bases, including uracil, adenine, thymine, cytosine, guanine, inosine, xanthine hypoxanthine, isocytosine, isoguanine, etc. As used herein, the term "nucleoside" includes nucleotides and nucleoside and nucleotide analogs, and modified nucleosides such as amino modified nucleosides. In addition, "nucleoside" includes non-naturally occurring analog structures. Thus, e.g. the individual units of a peptide nucleic acid, each containing a base, are referred to herein as a nucleoside. When referring to DNA segments it will be readily apparent that the nucleotides in the DNA are A, G, T, and C. When referring to RNA segments it will be apparent that the nucleotides are A, G, U and C. Any sequence can be identified or "rendered" as RNA by replacing T with U. Thus, when reference to a sequence, if "T" is present, one of skill will recognize that by replacing T with U, the sequence can be identified as RNA.

The bivalent linker described herein is not limited by any particular sequence. Any number of oligonucleotide or polynucleotides useful for diagnostics, therapeutics and research can be used in the methods of the disclosure. Various sources/sequences of oligonucleotides and polynucleotides are available to one of skill in the art, including from GenBank, RNAcentral, RefSeq, Gene Expression Omnibus, Sequence Read Archive, dbGAP, cGhub, Genomic data commons, and ENCODE RNA Dashboard.

The practice of phosphoramidite chemistry to prepare oligonucleotides is known from the published work of M. Caruthers and S. Beaucage and others. U.S. Pat. Nos. 4,458,066, 4,500,707, 5,132,418, 4,415,732, 4,668,777, 4,973,679, 5,278,302, 5,153,319, 5,218,103, 5,268,464, 5,000,307, 5,319,079, 4,659,774, 4,672,110, 4,517,338, 4,725,677 and Re. 34,069, each of which is herein incorporated by reference, describe methods of oligonucleotide synthesis. Additionally, the practice of phosphoramidite chemistry has been systematically reviewed by Beaucage and Iyer in Beaucage, S. L. and Iyer, R. P., Tetrahedron, 1992, 48, 2223-2311 and Beaucage, S. L. and Iyer, R. P., Tetrahedron, 1993, 49, 6123-6194, or references referred to therein, all of which are herein incorporated by reference.

Nucleic acid synthesizers are commercially available and their use is generally understood by persons of ordinary skill in the art as being effective in generating nearly any oligonucleotide of reasonable length which may be desired.

In practicing phosphoramidite chemistry useful 5'OH sugar blocking groups are trityl, momomethoxytrityl, dimethoxytrityl and trimethoxytrityl, especially dimethoxytrityl (DMTr). In practicing phosphoramidite chemistry useful phosphite activating groups, i.e., $NR_2$, are dialkyl substituted nitrogen groups and nitrogen heterocycles. One approach includes the use of the di-isopropylamino activating group.

Oligonucleotides can be synthesized by a Mermade-6 solid phase automated oligonucleotide synthesizer or any commonly available automated oligonucleotide synthesizer. Triester, phosphoramidite, or hydrogen phosphonate coupling chemistries described in, for example, M. Caruthers, Oligonucleotides: Antisense Inhibitors of Gene Expression., pp. 7-24, J. S. Cohen, ed. (CRC Press, Inc. Boca Raton, Fla., 1989) or Oligonucleotide synthesis, a practical approach, Ed. M. J. Gait, IRL Press, 1984; "Oligonucleotides and Analogues, A Practical Approach", Ed. F. Eckstein, IRL Press, 1991, are employed by these synthesizers to provide the desired oligonucleotides. The Beaucage reagent, as described in, for example, Journal of American Chemical Society, 1990, 112, 1253-1255, or elemental sulfur, as described in Beaucage et al., Tetrahedron Letters, 1981, 22, 1859-1862, is used with phosphoramidite or hydrogen phosphonate chemistries to provide substituted phosphorothioate oligonucleotides. For example, the reagents comprising the protecting groups recited herein can be used in numerous applications where protection is desired. Such applications include, but are not limited to, both solid phase and solution phase, oligo-synthesis, polynucleotide synthesis and the like. The use of nucleoside and nucleotide analogs is also contemplated by this disclosure to provide oligonucleotide or oligonucleoside analogs bearing the protecting groups disclosed herein. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into an oligonucleotide or oligonucleoside sequence, they allow hybridization with a naturally occurring oligonucleotide sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

For instance, structural groups are optionally added to the ribose or base of a nucleoside for incorporation into an oligonucleotide, such as a methyl, propyl or allyl group at the 2'-0 position on the ribose, or a fluoro group which substitutes for the 2'-O group, or a bromo group on the ribonucleoside base. For use with phosphoramidite chemistry, various amidite reagents are commercially available, including 2'-deoxy amidites, 2'-O-methyl amidites and 2'-O-hydroxyl amidites. Any other means for such synthesis may also be employed. The actual synthesis of the oligonucleotides is well within the talents of those skilled in the art. It is also well known to use similar techniques to prepare other oligonucleotides such as the phosphorothioates, methyl phosphonates and alkylated derivatives. It is also well known to use similar techniques and commercially available modified amidites and controlled-pore glass (CPG) products such as biotin, Cy3, fluorescein, acridine or psoralen-modified amidites and/or CPG (available from Glen Research, Sterling Va.) to synthesize fluorescently labeled, biotinylated or other conjugated oligonucleotides.

In a further embodiment, the top strand and/or the bottom strand of a bivalent linker further comprises one or more nucleotides which comprise a capture moiety. A "capture moiety" as used herein refers to moiety that can bound by another molecule or compound in a highly selective manner, so as to allow for the capture/purification of a biomolecule to which the capture moiety is attached from other biomolecules which lack a capture moiety. Examples of a "capture moiety" include, but are not limited to, haptens, like dinitrophenol, biotin, fluorescein, and digoxigenin. Haptens can be bound in a highly selective manner by use of hapten specific antibodies, or in the case of biotin, by use of streptavidin. The agent (e.g., an antibody) that "captures" the capture moiety is typically bound to a solid support, such as beads.

In another embodiment, the disclosure provides a GRID-seq method disclosed herein that comprises a step of ligating DNA of the isolated nuclei with the double stranded DNA portion of a bivalent linker. Multiple ligases, each having characterized reaction condition, are known in the art, and include, without limitation NAD'-dependent ligases including tRNA ligase, Taq DNA ligase, *Thermus filiformis* DNA ligase, *Escherichia coli* DNA ligase, Tth DNA ligase, *Thermus scitoductus* DNA ligase, (I and II), thermostable ligase, Ampligase thermostable DNA ligase, VanC-type ligase, 9° N DNA Ligase, Tsp DNA ligase, and novel ligases discovered by bioprospecting; ATP-dependent ligases including T4 RNA ligase, T4 DNA ligase, T3 DNA ligase, T7 DNA ligase, Pfu DNA ligase, DNA ligase 1, DNA ligase III, DNA ligase IV, and novel ligases discovered by bioprospecting; and wild-type, mutant isoforms, and genetically engineered variants thereof.

Ligation can be between DNA segments having hybridizable sequences, such as complementary overhangs. Ligation can also be between two blunt ends. Generally, a 5' phosphate is utilized in a ligation reaction. The 5' phosphate can be provided by the target polynucleotide, the adapter oligonucleotide, or both. 5' phosphates can be added to or removed from DNA segments to be joined, as needed. Methods for the addition or rembvol of 5' phosphates are known in the art, and include without limitation enzymatic and chemical processes. Enzymes useful in the addition and/or removal of 5' phosphates include kinases, phosphatases, and polymerases. In some embodiments, both of the two ends joined in a ligation reaction (e.g., an adapter end and a target polynucleotide end) provide a 5' phosphate, such that two covalent linkages are made in joining the two ends. In some embodiment, only one of the two ends joined in a ligation reaction (e.g., only one of an adapter end and a target polynucleotide end) provides a 5' phosphate, such that only one covalent linkage is made in joining the two ends.

In a particular embodiment, the disclosure provides a GRID-seq method disclosed herein that comprises a step of capturing/binding a ligated bivalent linker by use of a capture agent bound to a solid support (e.g., streptavidin beads) that binds with the capture moiety in a highly selective manner so as to allow for purification of the bivalent linker from other biomolecules.

In a further embodiment, the disclosure provides a GRID-seq method disclosed herein that comprises a step of denaturing a captured ligated bivalent linker from a solid support so as to form two single stranded bivalent linkers, wherein one of the single stranded (ss)-ligated bivalent linker remains attached to the capture agent, while the second (ss)-bivalent linker is not attached to the capture agent. In certain embodiment, the second (ss)-bivalent linker lacks a capture moiety. The captured ligated bivalent linker can be denatured from a capture agent bound by heat treatment (e.g., heating at 94-95° C.), or by addition of a denaturant, e.g., such as a base (e.g., NaOH), formamide, and dimethyl sulfoxide.

In another embodiment, the disclosure provides a GRID-seq method disclosed herein that comprises a step of recovering an unbound single stranded ligated bivalent linker and converting the unbound ss-ligated bivalent linker to a double stranded (ds)-ligated bivalent linker using a polymerase enzyme. Numerous polymerases are known in the art. DNA polymerases can comprise DNA-dependent DNA polymerase activity, RNA-dependent DNA polymerase activity, or DNA-dependent and RNA-dependent DNA polymerase activity. DNA polymerases can be thermostable or non-thermostable. Example of DNA polymerases include, but are not limited to, Taq polymerase, Tth polymerase, Tli polymerase, Pfu polymerase, Pfutubo polymerase, Pyrobest polymerase, Pwo polymerase, KOD polymerase, Bst polymerase, Sac polymerase, Sso polymerase, Poc polymerase, Pab polymerase, Mth polymerase, Pho polymerase, ES4 polymerase, VENT polymerase, DEEPVENT polymerase, EX-Tag polymerase, LA-Taq polymerase, Expand polymerases, Platinum Taq polymerases, Hi-Fi polymerase, Tbr polymerase, Tfl polymerase, Tru polymerase, Tac polymerase, Tne polymerase, Tma polymerase, Tih polymerase, Tfi polymerase, Kienow fragment, and variants, modified products and derivatives thereof 3' end extension can be performed before or after pooling of target polymacleotides from independent samples.

In yet another embodiment, the disclosure provides a GRID-seq method disclosed herein that comprises a step of cutting the (ds)-ligated bivalent linker using one or more restriction enzymes, wherein the (ds)-ligated bivalent linker has recognition motifs for the one or more restriction enzymes. In a further embodiment, the (ds)-ligated bivalent linker has a recognition motif for a restriction enzyme at or near the end of the (ds)-ligated bivalent linker. In an alternate embodiment, the (ds)-ligated bivalent linker has a recognition motif for a restriction enzyme at or near both ends of the (ds)-ligated bivalent linker, wherein the recognition motif on the ends of the (ds)-ligated bivalent linker is the same, or alternatively different. In a further embodiment, the (ds)-ligated bivalent linker is cut ~20nt upstream and downstream from recognition sites found at the end(s) of the (ds)-ligated bivalent linker. In a particular embodiment, the recognition motif is recognized by MmeI.

In a particular embodiment, the disclosure provides a GRID-seq method disclosed herein that comprises a step of resolving and isolating the cut products of the (ds)-ligated bivalent linker based upon size differences between the products, wherein a cut (ds)-ligated bivalent linker that comprises a bivalent linker linked to both RNA and DNA is larger than a cut (ds)-ligated bivalent linker that is ligated to RNA or DNA. In a particular embodiment, a bivalent linker that is linked to both RNA and DNA is 20 bp or larger than the bivalent linker linked to only RNA or only DNA. In a further embodiment, the cut products of the (ds)-ligated bivalent linker can be resolved using a gel (e.g., an agarose gel). In an alternate embodiment, the cut products of the (ds)-ligated bivalent linker can be resolved using size exclusion or affinity chromatography.

In an another embodiment, the disclosure provides a GRID-seq method disclosed herein that comprises a step of attaching an adapter to isolated cut (ds)-ligated bivalent linkers that are ligated to both RNA and DNA.

An adapter oligonucleotide includes any oligonucleotide having a sequence, at least a portion of which is known, that can be joined to a target polynucleotide. Adapter oligonucleotides can comprise DNA, RNA, nucleotide analogues, non-canonical nucleotides, labeled nucleotides, modified nucleotides, or combinations thereof. Adapter oligonucleotides can be single-stranded, double-stranded, or partial duplex. In general, a partial-duplex adapter comprises one or more single-stranded regions and one or more double-stranded regions. Double-stranded adapters can comprise two separate oligonucleotides hybridized to one another (also referred to as an "oligonucleotide duplex"), and hybridization may leave one or more blunt ends, one or more 3' overhangs, one or more 5' overhangs, one or more bulges resulting from mismatched and/or unpaired nucleotides, or any combination of these. In some embodiments, a single-stranded adapter comprises two or more sequences that are able to hybridize with one another. When two such hybridizable sequences are contained in a single-stranded adapter, hybridization yields a hairpin structure (hairpin adapter). When two hybridized regions of an adapter are separated from one another by a non-hybridized region, a "bubble" structure results. Adapters comprising a bubble structure can consist of a single adapter oligonucleotide comprising internal hybridizations, or may comprise two or more adapter oligonucleotides hybridized to one another. Internal sequence hybridization, such as between two hybridizable sequences in an adapter, can produce a double-stranded structure in a single-stranded adapter oligonucleotide. Adapters of different kinds can be used in combination, such as a hairpin adapter and a double-stranded adapter, or adapters of different sequences. Hybridizable sequences in a hairpin adapter may or may not include one or both ends of the oligonucleotide. When neither of the ends are included in the hybridizable sequences, both ends are "free" or "overhanging." When only one end is hybridizable to another sequence in the adapter, the other end forms an overhang, such as a 3' overhang or a 5' overhang. When both the 5'-terminal nucleotide and the 3'-terminal nucleotide are included in the hybridizable sequences, such that the 5'-terminal nucleotide and the 3'-terminal nucleotide are complementary and hybridize with one another, the end is referred to as "blunt." Different adapters can be joined to target polynucleotides in sequential reactions or simultaneously. For example, the first and second adapters can be added to the same reaction. Adapters can be manipulated prior to combining with target polynucleotides. For example, terminal phosphates can be added or removed.

Adapters can contain one or more of a variety of sequence elements, including but not limited to, one or more amplification primer annealing sequences or complements thereof, one or more sequencing primer annealing sequences or complements thereof, one or more barcode sequences, one or more common sequences shared among multiple different adapters or subsets of different adapters, one or more restriction enzyme recognition sites, one or more overhangs complementary to one or more target polynucleotide overhangs, one or more probe binding sites (e.g. for attachment to a sequencing platform, such as a flow cell for massive parallel sequencing, such as developed by Illumina, Inc.), one or more random or near-random sequences (e.g. one or more nucleotides selected at random from a set of two or more different nucleotides at one or more positions, with each of the different nucleotides selected at one or more positions represented in a pool of adapters comprising the random sequence), and combinations thereof. Two or more sequence elements can be non-adjacent to one another (e.g., separated by one or more nucleotides), adjacent to one another, partially overlapping, or completely overlapping. For example, an amplification primer annealing sequence can also serve as a sequencing primer annealing sequence. Sequence elements can be located at or near the 3' end, at or near the 5' end, or in the interior of the adapter oligonucleotide. When an adapter oligonucleotide is capable of forming secondary structure, such as a hairpin, sequence elements can be located partially or completely outside the secondary structure, partially or completely inside the secondary structure, or in between sequences participating in the secondary structure. For example, when an adapter oligonucleotide comprises a hairpin structure, sequence elements can be located partially or completely inside or outside the hybridizable sequences (the "stem"), including in the sequence between the hybridizable sequences (the "loop"). In some embodiments, the first adapter oligonucleotides in a plurality of first adapter oligonucleotides having different barcode sequences comprise a sequence element common among all first adapter oligonucleotides in the plurality. In some embodiments, all second adapter oligonucleotides comprise a sequence element common among all second adapter oligonucleotides that is different from the common sequence element shared by the first adapter oligonucleotides. A difference in sequence elements can be any such that at least a portion of different adapters do not completely align, for example, due to changes in sequence length, deletion or insertion of one or more nucleotides, or a change in the nucleotide composition at one or more nucleotide positions (such as a base change or base modification). In some embodiments, an adapter oligonucleotide comprises a 5' overhang, a 3' overhang, or both that is complementary to one or more target polynucleotides. Complementary overhangs can be one or more nucleotides in length, including but not limited to 1, 2, 3, 4, 5, 6, 7, 8, 9, 10, 11, 12, 13, 14, 15, or more nucleotides in length. For example, the complementary overhangs can be about 1, 2, 3, 4, 5 or 6 nucleotides in length. Complementary overhangs may comprise a fixed sequence. Complementary overhangs may comprise a random sequence of one or more nucleotides, such that one or more nucleotides are selected at random from a set of two or more different nucleotides at one or more positions, with each of the different nucleotides selected at one or more positions represented in a pool of adapters with complementary overhangs comprising the random sequence. In some embodiments, an adapter overhang is complementary to a target polynucleotide overhang produced by restriction endonuclease digestion. In some embodiments, an adapter overhang consists of an adenine or a thymine.

Adapter oligonucleotides can have any suitable length, at least sufficient to accommodate the one or more sequence elements of which they are comprised. In some embodiments, adapters are about, less than about, or more than about 10, 15, 20, 25, 30, 35, 40, 45, 50, 55, 60, 65, 70, 75, 80, 90, 100, 200, or more nucleotides in length. In some examples, the adaptors can be about 10 to about 50 nucleotides in length. In further examples, the adaptors can be about 20 to about 40 nucleotides in length.

In a certain embodiment, the disclosure provides a GRID-seq method disclosed herein that comprises a step of deep sequencing the adapter (ds)-ligated bivalent linkers to generate sequencing reads. Examples of sequencing methods which can be used with the methods of the disclosure include, but are not limited to, 454 pyrosequencing methods developed Roche Diagnostics, "clusters" sequencing methods developed by Illumina, SOLiD and Ion semiconductor sequencing methods developed by Life Technologies, and DNA nanoball sequencing methods developed by Complete Genomics.

In a further embodiment, the disclosure provides a GRID-seq method disclosed herein that comprises a step of segregating the sequencing read by barcodes to create GRID-seq libraries.

In a particular embodiment, the disclosure provides a GRID-seq method comprising one or more of the following steps: stabilizing RNAs on chromatin by fixing cells (e.g., double fixing with disuccinimidyl glutarate (DSG) and formaldehyde); isolating nuclei; digesting DNA in situ with an restriction enzyme, typically a frequent cutting restriction enzyme such as AluI; ligating in situ a bivalent linker to RNA of the isolated nuclei, wherein the bivalent linker comprises an ssRNA portion for ligation to RNA, a dsDNA portion for ligation to genomic DNA, a biotin conjugated nucleotide, and recognition sites for a restriction enzyme (e.g., MmeI); washing away excess free linkers; extending the bivalent linker with reverse transcriptase into the ligated RNA region; ligating the bivalent linker to genomic DNA of the nuclei in situ; purifying the ligated bivalent linker by affinity purification with streptavidin beads; denaturing the streptavidin bound ligated bivalent linker to release a ssDNA ligated bivalent linker from the streptavidin beads; converting the ssDNA ligated bivalent linker into a dsDNA ligated bivalent linker; cutting the dsDNA ligated bivalent linker with the type II restriction enzyme (e.g., MmeI) to form cut products, wherein the dsDNA is cut ~20 nt upstream and downstream from the two built in restriction recognition sites (e.g., MmeI sites) in the linker; resolving the cut products in a native gel to detect two defined DNA fragments with the larger one corresponding to a bivalent linker ligated to both RNA and DNA and the smaller one corresponding to a bivalent linker ligated to either RNA or DNA; isolating the larger DNA fragment; ligating the larger DNA fragment with an adapter; amplifying and deep sequencing the DNA fragment/adapter, typically generating more than 200 million 100 nt raw sequencing reads (~40 million uniquely mapped read mates) can be generated from the DNA fragment/adapter (i.e., a library of sequencing reads for the cells).

In some embodiments, one or more amplification and/or replication steps are used for the preparation of a library to be sequenced. Any amplification method known in the art may be used. Examples of amplification techniques that can be used include, but are not limited to, quantitative PCR, quantitative fluorescent PCR (QF-PCR), multiplex fluorescent PCR (MF-PCR), real time PCR (RTPCR), single cell PCR, restriction fragment length polymorphism PCR (PCR-RFLP), PCK-RFLPIRT-PCR-IRFLP, hot start PCR, nested PCR, in situ polonony PCR, in situ rolling circle amplification (RCA), bridge PCR, ligation mediated PCR, Qb replicase amplification, inverse PCR, picotiter PCR and emulsion PCR. Other suitable amplification methods include the ligase chain reaction (LCR), transcription amplification, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR) and nucleic acid based sequence amplification (NABSA). Other amplification methods that can be used herein include those described in U.S. Pat. Nos. 5,242,794; 5,494,810; 4,988,617; and 6,582,938.

In particular embodiments, PCR is used to amplify DNA molecules after they are dispensed into individual partitions. In some cases, one or more specific priming sequences within amplification adapters are utilized for PCR amplification. The amplification adapters may be ligated to fragmented DNA molecules before or after dispensing into individual partitions. Polynucleotides comprising amplification adapters with suitable priming sequences on both ends can be PCR amplified exponentially. Polynucleotides with only one suitable priming sequence due to, for example, imperfect ligation efficiency of amplification adapters comprising priming sequences, may only undergo linear amplification. Further, polynucleotides can be eliminated from amplification, for example PCR amplification, all together, if no adapters comprising suitable priming sequences are ligated. In some embodiments, the number of PCR cycles vary between 10-30, but can be as low as 9, 8, 7, 6, 5, 4, 3, 2 or less or as high as 40, 45, 50, 55, 60 or more. As a result, exponentially amplifiable fragments carrying amplification adapters with a suitable priming sequence can be present in much higher (1000 fold or more) concentration compared to linearly amplifiable or un-amplifiable fragments, after a PCR amplification. Benefits of PCR, as compared to whole genome amplification techniques (such as amplification with randomized primers or Multiple Displacement Amplification using phi29 polymerase) include, but are not limited to a more uniform relative sequence coverage—as each fragment can be copied at most once per cycle and as the amplification is controlled by thermocycling program, a substantially lower rate of forming chimeric molecules than for example MDA (Lasken et al., 2007, BMC Biotechnology)—as chimeric molecules pose significant challenges for accurate sequence assembly by presenting nonbiological sequences in the assembly graph, which may result in higher rate of misassemblies or highly ambiguous and fragmented assembly, reduced sequence specific biases that may result from binding of randomized primers commonly used in MDA versus using specific priming sites with a specific sequence, a higher reproducibility in the amount of final amplified DNA product, which can be controlled by selection of the number of PCR cycles, and a higher fidelity in replication with the polymerases that are commonly used in PCR as compared to common whole genome amplification techniques known in the art.

To infer specific RNA-chromatin interactions, a background can also be generated which is based upon non-specific RNA-chromatin interactions by mixing nuclei isolated from two different species (e.g., *Drosophila* and humans), and/or the used of endogenous RNAs.

The methods disclosed herein have broad applicability and can be used to study epigenetics, transcription and molecular biology. Moreover, the methods disclosed herein can be used for diagnostic applications, including detecting/discovering molecular markers in various human/animal disease, which often show abnormal patterns of RNA interactions with chromatin.

Kits and articles of manufacture are also described herein. Such kits can comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers can be formed from a variety of materials such as glass or plastic. For example, a container(s) can comprise one or more bivalent linkers described herein. A kit will typically comprise one or more additional containers, each with one or more of various materials (such as reagents, optionally in concentrated form, and/or devices) desirable from a commercial and user standpoint for use with the methods disclosed herein. Non-limiting examples of such materials include, but are not limited to, buffers, diluents, filters, columns; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself, a label can be associated with a container when it is present within a receptacle or carrier that also holds the container, e.g., as a package insert. A label can be used to indicate that the contents are to be used for a application, such as a diagnostic application. The label can also indicate directions for use of the contents, such as in the methods described herein.

The following examples are intended to illustrate but not limit the disclosure. While they are typical of those that might be used, other procedures known to those skilled in the art may alternatively be used.

Examples

Cell culture. MDA-MB-231 breast cancer cells (HTB-26 ATCC) and MM.1S multiple myeloma cells were grown at 37° C. and 5% $CO_2$. MDA-MB-231 cells were cultured in Dulbecco's Modified Eagle Medium (Thermo Fisher Sci.) supplemented with 10% fetal bovine serum. MM.1S cells were cultured in RPMI-1640 supplemented with 1% GlutaMAX (Thermo Fisher Sci.) and 10% fetal bovine serum. For JQ1 treatment, MDA-MB-231 cells were resuspended in fresh media containing 500 nM JQ1 (a gift from ChengMing Chiang, UT Southwestern) or 0.05% DMSO as vehicle for a duration of 6 h. Drosophila S2 cells were cultured in Schneider's Drosophila Medium (Thermo Fisher Sci.) supplemented with 10% fetal bovine serum and 2 mM L-glutamine (Thermo Fisher Sci.), at ambient temperature in ambient $CO_2$.

Figure 1B:
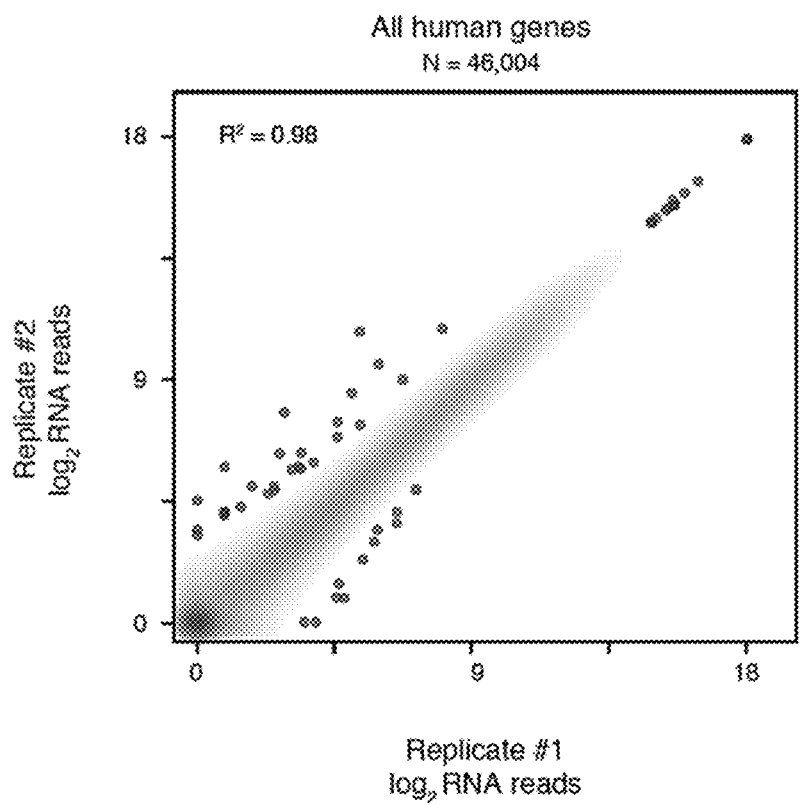
Figure 1C:
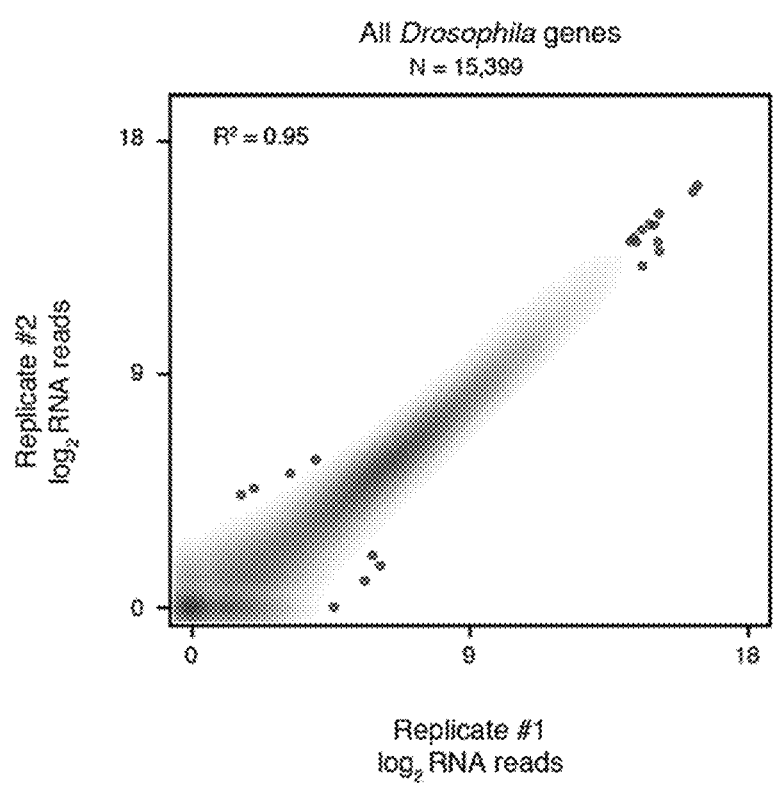

Construction of GRID-seq library. A bivalent linker was chemically synthesized (IDT), as illustrated in FIG. 1. The DNA strand consists of: 5'-/5Phos/GTTGGAGTTCGGTGTGTGGGAGTGAGCTGTGTC-3' (SEQ ID NO:1), and the DNA/RNA hybrid strand contains 5'-/5Phos/rGrUrUrGrGrArUrUrCrNrNrNrGrACACAGC/iBiodT/CACTCCCACACACCGAACT CCAAC-3' (little "r" denotes RNA portion; rN: Random ribonucleotide; iBiodT: biotin-conjugated T) (SEQ ID NO:2). The DNA/RNA hybrid stand was pre-adenylated by using the DNA 5' Adenylation Kit (NEB) following the manufacturer's instructions, and was purified by Phenol:Chloroform:Isoamyl Alcohol (pH 8.0, Thermo Fisher Sci.) followed by ethanol precipitation. Equal molar quantity of the two stands were mixed, incubated at 80° C. for 5 min, and annealed after slow cooling to ambient temperature at approximately 0.1° C. per sec. The annealed linker was adjusted to the final concentration of 8 pmol/μL. The annealed bivalent linker is depicted in FIG. 1A.

Approximately 2 million mammalian cells or 10 million Drosophila cells were used for each GRID-seq library construction. Cells were washed twice with PBS and crosslinked for 45 min at ambient temperature with 2 mM PBS-diluted DSG solution. Cells were washed and further crosslinked for 10 min at ambient temperature with a 3% PBS-diluted formaldehyde solution followed by quenching formaldehyde with 350 mM Glycine. Cells were washed twice with PBS and incubated in 500 μL of Buffer A (10 mM Tris-Cl pH 7.5, 10 mM NaCl, 0.2% NP-40, 1 U/μL RiboLock (Thermo Fisher Sci.), 1× Protease inhibitor (Sigma-Aldrich)) for 15 min on ice. To prepare nuclei, fixed cells were washed in 200 μL of 1× Tango Buffer (Thermo Fisher Sci.) and then incubated in 320 μL of Buffer B (1× Tango Buffer, 0.2% SDS) for 10 min at 62° C. SDS was immediately quenched with 50 μL of 10% Triton X-100 and the integrity of nuclei was examined under microscope. Nuclei were collected, washed twice with 1× Tango Buffer, resuspended in 500 μL of AluI solution (1× Tango Buffer, 1 U/μl RiboLock, 1× Protease inhibitor, 1% Triton X-100, 0.5 U/μL AluI (Thermo Fisher Sci.)), and incubated at 37° C. for 2 h with agitation. Nuclei were collected, resuspended in 400 μL of PNK solution (1× Tango Buffer, 1 U/μl RiboLock, 1× Protease inhibitor, 1 mM ATP, 0.35 U/μL T4 PNK (Thermo Fisher Sci.)), and incubated at 37° C. for 1.5 h with agitation.

For in situ linker ligation to RNA. Prepared nuclei were washed twice with 200 μL of 1×RNA Ligase Buffer (NEB), resuspended in 500 μL of RNA ligation solution (1×RNA Ligase Buffer, 1 U/μl RiboLock, 0.4 pmol/μL pre-adenylated linker, 4 U/μL T4 RNA Ligase 2-truncated KQ (NEB), 15% PEG-8000), and incubated at 25° C. for 2 h. For primer extension, 10 μL of $H_2O$, 36 μL of 1 M KCl, 32 μL of 10 mM dNTP mix, 28 μL of 5× RT First Strand Buffer (Thermo Fisher Sci.), 28 μL of 100 mM DTT and 5 μL of SuperScript III Reverse Transcriptase were mixed directly into the suspension, and the reaction was incubated at 50° C. for 45 min.

For in situ linker ligation to AluI-cut genomic DNA. Nuclei were collected, washed twice with 200 μl of 1×DNA Ligase Buffer (NEB) to remove free linker, resuspended in 1.2 mL of DNA Ligation Solution (0.2 U/μL RiboLock, 1×DNA Ligase Buffer, 1 mg/mL BSA, 1% Triton X-100, 1 U/μL T4 DNA Ligase (Thermo Fisher Sci.)) and incubated overnight at 16° C. with rotation. Nuclei were collected, washed with PBS, resuspended in 266 μL of Proteinase K solution (50 mM Tris-Cl pH 7.5, 100 mM NaCl, 1 mM EDTA, 1% SDS, 1 mg/mL Proteinase K (Thermo Fisher Sci.) and incubated at 65° C. for 30 min. After adding 20 μL of 5 M NaCl, protease-treated nuclei were incubated for another 1.5 h. Total DNA was extracted, dissolved in B&W Buffer (5 mM Tris-Cl pH 7.5, 1 M NaCl, 0.5 mM EDTA, 0.02% Tween-20). 300 μg of Streptavidin-conjugated magnetic beads were washed with B&W Buffer and mixed with purified DNA for affinity purification of biotinylated linker. After incubation at 37° C. for 30 min, beads were extensively washed for 5 times with B&W Buffer, and incubated in 100 μL of 150 mM NaOH at ambient temperature for 10 min. Cleared supernatant was collected, neutralized with 6.5 μL of 1.25 M Acetic Acid, and diluted with 11 μL of 10× TE Buffer (100 mM Tris-Cl pH 7.5, 10 mM EDTA). Released ssDNA was precipitated by isopropanol from the supernatant and dissolved in 30 μL of $H_2O$. Second strand synthesis was performed by mixing ssDNA with 250 ng Random Hexamer Primers and 5 μL of 10×NEB Buffer CutSmart, incubating at 98° C. for 5 min, adding 8.5 μl of $H_2O$, 5 pmol dNTP and 5 U Klenow Fragment (3' to 5' exo-)enzyme (NEB) and incubating at 37° C. for 1 h. After heat inactivation at 70° C. for 10 min, 5 pmol S-adenosylmethionine (NEB) and 1 U MmeI enzyme (NEB) was added and incubated at 37° C. for 30 min followed by addition of another 3 U MmeI and incubation for 30 min. The reaction was treated with 40 μg Proteinase K at 65° C. for 20 min. Digested DNA was extracted and purified before loading to 12% native PAGE gel for size-selection. The desired band at 84 bp was excised and DNA was extracted.

Adapters were prepared by annealing the following two oligonucleotides (IDT) in 1×NEB Buffer 2 to a final concentration of 25 mM: 5'-/5Phos/AGATCGGAAGAGCACACGTCT-3' (SEQ ID NO:3) and 5'-ACACTCTTTCCCTACACGACGCTCTTCC-GATCTNN-3' (SEQ ID NO:4). Purified DNA was dissolved in 10 μL of 1×NEB Buffer CutSmart and 0.5 U Shrimp Alkaline Phosphatase (NEB), incubated at 37° C. for 30 min and heat inactivated at 65° C. for 5 min. The reaction was diluted with 36 μL $H_2O$, mixed with 10 μL of 10× T4 DNA Ligase Buffer (NEB), 32 μL of PEG-6000, 200 pmol of Adapters and 1,600 U T4 DNA Ligase (NEB), and incubated at ambient temperature for 1 h. Unligated nick was phosphorylated by 20 U T4 Polynucleotide Kinase (NEB) supplemented by 100 pmol ATP and incubated at 37° C. for 30 min. Nick was then ligated by addition of 1 μL of 10× T4 DNA Ligase Buffer, 100 pmol ATP and 1,600 U T4 DNA Ligase (NEB), and incubated at ambient temperature for 30 min. DNA along with excessive Adapters were extracted and purified before loading to 10% native PAGE gel for sizeselection. The desired band at approximately 185 bp was excised. DNA was extracted and dissolved in 20 μL of $H_2O$. To amplify each library, 20 μL of PCR amplification mix (9.4 μL of $H_2O$, 5 μL of DNA sample, 4 μL of 5× Phusion HF Buffer, 40 pmol dNTP, 5 pmol Primer #1, 5 pmol Primer #2, 0.4 U Phusion High-Fidelity DNA Polymerase (Thermo Fisher Sci.)) was prepared. PCR primers consist of Primer #1 (5'-AATGATACGGCGACCACCGAGATCTA-CACNNNNNACACTCTTTCCCTA-CACGACGCTCTTCCGATCT-3' (NNNNN: 5 nt barcode for multiplexing libraries)) (SEQ ID NO:5) and Primer #2 (5'-CAAGCAGAAGACGGCATACGA-GACGTGTGCTCTTCCGATCT-3') (SEQ ID NO:6). PCR was performed with an initial 30 sec denaturation at 98° C., followed by 16 cycles of 10 sec denaturation at 98° C., 30 sec annealing at 65° C. and 15 sec extension at 72° C. The PCR product was separated on a native 10% PAGE gel and the band at 188 bp was recovered. DNA was subsequently subjected to Illumina HiSeq 2500 for single-end 100 bp sequencing, with the sequencing primer (5'-ACACTCTTTCCCTACACGACGCTCTTCCGATCT-3') (SEQ ID NO:7).

Parallel analysis of Human-*Drosophila* mixed nuclei. To set up a Human-*Drosophila* mix, MDA-MB-231 and S2 cells were independently double-crosslinked and collected, from which nuclei were isolated and counted. Pilot experiments indicated that human MDA-MB-231 nuclei and *Drosophila* S2 nuclei at a 1:5 ratio contain roughly equal amounts of total nucleic acid, and accordingly, 1 million MDA-MB-231 nuclei and 5 million S2 nuclei were mixed. The construction of the mix library was performed in parallel with 2 million MDA-MB-231 cell nuclei and 10 million S2 cell nuclei.

GRID-seq raw data processing and mapping. Upon sequencing, individual libraries were segregated according to multiplexing barcodes and then both barcode and residual adapter sequences were removed from each tag to produce tags with non-uniform length, the majority of which ranged from 84 bp to 87 bp in each library. To precisely remove linker sequence from the DNA and cDNA tags, MmeI motifs were used for defining linker boundaries. Linker orientation also dictated whether the tags at each side were originated from genomic DNA or RNA. To minimize the loss of tags due to sequencing errors, tags were first filtered based on the presence of two opposite-orientated MmeI motifs, then aligned to the linker sequence from both directions to determine its orientation. DNA and corresponding RNA tags, most of which ranged from 18 bp to 23 bp, were extracted for alignment. All processed tags were aligned to their indicated genome build using Bowtie2 with parameter of—local. Human samples were aligned to genome build hg38 and *Drosophila* samples to genome build dm3 with parameters –q 2. To estimate the numbers of cross-species-ligated RNA and DNA tags in the mix of MDA-MB-231 and S2 cell nuclei, RNA tags were first aligned independently to the transcriptome builds of hg38 and dm3, with the most stringent parameter of –q 44. Linked DNA tags of those RNA tags that were unambiguously aligned to human transcriptome were then aligned to human genome with the parameter of –q 2. These DNA tags failed to align to the human genome were then aligned to the *Drosophila* genome, with the parameter of –q 2. Conversely, DNA tags linked to the RNA tags that were unambiguously aligned (–q 44) to the *Drosophila* transcriptome were first aligned to the *Drosophila* genome (–q 2), and those unaligned DNA tags were then aligned to the human genome (–q 2). Seven GRID-seq libraries were generated from the current study (see Table 1):

TABLE 1

| Species | Samples | Raw tags | Linker-clipped tags | Uniquely mapped tag pairs (% of alignment filtering) |
|---|---|---|---|---|
| *Drosophila* | S2 Rep1 | 113.7M | 95.7M | 4.5M (4.7%) |
| *Drosophila* | S2 Rep2 | 165.7M | 74.0M | 2.0M (2.7%) |
| Mixed | MDA-MB-231 + S2 | 46.2M | 38.7M | — |
| Human | MDA-MB-231 Rep1 | 213.0M | 168.0M | 44.0M (26.2%) |
| Human | MDA-MB-231 Rep2 | 294.9M | 144.8M | 40.3M (27.8%) |
| Human | MM.1S Rep1 | 300.8M | 135.0M | 37.7M (27.9%) |
| Human | MM.1S Rep2 | 363.6M | 149.6M | 39.2M (26.2%) |

Identification of hit RNAs. Genomic regions with enriched GRID-seq RNA reads were detected by MACS2 using the model for broad-peak detection. These mapped regions with significant enrichment (p<0.001) and overlapping with known-gene annotation (Ensemble genes GRCh38.83 for human and BDGP5.78 for *Drosophila*) were assigned to their respective largest annotated genes. Enriched regions that did not overlap with any known gene were assigned as "unannotated transcripts". The RNA read-coverage of genomic regions was calculated by BEDtools and SAMtools. The genes with the tag-coverage above the sliding-window threshold [$(N_{i+n}-N_i) \geq n$, where i was the rank of given RNA, N was the read-counts of this RNA and n was the 1/100 of the total number of ranked RNAs] were selected as abundant chromatin-interacting RNAs. A subset of abundant RNAs with sufficient RNA read-density [RPK (reads per Kb)≥100] or with significant DNA read-densities (RPK≥10) associated at any genomic region was identified as hit RNAs for further analysis (see Tables 2-4 of Provisional Application No. 62/371,429, which are incorporated herein by reference). A small portion of Tables 2-4 are presented below. (Tables 2-4 comprise more than 800 data points):

TABLE 2

(partial listing)
Human MDA-MB-231 Hit RNAs

| Chromosome | Gene Start | Gene End | Ensembl Gene ID | Gene Symbol | Gene Type | Raw reads |
|---|---|---|---|---|---|---|
| chr1 | 28578538 | 28582983 | ENSG00000197989 | SNHG12 | antisense | 9878 |
| chr1 | 244840638 | 244846903 | ENSG00000188206 | HNRNPU-AS1 | antisense | 3484 |
| chr1 | 85482281 | 85578250 | ENSG00000282057 | RP4-621F18.2 | lincRNA | 18564 |
| chr1 | 109100193 | 109100619 | ENSG00000270066 | SCARNA2 | lincRNA | 7171 |
| chr1 | 198807493 | 198937429 | ENSG00000229989 | MIR181A1HG | lincRNA | 37447 |

TABLE 2-continued (partial listing)
Human MDA-MB-231 Hit RNAs

| Chromosome | Gene Start | Gene End | Ensembl Gene ID | Gene Symbol | Gene Type | Raw reads |
|---|---|---|---|---|---|---|
| chr1 | 207801518 | 207869150 | ENSG00000203709 | C1orf132 | lincRNA | 12108 |
| chr1 | 173791548 | 173791887 | ENSG00000200674 | RN7SKP160 | misc_RNA | 71402 |
| . | | | | | | |
| . | | | | | | |
| . | | | | | | |
| chrX | 109624244 | 109733403 | ENSG00000068366 | ACSL4 | protein_coding | 18508 |
| chrX | 123600561 | 123733056 | ENSG00000125676 | THOC2 | protein_coding | 16472 |
| chrX | 150361422 | 150514178 | ENSG00000013619 | MAMLD1 | protein_coding | 44691 |
| chrX | 154348524 | 154374638 | ENSG00000196924 | FLNA | protein_coding | 9014 |
| chrX | 74200229 | 74242148 | ENSG00000271430 | RP3-368A4.5 | sense_intronic | 25362 |

TABLE 3

(partial listing)
Human MM.1S Hit RNAs

| Chromosome | Gene Start | Gene End | Ensembl Gene ID | Gene Symbol | Gene Type | Raw reads | S |
|---|---|---|---|---|---|---|---|
| chr1 | 41014590 | 41043890 | ENSG00000281207 | SLFNL1-AS1 | antisense | 5091 | + |
| chr1 | 156646507 | 156661424 | ENSG00000229953 | RP11-284F21.7 | antisense | 4887 | − |
| chr1 | 225840883 | 225846522 | ENSG00000242861 | RP11-285F7.2 | antisense | 4766 | − |
| chr1 | 244840638 | 244846903 | ENSG00000188206 | HNRNPU-AS1 | antisense | 7611 | − |
| chr1 | 207801518 | 207869150 | ENSG00000203709 | C1orf132 | lincRNA | 17862 | − |
| . | | | | | | | |
| . | | | | | | | |
| . | | | | | | | |
| chrX | 48922028 | 48958386 | ENSG00000068308 | OTUD5 | protein_coding | 4758 | |
| chrX | 53532096 | 53686729 | ENSG00000086758 | HUWE1 | protein_coding | 19664 | |
| chrX | 71533083 | 71575897 | ENSG00000147162 | OGT | protein_coding | 29011 | |
| chrX | 103675496 | 103688158 | ENSG00000123562 | MORF4L2 | protein_coding | 5073 | |
| chrX | 119615724 | 119693370 | ENSG00000125354 | 6-Sep | protein_coding | 20475 | |
| chrX | 74200229 | 74242148 | ENSG00000271430 | RP3-368A4.5 | sense_intronic | 21176 | |

TABLE 4

(partial listing)
*Drosophila* S2 Hit RNAs

| Chromosome | Gene Start | Gene End | Flybase Gene ID | Gene Symbol | Gene Type | Raw reads | S |
|---|---|---|---|---|---|---|---|
| chr2L | 3046746 | 3046904 | FBgn0263847 | CR43708 | ncRNA | 4347 | + |
| chr2L | 8485725 | 8485925 | FBgn0263489 | unsRNA:d-a | ncRNA | 8416 | + |
| chr2L | 9787279 | 9790745 | FBgn0042174 | CR18854 | ncRNA | 2414 | − |
| chr2L | 9893805 | 9895003 | FBgn0063449 | Uhg2 | ncRNA | 16651 | − |
| chr2L | 9839 | 21376 | FBgn0002121 | l(2)gl | protein_coding | 3669 | − |
| . | | | | | | | |
| . | | | | | | | |
| chrX | 21257872 | 21257962 | FBgn0025882 | snoRNA:MeU6-A47 | snoRNA | 1260 | − |
| chrX | 16148705 | 16148896 | FBgn0003920 | snRNA:U2:14B | snRNA | 1711 | + |
| chrX | 3216721 | 3246369 | Tx.32 | Tx.32 | unannotated | 3085 | − |
| chrX | 11089940 | 11093547 | Tx.34 | Tx.34 | unannotated | 1199 | − |
| chrX | 14618421 | 14653939 | Tx.36 | Tx.36 | unannotated | 5708 | + |

Construction of background for non-specific RNA-chromatin interactions. To determine the specific RNA-chromatin interaction pattern of each hit RNA, a genome-wide background for non-specific interactions was developed. Ideally, for each library, a setup would include mixed nuclei from different species in order to evaluate cross-species RNA-chromatin interactions, which would represent the true background. In practice, it is feasible to generate such background with sufficient density on the *Drosophila* genome by using RNA reads from human cells because of the much smaller *Drosophila* genome, but the RNA density on the human genome based on the RNA reads from *Drosophila* is often too scattered to provide a reliable background. Based on endogenous RNA reads in comparison with the true background based on cross-species RNA-chromatin interactions, it was attempted to deduce the background in *Drosophila* genome. Toward this goal, RNAs were selected from protein-coding genes engaged in trans-chromosomal interactions. From which, their density on the 1 Kb-binned genome was calculated, smoothed by a moving widow of 100 Kb, and then normalized by the total read number and chromosome size. The resulting background in the *Drosophila* genome was found to be highly correlated with the cross-species background. Using this strategy enabled the deduction of the background in human cells by using endogenous RNA reads.

Normalization of RNA-chromatin interactions and construction of genomic binding matrix. To evaluate specific RNA-chromatin interactions of each hit RNA at each genomic bin, the DNA reads for each gene at each genomic bin were first summarized, and then normalized to 1 million reads. After which, the total number of bins of each chromosome was further normalized. A ratio was calculated by dividing the normalized DNA read density with background read density, which represents the specific binding of RNA at the genomic bin. To construct a robust global binding matrix for all hit RNAs, genomic bins with significant binding level (at least 3 bins with binding level ≥2 in every 10 bin-window) were preserved and further smoothed by a moving-widow of 10 bins. All subsequent analysis involving binding levels and patterns were based on such genomic binding matrix.

Identification of active enhancers and inference of enhancer-promoter connectivity. Active enhancers were identified by using published H3K27ac ChIP-seq data. Briefly, enriched peaks of H3K27ac were first detected by MACS2; the peaks within 2.5 Kb around known promoters were removed; and the qualified peaks were stitched together within a 12.5 Kb region.

As specific binding at enhancers indicated specific footprints of hit RNA on the chromatin, a statistical model to identify significant long-distance RNA-chromatin interactions was built between enhancer and promoters based on trans-chromosomal interactions from hit RNAs of protein-coding genes. This model was used with a stringent confidence threshold (Z-score ≥3) in order to segregate the interaction levels of travelling RNAs across the nuclear space from those likely due to the spatial proximity in 3D genome.

Construction of enhancer-promoter network. The enhancer-promoter network was constructed with inferred enhancer-promoter pairs at different significance levels. The enhancer-promoter network exhibited significant intra- and inter-chromosomal interactions (see Table-5 of Provisional Application No. 62/371,429, which is incorporated herein by reference). A small portion of Table 5 is presented below (Table 5 has more than 8000 data points):

TABLE 5

(Partial listing)

| Ensemble Gene ID | Gene Symbol | Gene Type | Enhancer Coordinate | Enh Type | Interaction Type |
|---|---|---|---|---|---|
| ENSG00000003400 | CASP10 | protein_coding | chr2:201049717:201058360 | TE | Cis |
| ENSG00000003400 | CASP10 | protein_coding | chr2:201157478:201158800 | TE | Cis |
| ENSG00000003400 | CASP10 | protein_coding | chr2:201175565:201177049 | TE | Cis |
| ENSG00000003400 | CASP10 | protein_coding | chr2:201190966:201195028 | TE | Cis |
| ENSG00000003400 | CASP10 | protein_coding | chr2:201218567:201225028 | TE | Cis |
| ENSG00000003400 | CASP10 | protein_coding | chr2:201251979:201264163 | SE | Cis |
| ENSG00000003400 | CASP10 | protein_coding | chr2:201342870:201344928 | TE | Cis |
| ENSG00000003400 | CASP10 | protein_coding | chr2:201756907:201757837 | TE | Cis |
| ENSG00000003402 | CFLAR | protein_coding | chr2:200702790:200714518 | TE | Cis |
| ENSG00000003402 | CFLAR | protein_coding | chr2:201049717:201058360 | TE | Cis |
| ENSG00000003402 | CFLAR | protein_coding | chr2:201157478:201158800 | TE | Cis |
| ENSG00000003402 | CFLAR | protein_coding | chr2:201175565:201177049 | TE | Cis |
| ENSG00000003402 | CFLAR | protein_coding | chr2:201190966:201195028 | TE | Cis |
| ENSG00000003402 | CFLAR | protein_coding | chr2:201218567:201225028 | TE | Cis |
| ENSG00000003402 | CFLAR | protein_coding | chr2:201251979:201264163 | SE | Cis |
| ENSG00000003402 | CFLAR | protein_coding | chr2:201342870:201344928 | TE | Cis |
| . | | | | | |
| . | | | | | |
| . | | | | | |
| Tx.4 | Tx.4 | Unannotated | chr1:13966828:13968923 | TE | Cis |
| Tx.4 | Tx.4 | Unannotated | chr1:14003192:14018002 | TE | Cis |
| Tx.4 | Tx.4 | Unannotated | chr1:14035817:14041340 | TE | Cis |
| Tx.4 | Tx.4 | Unannotated | chr1:14110849:14114352 | TE | Cis |
| Tx.4 | Tx.4 | Unannotated | chr1:14174392:14182916 | TE | Cis |
| Tx.4 | Tx.4 | Unannotated | chr1:14323084:14335241 | TE | Cis |
| Tx.4 | Tx.4 | Unannotated | chr1:14360475:14371663 | TE | Cis |
| Tx.4 | Tx.4 | Unannotated | chr1:14824047:14838518 | TE | Cis |
| Tx.4 | Tx.4 | Unannotated | chr1:14876323:14882978 | TE | Cis |
| Tx.4 | Tx.4 | Unannotated | chr1:15258145:15258793 | TE | Cis |
| Tx.4 | Tx.4 | Unannotated | chr1:15297277:15297879 | TE | Cis |
| Tx.4 | Tx.4 | Unannotated | chr1:15361859:15363494 | TE | Cis |

TABLE 5-continued (Partial listing)

| Ensemble Gene ID | Gene Symbol | Gene Type | Enhancer Coordinate | Enh Type | Interaction Type |
|---|---|---|---|---|---|
| Tx.563 | Tx.563 | Unannotated | chr9:21095989:21096500 | TE | Cis |
| Tx.563 | Tx.563 | Unannotated | chr9:21882945:21883700 | TE | Cis |
| Tx.563 | Tx.563 | Unannotated | chr9:21986664:21988334 | TE | Cis |
| Tx.563 | Tx.563 | Unannotated | chr9:22101428:22103439 | TE | Cis |
| Tx.563 | Tx.563 | Unannotated | chr9:22237710:22245533 | TE | Cis |
| Tx.563 | Tx.563 | Unannotated | chr9:28206662:28209011 | TE | Cis |

The network of the Chromosome 1 in MM.1S cell was built based on RNA-chromatin interactions of all the hit genes in the chromosome at a very stringent significance (z≥3); and the network of the whole genome was based on significant RNA-chromatin interactions from protein-coding genes with slightly reduced stringency (z≥2). The network was then imported into Cytoscape (version 3.3), software which is very versatile for determining, analyzing and visualizing networks, including the use of a self-organized layout algorithm and Edge-Repulsive Spring-Electric Layout. Moreover, Cytoscape is further supported by the third-party app of AllegroLayout.

Functional perturbation of general enhancer activities. MDA-MB-231 cells were treated with the BRD4 inhibitor JQ1 or DMSO for 6 h, and immediately harvested for global nuclear run-on. To quantify transcription activities in an unbiased manner, GRO-seq read densities were initially normalized using total uniquely-mapped read numbers to remove variations between libraries. To minimize the bias introduced by promoter pausing or gene length, only reads that were aligned within the 2 Kb region 1 Kb downstream from the TSS were selected to calculate the transcription activity. For multi-isoform genes, the transcript with highest read counts within the 2 Kb window was selected to represent the gene's transcription activity. Public datasets analyzed. The data of RNA Pol II ChIP-seq for MDA-MB-231 cells were obtained from European Genome-phenome Archive (www.ebi.ac.uk/ega). All other datasets were obtained from NCBI Gene Expression Omnibus (www.ncbi.nlm.nih.gov/geo/) (see Table 6):

TABLE 6

| Data type | Cell type | Accession ID |
|---|---|---|
| roX2 ChIRP-seq | Drosophila S2 | GSM820427, GSM820428 |
| roX2 ChART-seq | Drosophila S2 | GSM833475, GSM833476 |
| MLS3-TAP ChIP-seq | Drosophila Clone 8 | GSM296247 |
| Total RNA-seq | Drosophila S2 | GSM480160 |
| Total RNA-seq | Human MDA-MB-231 | GSM929913 |
| H3K27ac ChIP-seq | Human MDA-MB-231 | GSM1204474, GSM1204475 |
| H3K4me3 ChIP-seq | Human MDA-MB-231 | GSM1204472, GSM1204473 |
| RNA Pol II ChIP-seq | Human MDA-MB-231 | EGAN00001343502, EGAN00001343503 |
| H3K27me3 ChIP-seq | Human MDA-MB-231 | GSM2058911, GSM2058912 |
| RNA expression array | Human MM.1S (DMSO, 6 h) | GSM1094100, GSM1094101 |
| RNA expression array | Human MM.1S (JQ1, 0.5 mM, 6 h) | GSM1094092, GSM1094093 |
| H3K27ac ChIP-seq | Human MM.1S | GSM894083 |
| RNA Pol II ChIP-seq | Human MM.1S | GSM894086 |
| H3K4me3 ChIP-seq | Human MM.1S | GSM894084 |
| H3K27me3 ChIP-seq | Human MM.1S | GSM1252088 |

TABLE 6-continued

| Data type | Cell type | Accession ID |
|---|---|---|
| Brd4 ChIP-seq | Human MM.1S (DMSO, 6 h) | GSM1038275 |
| Brd4 ChIP-seq | Human MM.1S (JQ1, 0.5 mM, 6 h) | GSM1038271 |

Figure 2A:
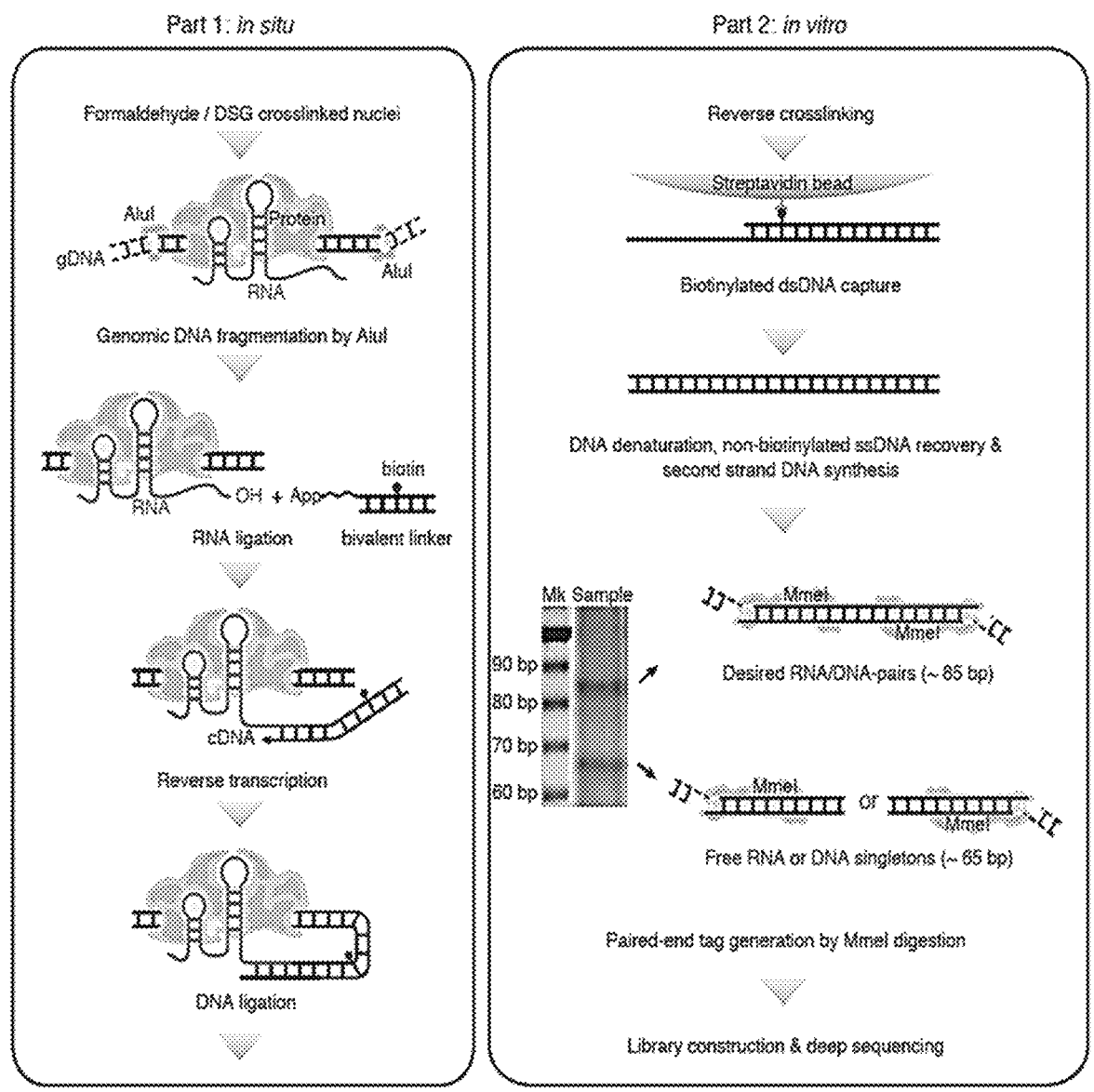
FIG. 2A-E shows chromatin-interacting RNAs revealed by GRID-seq. (A) Schematic presentation of the GRID-seq technology. Left: steps performed in situ on isolated nuclei; Right: steps performed in solution. The two major bands resolved by native polyacrylamide gel correspond to the products of the linker ligated to both DNA and RNA (upper band) or to either DNA or RNA (lower band). After native gel resolution, the excised upper band was subjected to library construction by adapter ligation followed by deep sequencing. (B) Top: Scheme for using "human" MDA-MB-231 cells, "*Drosophila*" S2 cells, or the mix of both for GRID-seq library construction. Bottom: The percentages of human RNAs ligated to human DNAs or *Drosophila* DNAs and the percentages of *Drosophila* RNAs ligated to *Drosophila* DNAs or human DNAs. (C) Genes rank-ordered by GRID-seq RNA reads in MDAMB-231 cells. Dark-grey-labeled are genes that passed the cutoff based on the amounts of the chromatin-interacting RNAs. (D) Scatterplot of length-normalized RNA reads from annotated gene (y-axis) and the read density of the largest peak on DNA (x-axis) in MDA-MB-231 cells. RPK: reads per Kb. Dashed lines are the set thresholds for specific hits with dots for long RNAs and small RNAs. Dots within the box are chromatin-interacting RNAs without sufficient density. (E) Comparison between gene expression detected by RNA-seq (based on the data from GSM929913) and chromatin-interacting RNAs detected by GRID-seq for all human genes in MDA-MB-231 cells. Light grey dots are genes not showing frequently interactions with DNA as in (C) and darker grey colored genes correspond to those in (D). Highlighted are one or two representative genes in each class. RPKM: reads per Kb per million mapped reads.

Ligating RNA to proximal DNA in situ. A triple negative breast cancer MDA-MB-231 cell line was chosen to develop a global and unbiased strategy to map RNA-chromatin interactions. To stabilize RNAs on chromatin, cells were fixed with disuccinimidyl glutarate (DSG) and formaldehyde. Nuclei were isolated, and digested in situ with a frequent cutter (AluI). A biotin-labeled bivalent linker comprising of an ssRNA portion for ligation only to RNA and a dsDNA portion for ligation only to DNA (See FIG. 2A). As shown in FIG. 2A, part 1, RNA ligation was first performed in situ, that was then followed by washing away excess free linkers. Ligated RNA was made by extending the DNA primer on the linker with reverse transcriptase. The linker was then ligated to local genomic DNA, followed by affinity purification with streptavidin beads. As shown in FIG. 2A, part 2, ssDNA was released from beads, converted to dsDNA, and then a type II restriction enzyme MmeI was uxed to cut DNA ~20 nt upstream and downstream from the two built-in recognition sites in the linker. The products were resolved in native gel to detect two defined DNA fragments with the larger one (~85 bp) corresponding to linker ligation product that is linked to both RNA and DNA and the smaller linker ligation product (~65 bp) that is linked either to RNA or DNA. The larger fragment was isolated for amplification and adapter ligation for deep sequencing. Typically, >200 million were generated with 100 nt raw reads (~40 million uniquely mapped read mates) per library on human cells, which showed high concordance between replicates ($R^2$>0.95, see FIGS. 1B and C).

Figure 2B:
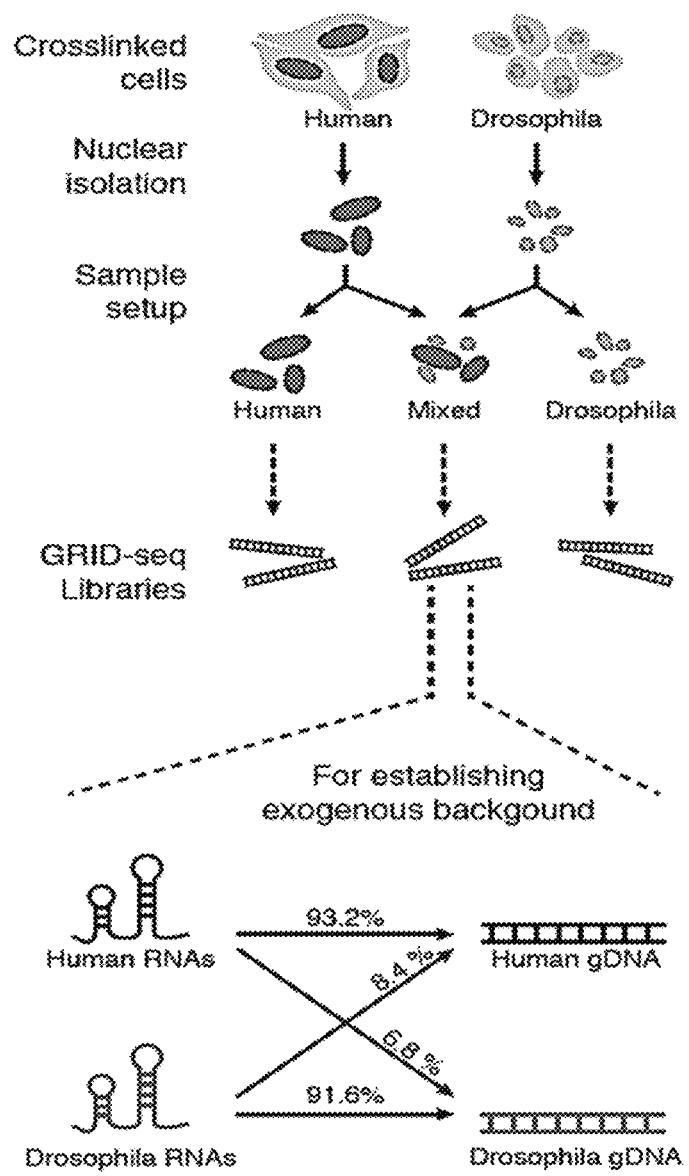

A strategy was developed for controlling non-specific interactions by mixing isolated nuclei from MDA-MB-231 cells and Drosophila S2 cells (see FIG. 2B). As the human genome is much larger than the Drosophila genome, genomes from human and Drosophila cells were mixed together in roughly equal molar amounts. By using uniquely and unambiguously mapped RNA and DNA read mates to human or to Drosophila genome, it was estimated that 6.8% of human RNA linked to Drosophila DNA and 8.4% Drosophila RNA was linked to human DNA (see FIG. 1B). While the cross-species mates likely resulted from ligation of fragmented RNAs that had randomly landed on exposed chromatin during the GRID-seq reaction, the majority of RNA-chromatin interactions which were detected reflected in situ interactions in both human and Drosophila genomes. In fact, such non-specific cross-genome interactions enabled the construction of a general background, which is important for inferring specific RNA-chromatin interactions within each genome.

Figure 2C:
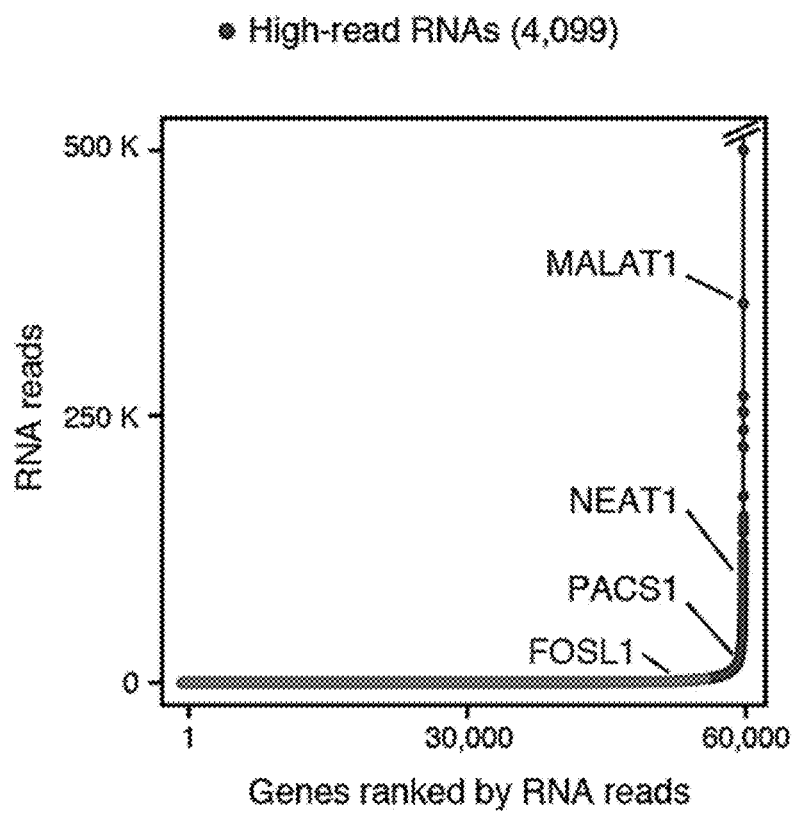
Figure 2D:
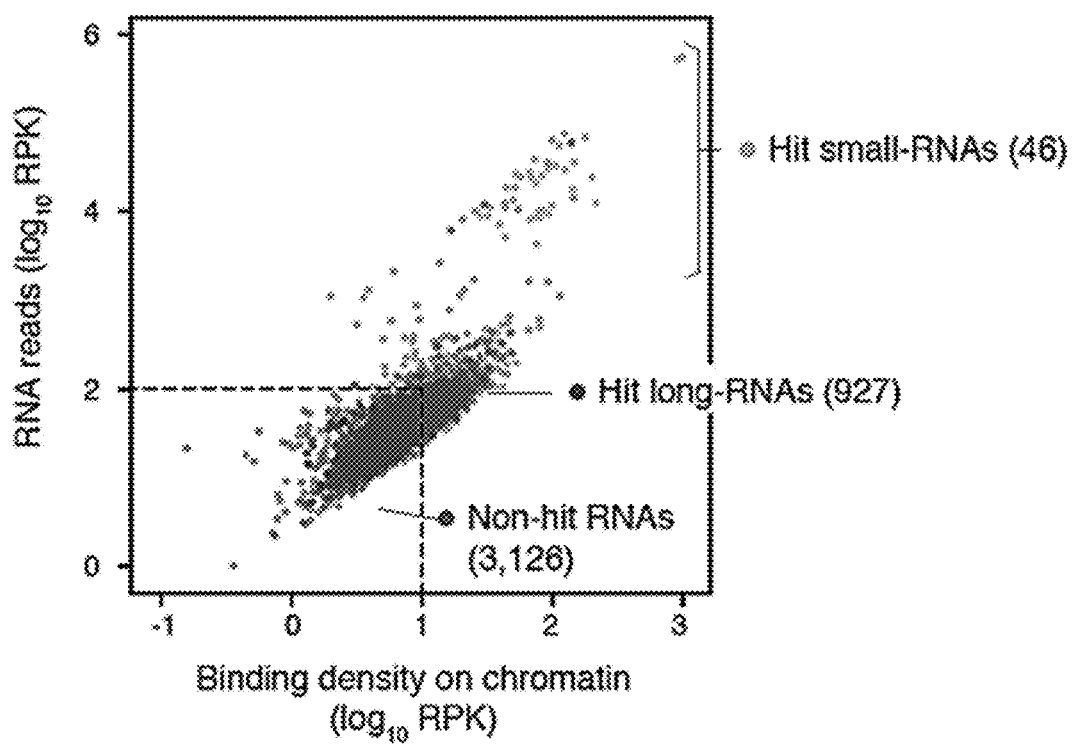
Figure 2E:
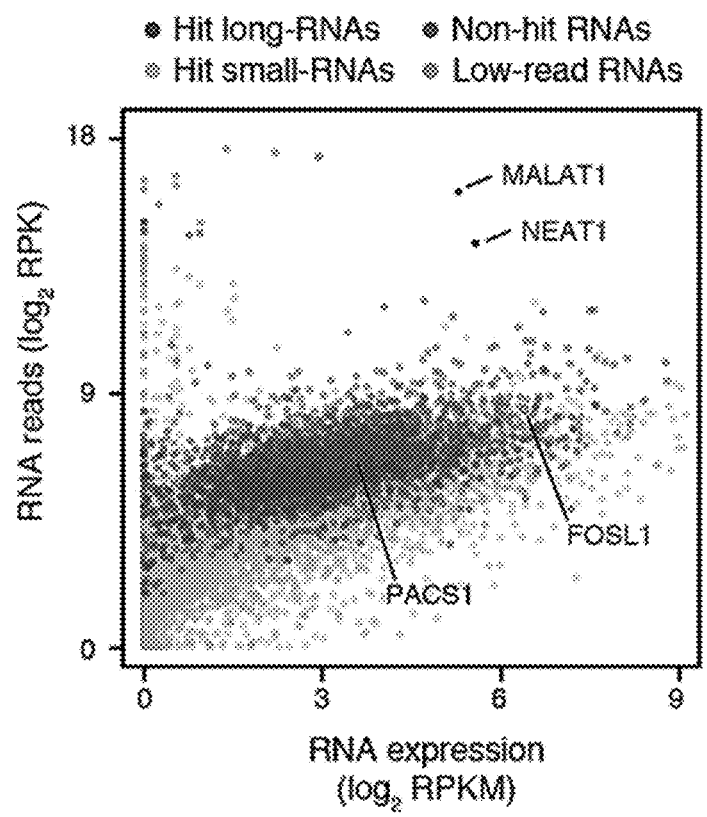
Figure 3A:
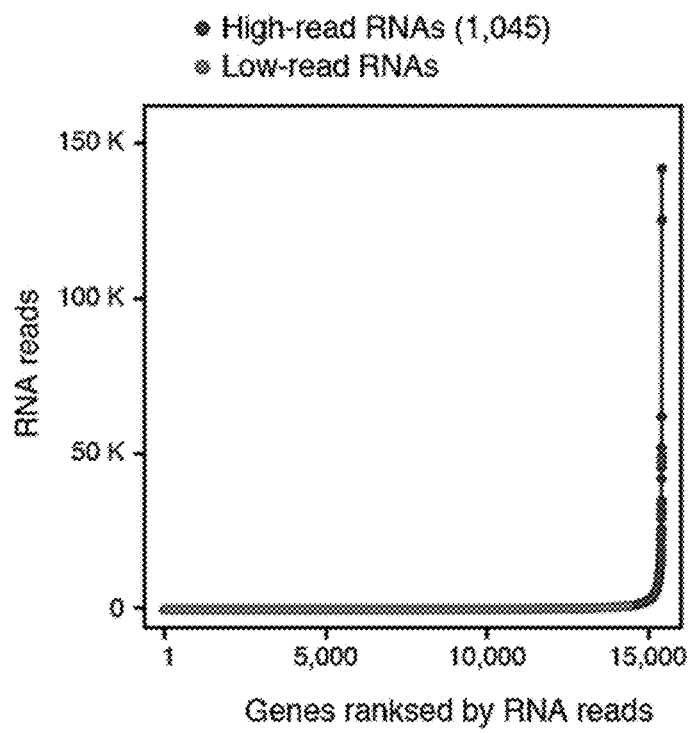
FIG. 3A-E provides examples of RNAs detected by GRID-seq in *Drosophila* S2 cells. (A) *Drosophila* genes rank-ordered by GRID-seq RNA reads in S2 cells. Dark-grey-labeled are genes that passed the inflection. (B) Top: Percentages of genes that gave to GRID-seq RNA reads in different classes. Bottom: The distribution of GRID-seq detected RNAs along the gene body in MDA-MB-231 cells. Small RNAs were excluded from this analysis due to their short gene body. (C) Scatterplot of length-normalized RNA reads from each annotated gene (y-axis) and the read density of the largest RNA peak on DNA (x-axis) in *Drosophila* S2 cells. RPK: read per Kb. Dashed lines are the set thresholds for specific hits with red dots for long RNAs and orange dots for small RNAs. (D) Comparison between gene expression detected by RNA-seq (GSM480160) and chromatin-interacting RNAs detected by GRID-seq for all expressed genes in *Drosophila* S2 cells. Light grey dots are genes not showing frequently interactions with DNA as in (A), and darker-grey genes correspond to those in (C). (E) Visualization of GRID-seq RNA reads in two scales (first two tracks) in comparison with RNA-seq reads (third track) on human Chromosome 11 in MDAMB-231 cells. Left-side highlighted are hit RNAs from the two long non-coding RNA genes NEAT1 and MALAT1. Right-side highlighted are non-hit RNAs from protein-coding FOSL1 and PACS1 genes. Light grey indicates collective reads from all other non-hit RNAs in this region (fifth track). Note that FOSL1 was expressed at a higher level than NEAT1 and MALAT1 based on the RNAseq data (third track), indicating that hit RNAs are not necessarily from highly expressed genes. Boxed regions are enlarged in bottom panels to further show the GRID-seq detected RNA signals of hit RNA of MALAT1 and non-hit RNA of PACS1 on DNA in comparison with gene expression.
Figure 3B:
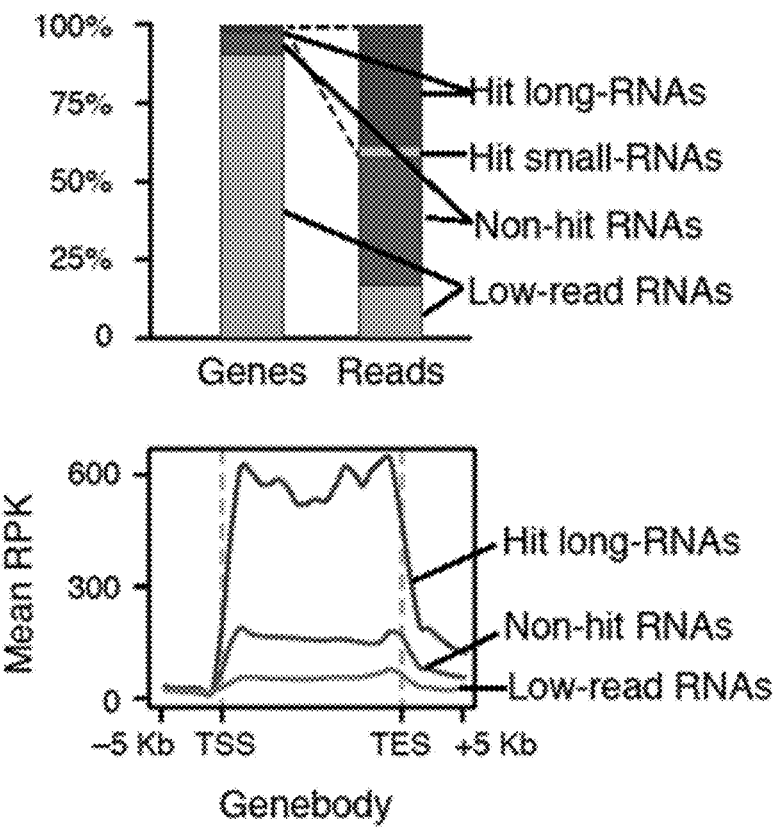
Figure 3C:
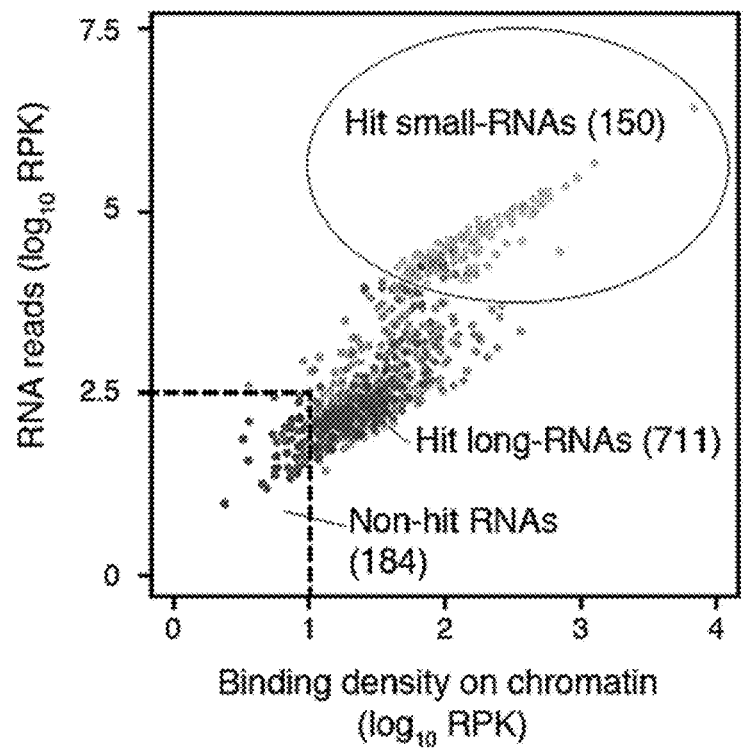
Figure 3D:
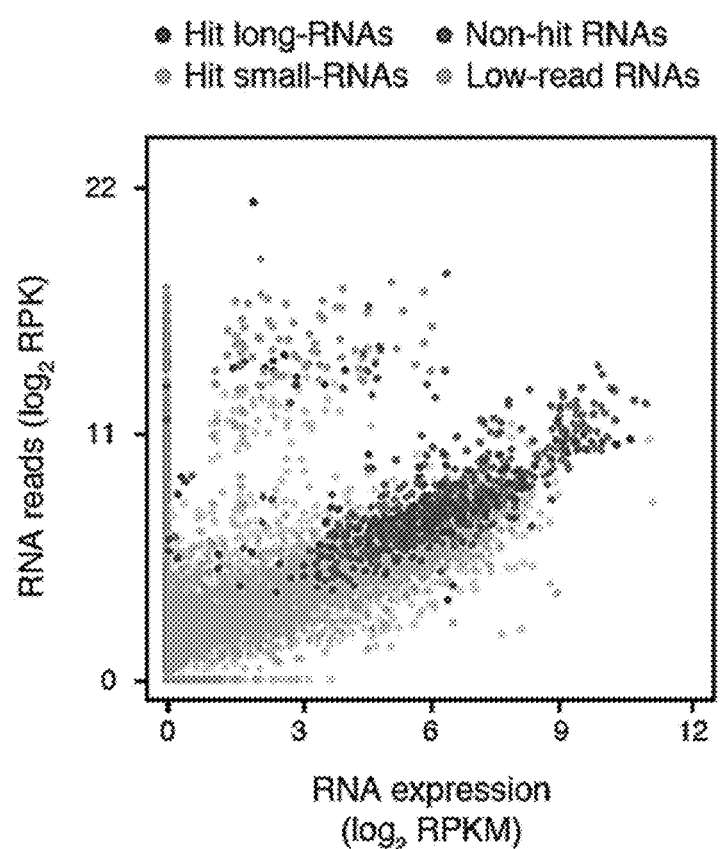
Figure 3E:
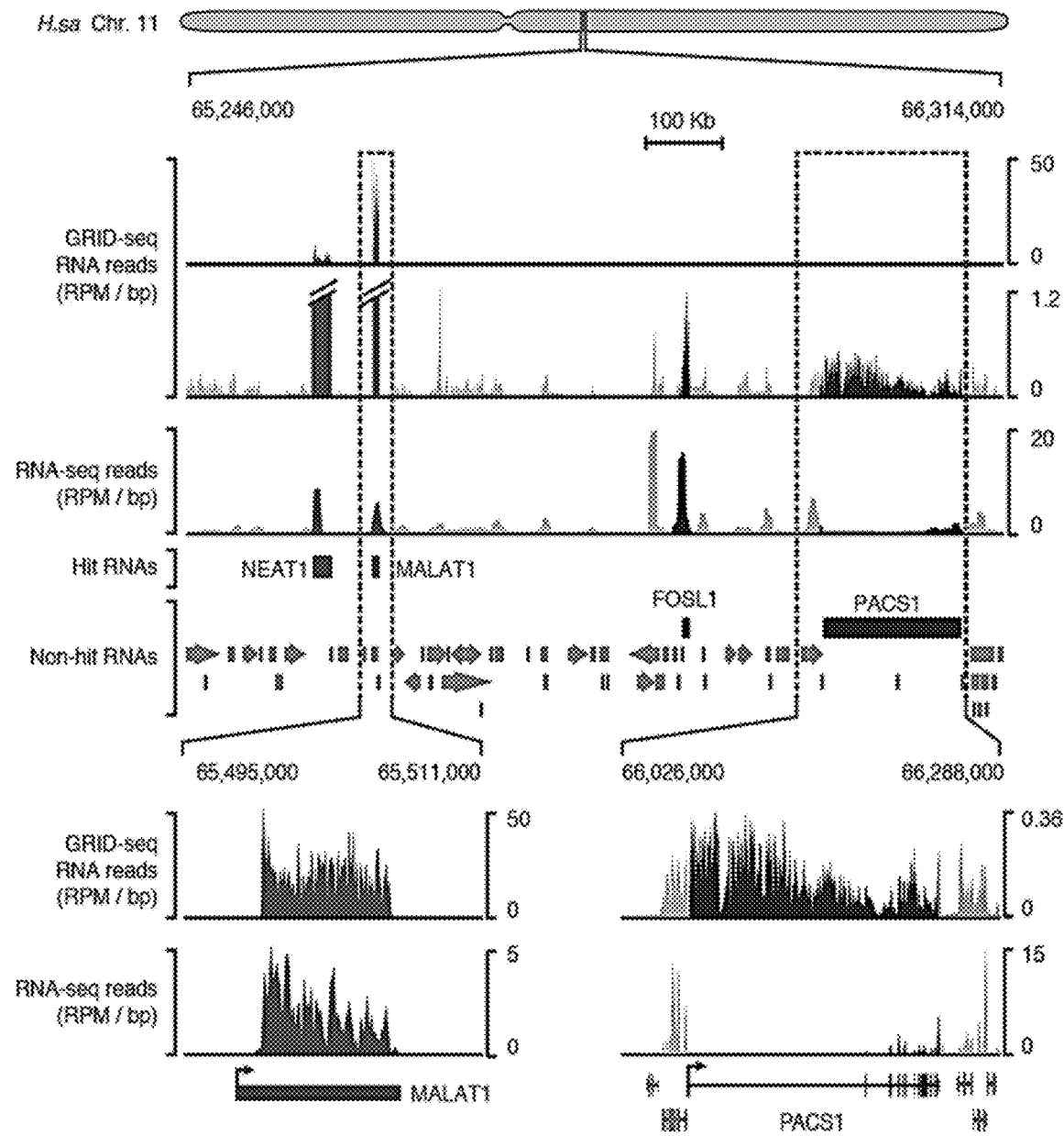

Identifying hit RNAs on chromatin. Based on RNA reads on chromatin genes were rank ordered. A set of RNAs were observed, including both known lncRNAs and various pre-mRNAs, that prevalently interacted with chromatin in both human and *Drosophila* genomes (red-labeled in see FIG. 2C and FIG. 3A). These chromatin-interacting RNAs are expressed for only a small fraction of active genes, with RNA reads being evenly derived from gene bodies. These RNAs account for ~90% of all detected RNAs on chromatin (see FIG. 3B). Close examination of the results revealed that many RNAs showed discrete binding while others exhibited relatively scattered distribution on chromatin. Therefore, length-normalized abundance of RNAs were plotted against their highest binding density on chromatin to identify RNAs with sufficient densities in both RNA reads and interactions on chromatin, leading to 973 "hit" RNAs in MDA-MB-231 cells (see Table 2). These hit RNAs comprise both small RNAs (2.1%, which predominantly correspond to snRNAs and snoRNAs, orange-labeled in FIG. 2D and FIG. 3C) and long RNAs (including 6.7% lncRNAs and 87.1% protein-coding pre-mRNAs, red-labeled in FIG. 2D, and FIG. 3C). When compared with gene expression, it becomes evident that hit RNAs are not necessarily from highly expressed genes in both human and *Drosophila* cells (see FIG. 2E, and FIGS. 3D and E). Instead, the data revealed a set of RNAs with propensity to frequently and specifically interact with chromatin in human and *Drosophila* genomes.

Figure 4A:
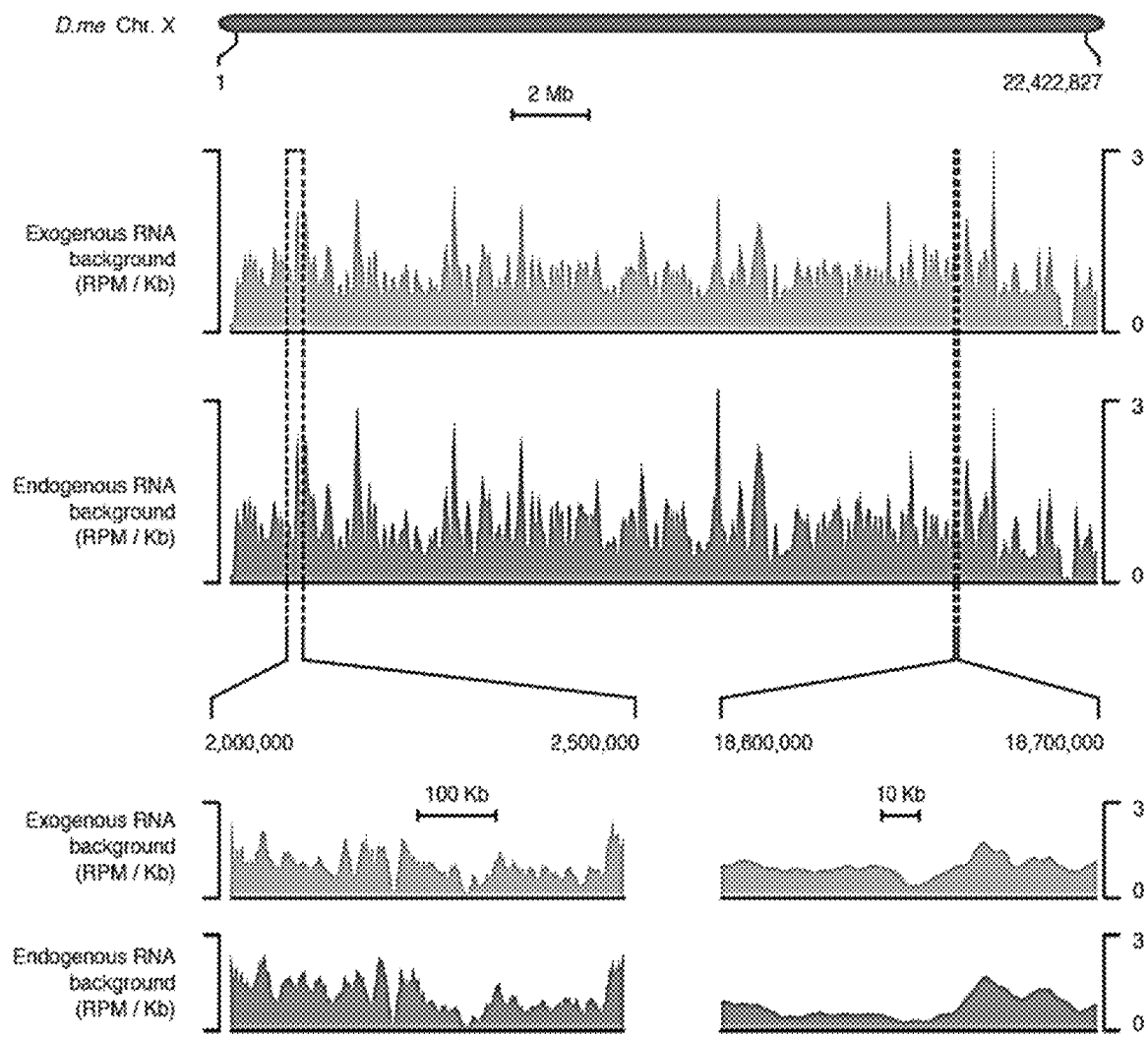
FIG. 4A-C demonstrates the background established with exogenous or endogenous RNAs. (A) Background deduced with exogenous or endogenous RNAs on *Drosophila* Chromosome X. Top two tracks: The distribution of human RNAs linked to *Drosophila* DNA, which represents the true background (Light Grey), and the distribution of collective endogenous *Drosophila* transchromosomal interacting RNAs from all protein-coding genes, which corresponds to the deduced background (dark grey). Two representative genomic regions were enlarged in the bottom tracks. y axis indicates RNA reads per million. (B) Comparison between exogenous and endogenous background RNA densities on the 1 Kb-binned *Drosophila* genome. (C) Comparison between the deduced backgrounds based on endogenous RNAs from two independent GRIP-seq experiments on human MDA-MB-231 cells. RPK: reads per Kb.
Figure 4B:
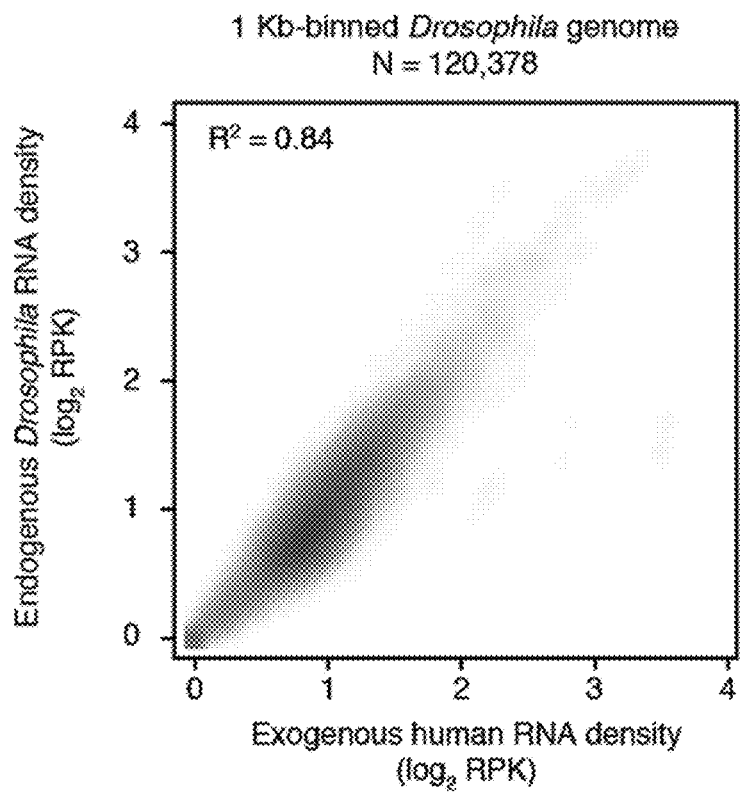
Figure 4C:
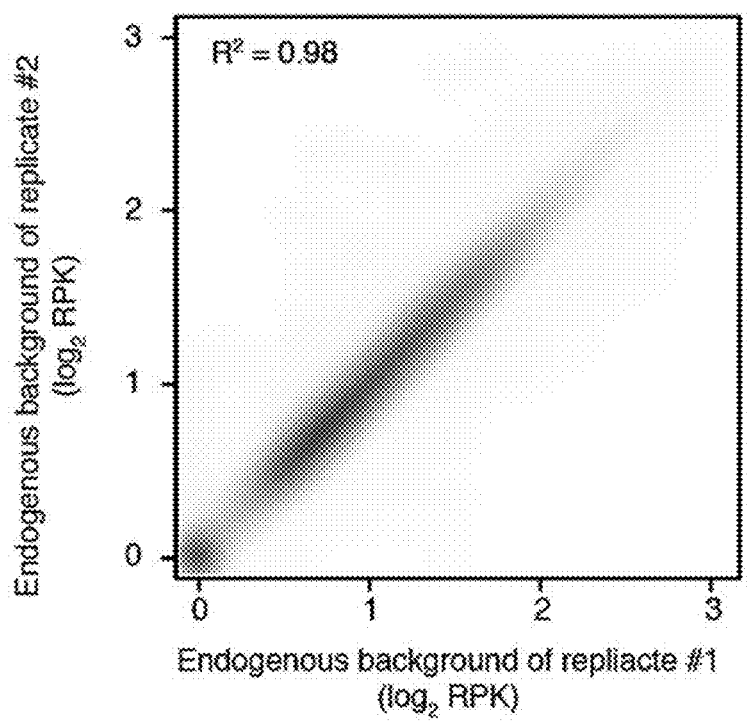

It was found that a sufficient density of human RNAs could be linked to the small *Drosophila* genome, generating a background that could be utilized for non-specific RNA-chromatin interactions. Besides randomly fragmented RNAs, expressed RNAs are also known to extensively explore nuclear space after being released from their sites of transcription. It was reasoned that trans-chromosomal signals from pre-mRNAs of protein-coding genes might be used to construct a background. Indeed, the background deduced from endogenous RNAs in *Drosophila* S2 cells is highly concordant with backgrounds generated from trans-species RNA-chromatin interactions (see FIGS. 4A and B). The results demonstrate that endogenous RNAs can be used to build similar backgrounds for human cells, which was reproducible based on replicated GRID-seq datasets (see FIG. 4C). GRID-seq signals that are significantly above the background reflect RNAs that either traveled extensively to engage in specific trans-chromosomal interactions or interacted with chromatin in spatial proximity to their sites of transcription.

Figure 5A:
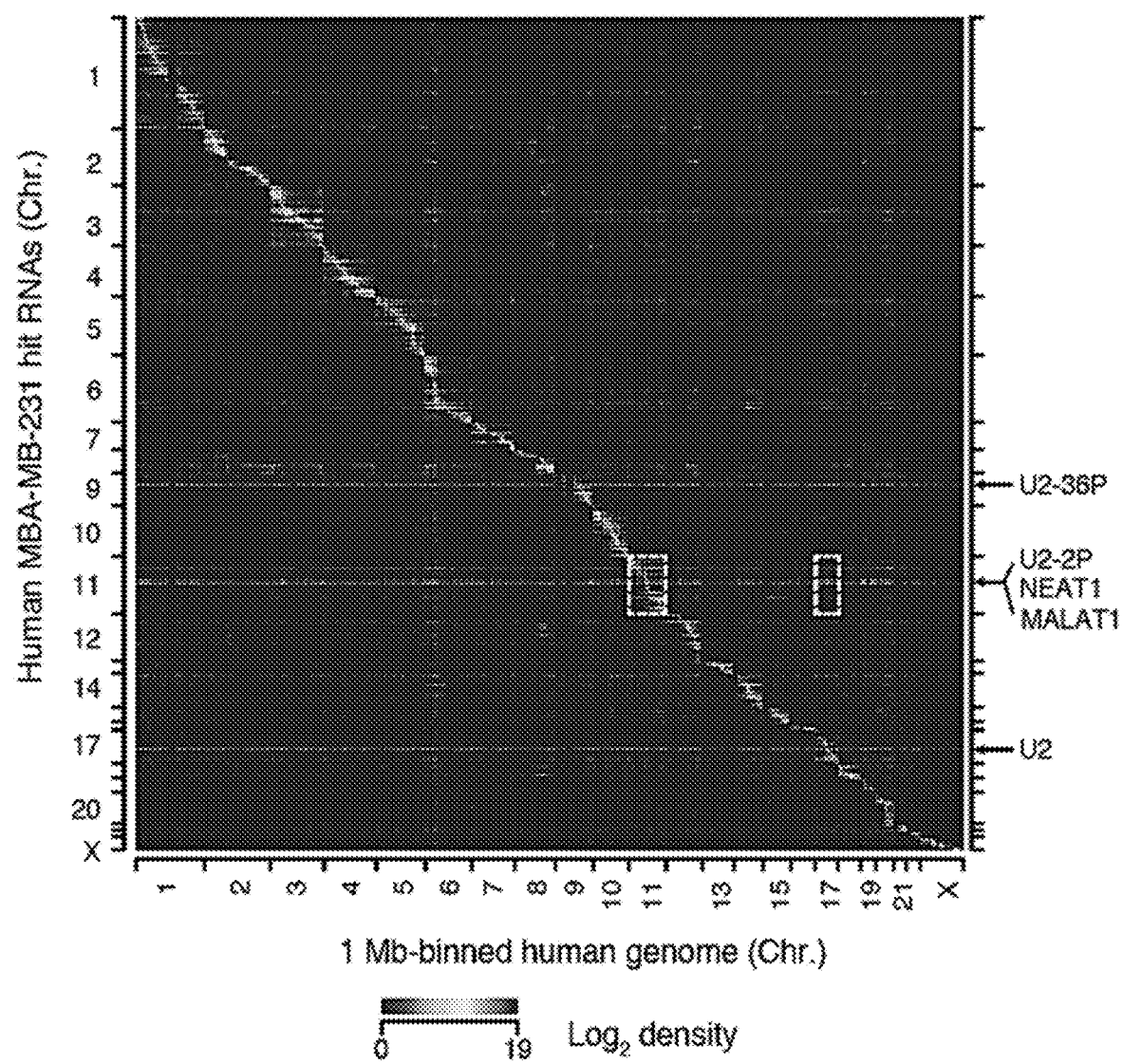
FIG. 5A-F presents a global view of RNA-chromatin interactions in human MDA-MB-231 cells. (A) A heatmap showing the interaction of all hit RNAs across the whole human genome in MDAMB-231 cells. Row: hit RNAs from their origins of transcription. Column: hit RNAs linked to DNA in the 1 Mb-binned human genome. Representative trans-chromosomal interacting hit RNAs are labeled on the right. U2-36P and U2-2P are transcripts from pseudo U2 snRNA genes. (B) Two representative regions boxed in (A) are enlarged, showing detailed interaction patterns of hit RNAs from Chromosome 11 on 100 Kb-binned Chromosome 11 (left) and Chromosome 17 (right). Representative hit RNAs are labeled on the left (pc: protein-coding RNAs, nc: noncoding RNAs). Top: The background deduced from endogenous trans-chromosomal interacting RNAs from all protein-coding genes. (C) Ternary plot of non-coding hit RNAs based on the relative chromatin-interaction levels in local (±1 Kb from their genes), cis (the same chromosome the gene resides except local), and trans (all other chromosomes except its own chromosome) modes. Grey-scale of dots represent different types of RNAs and sizes represent the levels of chromatin-interacting RNAs. (D) Circos plots of the interactions of two non-coding hit RNAs MALAT1 (left) and PVT1 (right) with chromatin in the human genome. (E) Ternary plot of protein-coding hit RNAs shown similarly as in (C). (F) Circos plots of the interactions of two protein-coding hit RNAs HMGA2 (left) and SMAD5 (right) with chromatin in the human genome.
Figure 5B:
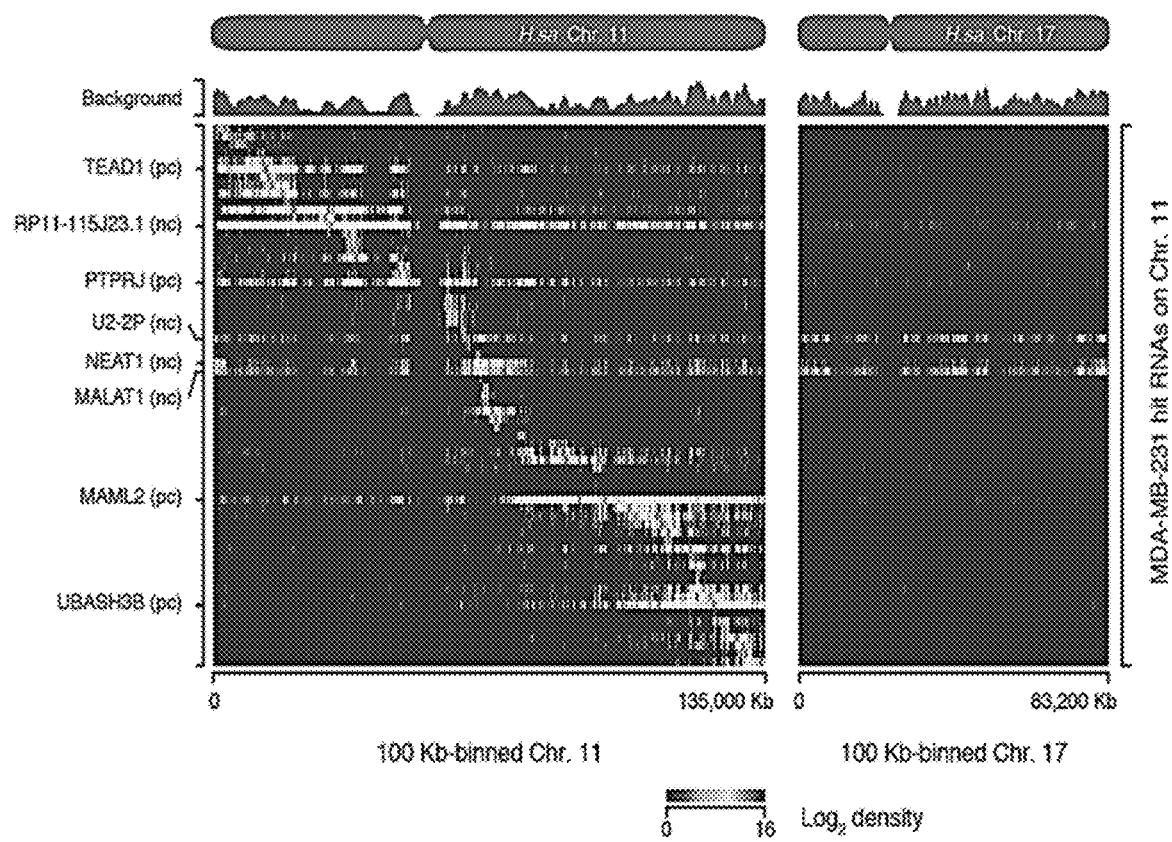
Figure 6A:
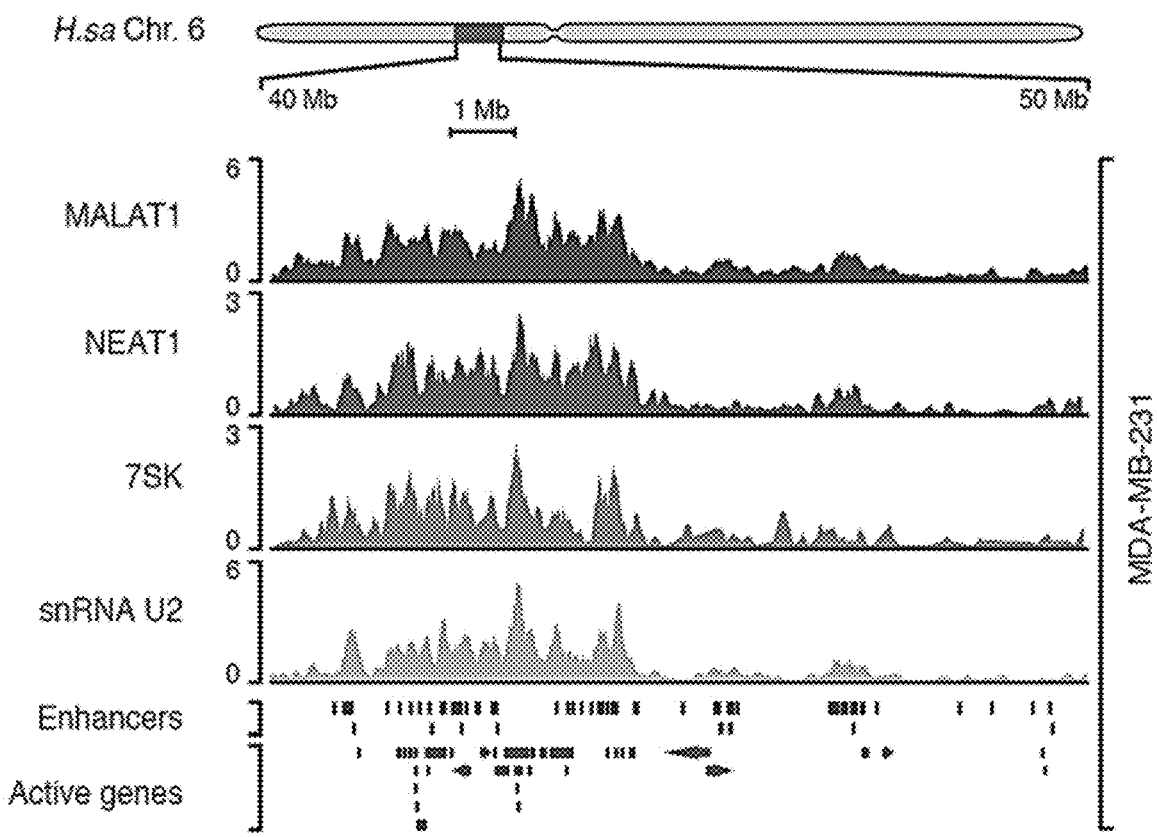
FIG. 6A-B provides examples of hit RNA signals relative to the background. (A) Four major trans-chromosomal hit RNAs mapped to a representative region on human Chromosome 6 in MDA-MB-231 cells. y-axis indicates reads per million for each RNA. Active enhancers and genes in the region are also shown for comparison. (B) The background deduced from endogenous trans-chromosomal interacting RNAs from all protein-coding genes in comparison with the enhancer mark H3K27ac, RNA Pol II binding, and active enhancers and promoters in MDA-MB-231 (top panel) or MM.1S (bottom panel) cells on a representative region of human Chromosome 9. These data indicate that the general background for RNA chromatin interactions tends to occur on open chromatin regions.
Figure 6B:
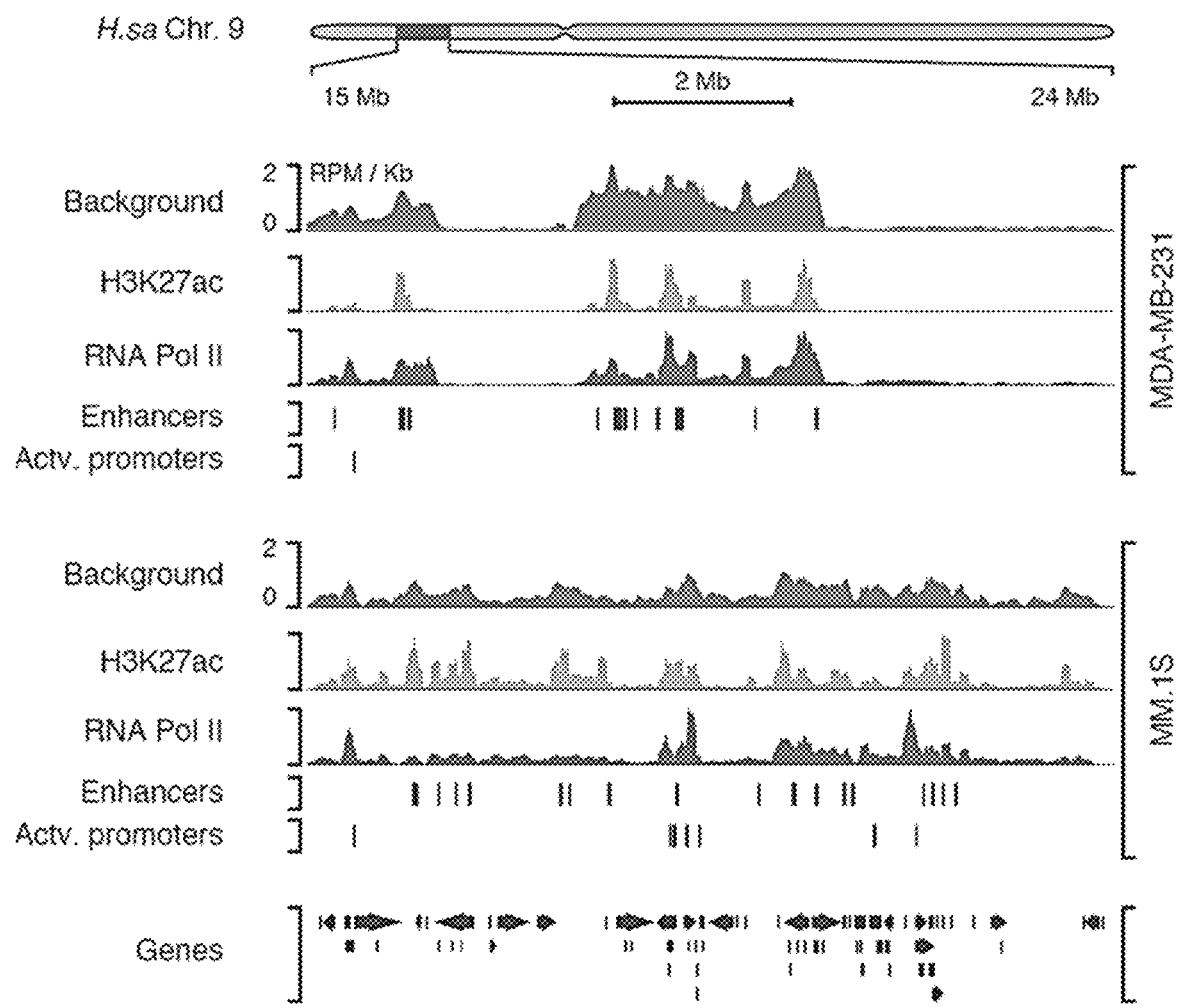
Figure 7A:
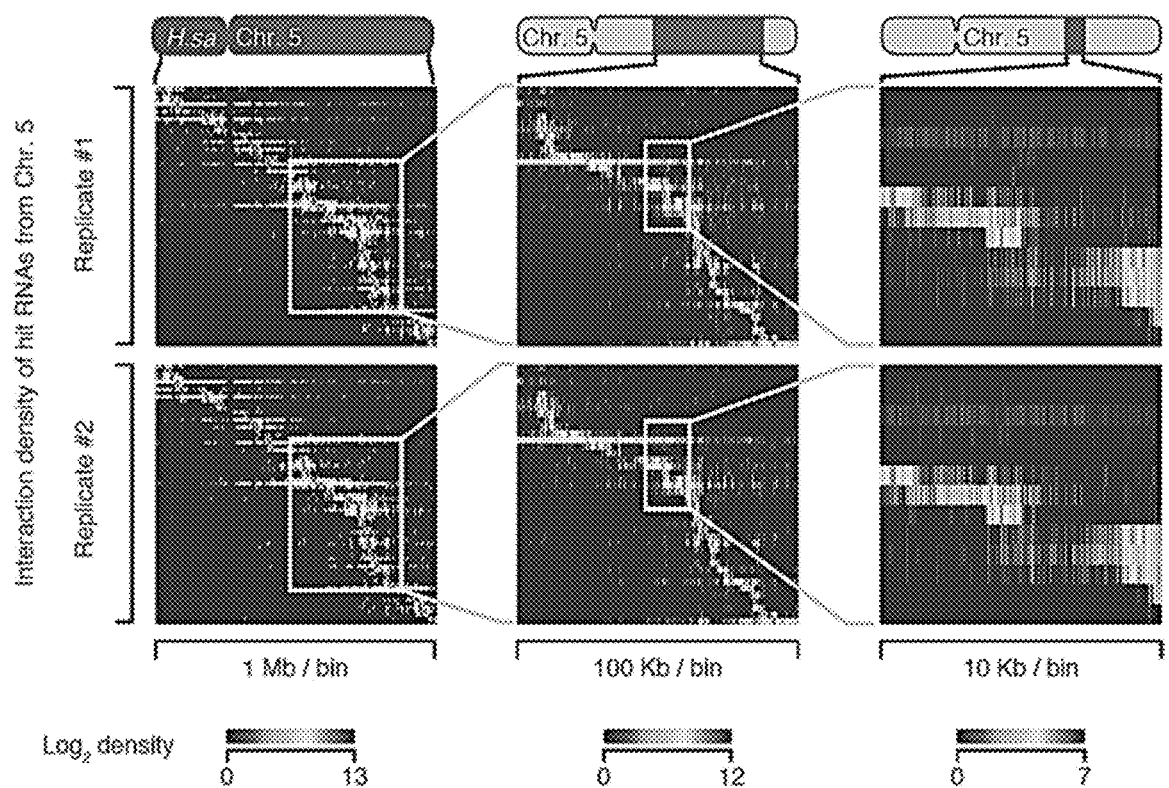
FIG. 7A-B presents gradually expanded views of RNA-chromatin interactions. (A) RNA-chromatin interaction heatmaps on Chromosome 5 constructed from two independent GRID-seq experiments on MDA-MB-231 cells. Boxed regions in each panel were enlarged with increasing resolution in the next panel on the right. (B) Correlation of RNA read densities at increasing resolution (decreasing bin size) based on total hit RNAs across the human genome between the replicates performed on MDA-MB-231 cells.
Figure 7B:
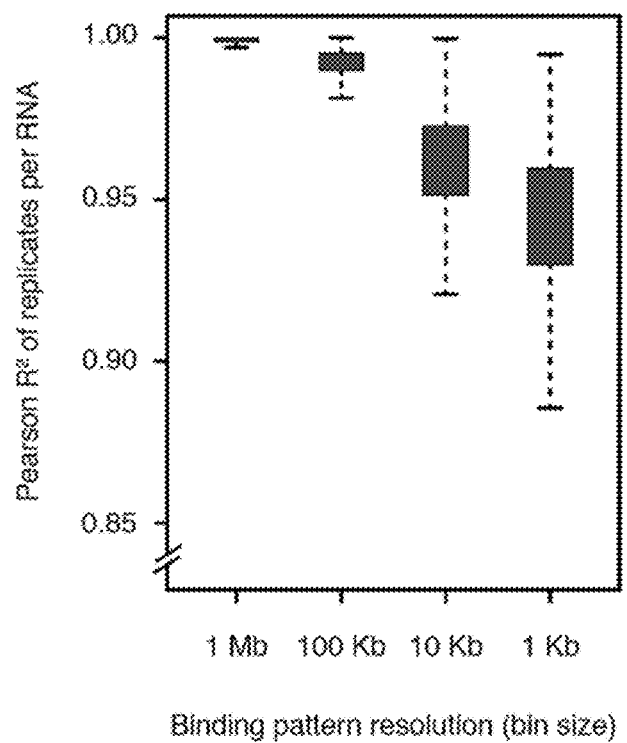

Global view of RNA-chromatin interactions. When displaying all hit RNAs on chromosomes in the human genome after normalization against the background, it was clear that the majority of the RNAs interacted with chromatin near their sites of transcription, and surprisingly, a limited number of RNAs were extensively engaged in trans-chromosomal interactions, such as U2 snRNA and two pseudo U2 snRNAs, MALAT1 and NEAT1 (see FIG. 5A). Both MALAT1 and NEAT1 reside in Chromosome 11. An enlarged view of chromosomes 11 and 17 demonstrated that prevalent MALAT1 and NEAT1 interactions had similar efficiencies with other chromosomes in the human genome. Further analysis revealed their general preference for active chromatin regions, such as promoters marked by H3K4me3 and active enhancers decorated with H3K27ac (see FIG. 6A). Moreover, 7SK RNA was found to be abundant on chromatin (see FIG. 6A), similar to the signals detected by ChIRP, but its interactions with chromatin in most locations were similar to background (see FIG. 5A). The background RNA-chromatin interactions also tended to be associated with open chromatin (see FIG. 6B). Using an expanded chromosomal view, multiple coding (pc) and non-coding (nc) RNAs were noted as being capable of interacting with numerous loci in the same chromosomes (see FIG. 5B), suggesting that these RNAs may help define (as either cause or consequence) nuclear territories in the cell. Such extensive RNA interactions with chromatin are highly reproducible based on replicated GRID-seq experiments, even with increasing resolutions (se FIGS. 7A and B).

Figure 8A:
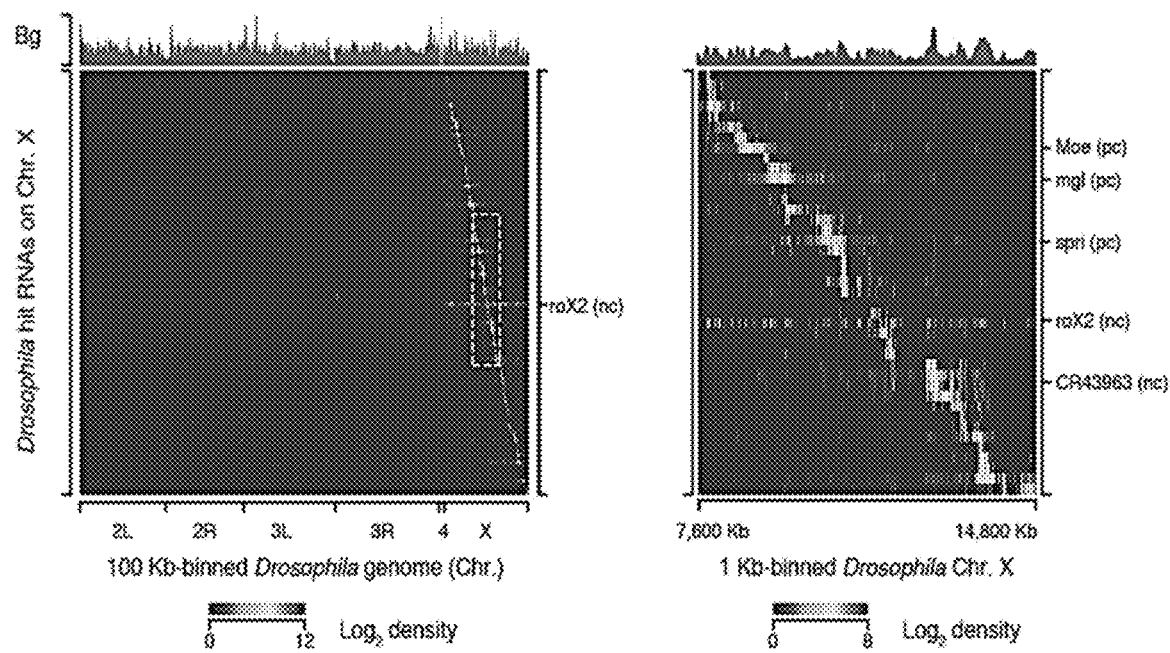
FIG. 8A-C presents a roX2 RNA-chromatin interaction map in *Drosophila* S2 cells. (A) A heatmap showing the interaction of hit RNAs from Chromosome X across the whole *Drosophila* genome. Row: hit RNAs from their origins of transcription. Column: hit RNAs linked to DNA in the 100 Kb-binned *Drosophila* genome. Top: The background (Bg) deduced from endogenous trans-chromosomal interacting RNAs. Right is an enlarged view of the boxed region in panel (A) showing decoration of roX2 RNA on Chromosome X in S2 cells. Labeled on the right are representative non-coding hit RNAs (nc) and protein-coding hit RNAs (pc). (B) A representative region of *Drosophila* Chromosome X, illustrating the interactions of roX2 RNA with chromatin detected by ChIRP (first track) or ChART (second track) in comparison with GRID-seq signals or with the ChIP-seq signals for the TAP-tagged roX2 binding protein MSL3. (C) Meta-analysis of roX2 chromatin-interacting signals detected by ChIRP (from GSM820427 and GSM820428), ChART (from GSM833475 and GSM833476) and GRID-seq relative to MSL3-TAP ChIP-seq peaks (from GSM296247).
Figure 8B:
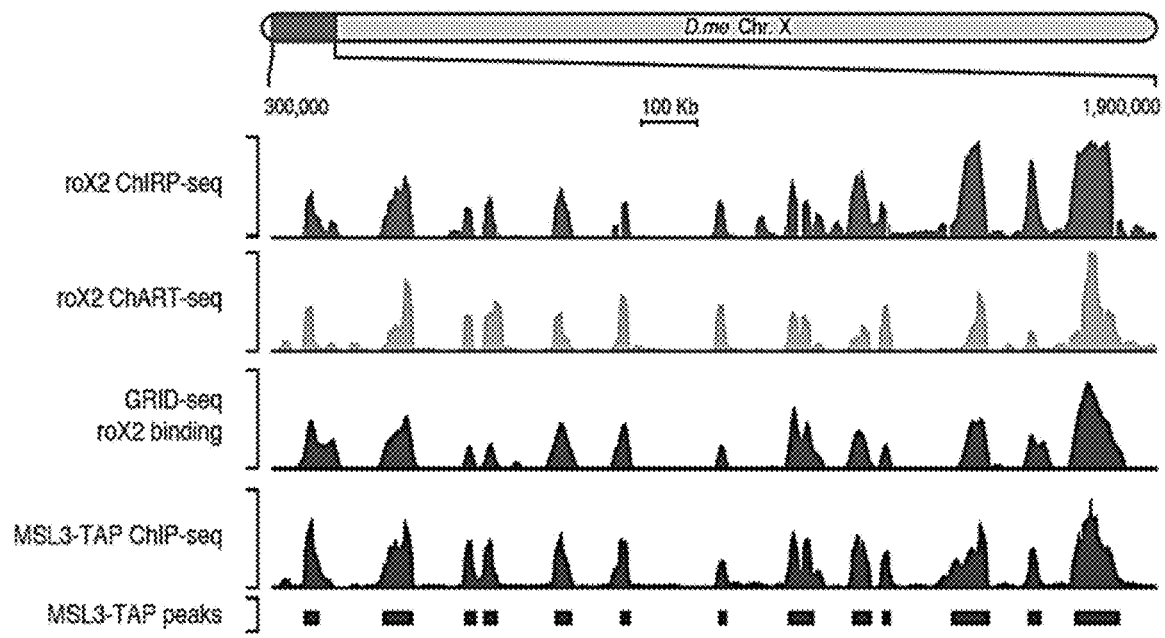
Figure 8C:
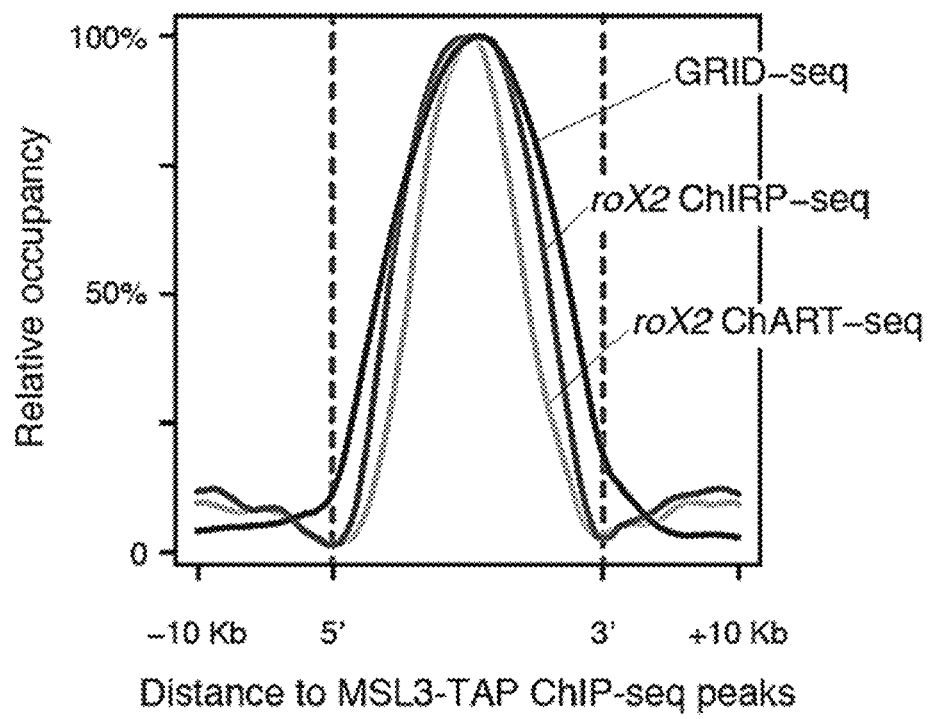
Figure 9A:
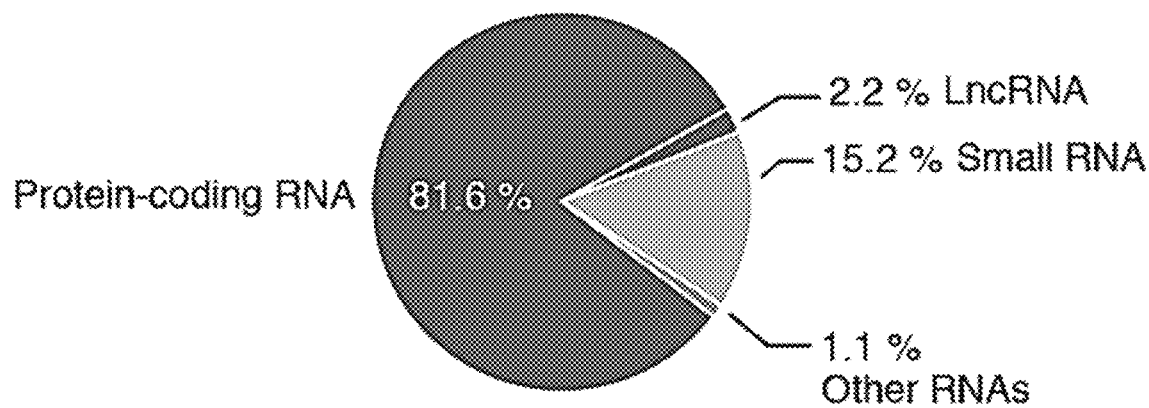
FIG. 9A-E presents patterns of RNA-chromatin interactions in *Drosophila* S2 cells. (A) Relative representations of different hit RNA types in *Drosophila* S2 cells. (B) Ternary plot of non-coding hit RNAs based their relative interactions in local (±1 Kb from their genes), cis (the same chromosome the gene resides except local), and trans (all other chromosomes except its own chromosome) modes. Colors of dots represent different types of RNAs and sizes represent the levels of chromatin-interacting RNAs. (C) Ternary plot of protein-coding hit RNAs as similarly analyzed in (B). (D) Circos plots of chromatin interactions of non-coding hit RNAs CR43334 (left), U5-63BC snRNA (middle) and roX2 (right) in the *Drosophila* genome. (E) Circos plots of chromatin interactions of protein-coding hit RNAs Mi-2 (left) and pnt (right) in the *Drosophila* genome.
Figure 9B:
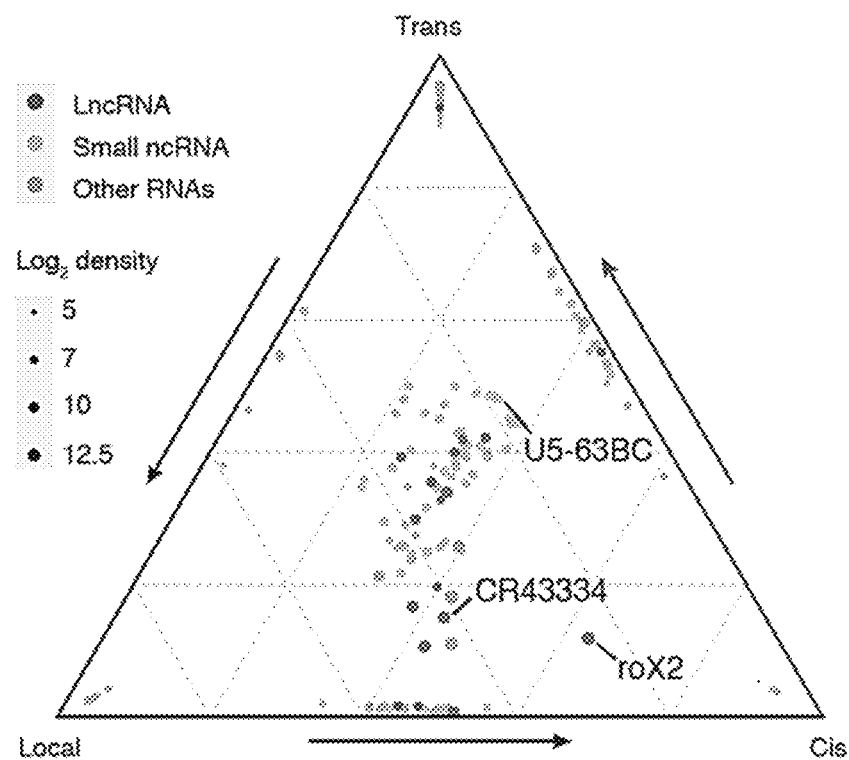
Figure 9C:
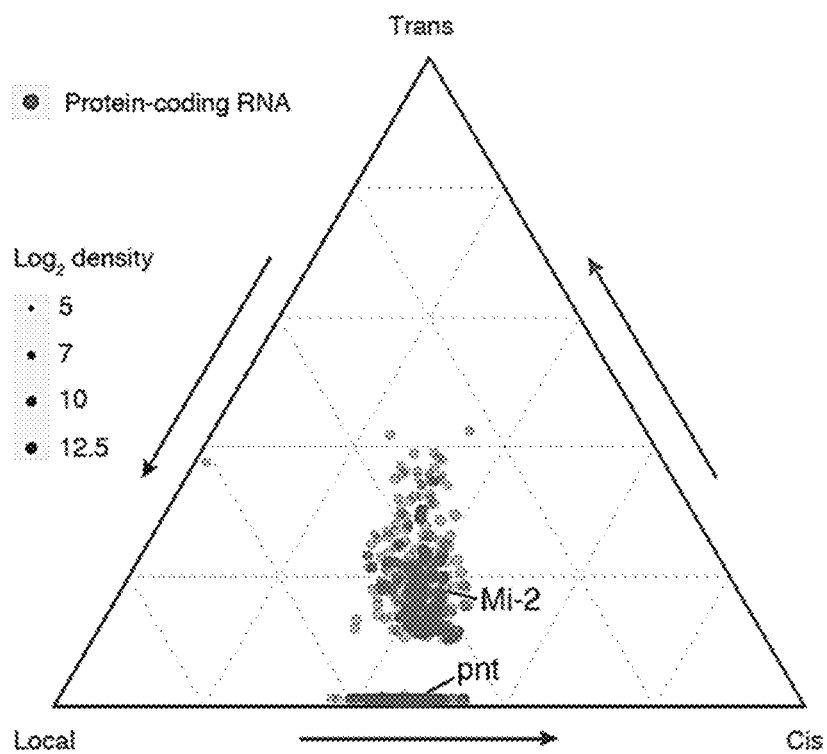
Figure 9D:
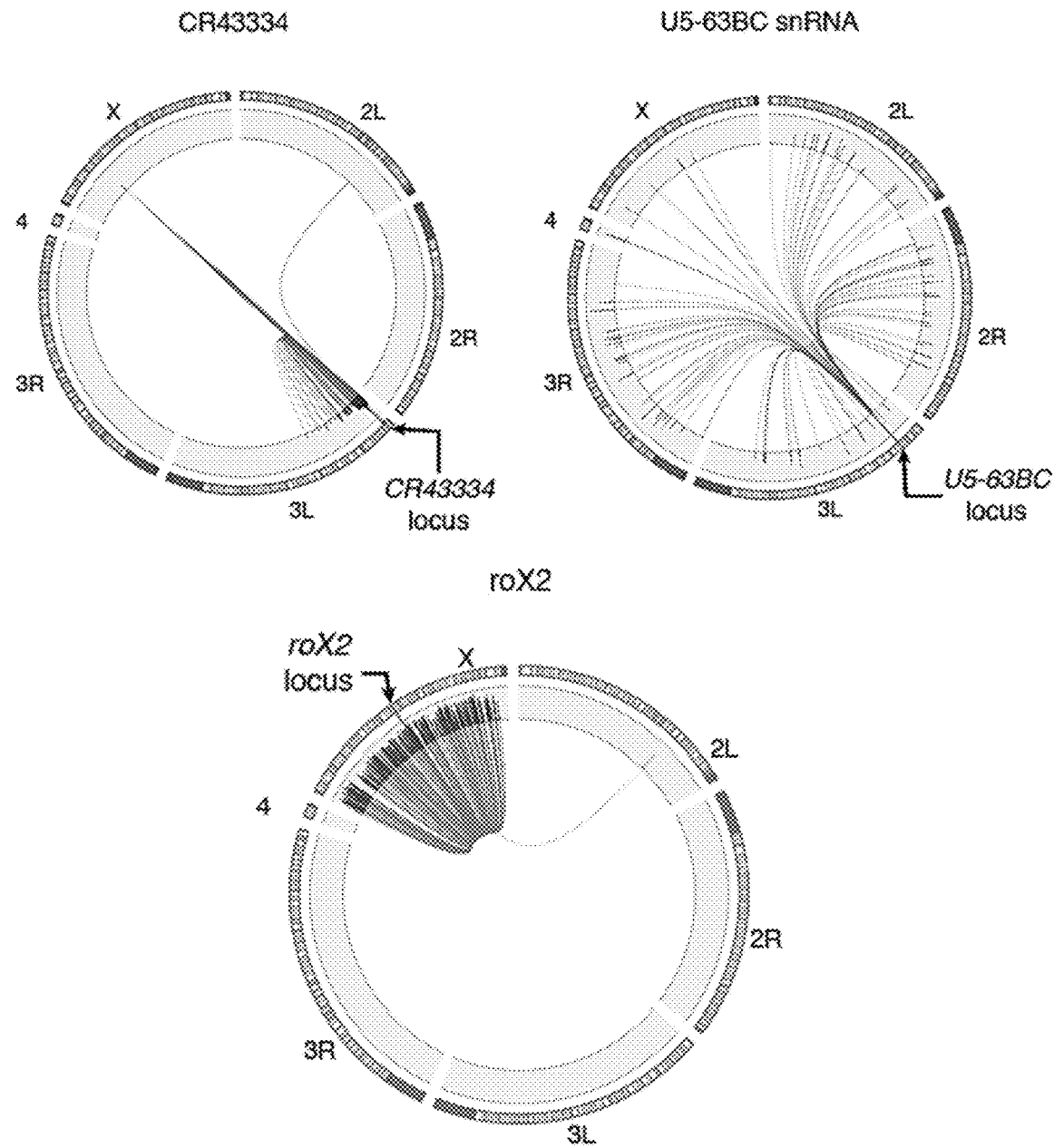
Figure 9E:
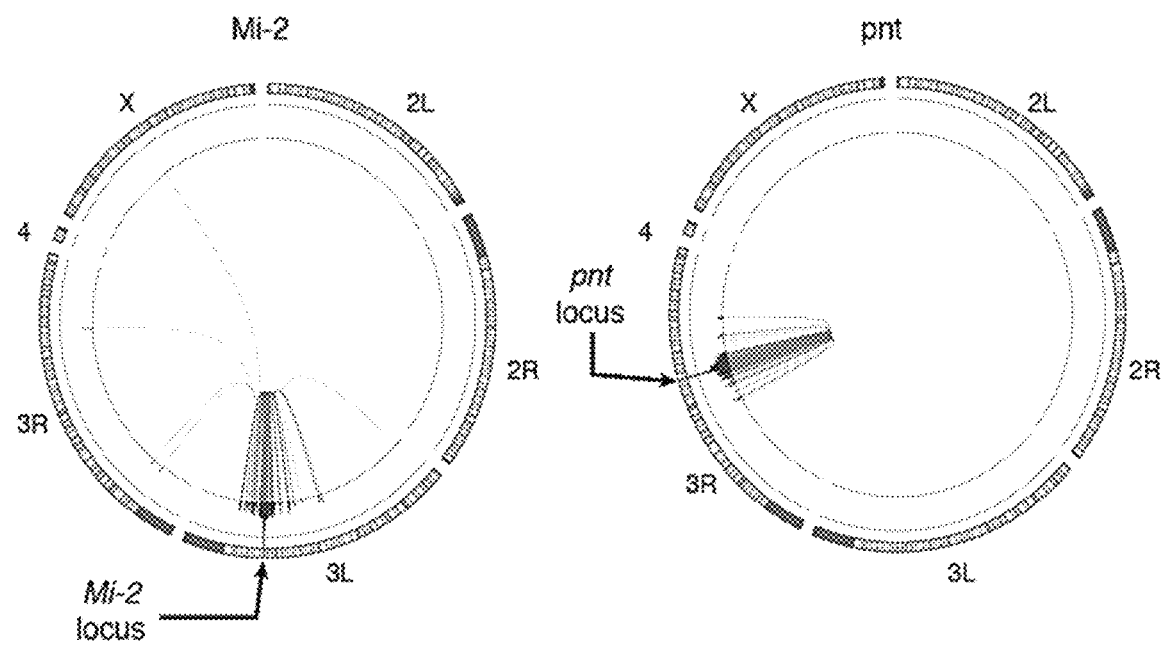

In *Drosophila* S2 cells, a large number of RNAs on chromatin were also detected. An enlarged chromosomal view showed roX2, a lncRNA known to be involved in dosage compensation in *Drosophila*, was found only on Chromosome X (See FIG. 8A). The roX2-chromatin interaction results were compared with the published roX2 ChIRP and ChART data, as well as, the ChIP-seq data on MSL3, a known roX2-interacting factor. Among all mapping results on Chromosome X, it was observed that there was a high degree of similarity (See FIGS. 8B and C). These data unambiguously demonstrate the ability of unbiased GRID-seq to capture known specific RNA-chromatin interactions, thus empowering discovery and characterization of new RNA-chromatin interactions.

Figure 5C:
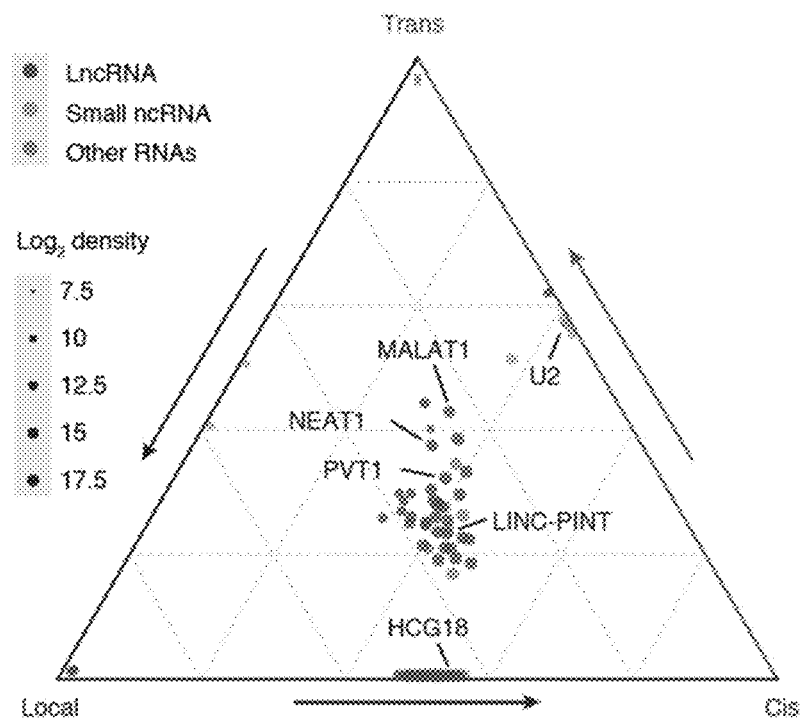
Figure 5D:
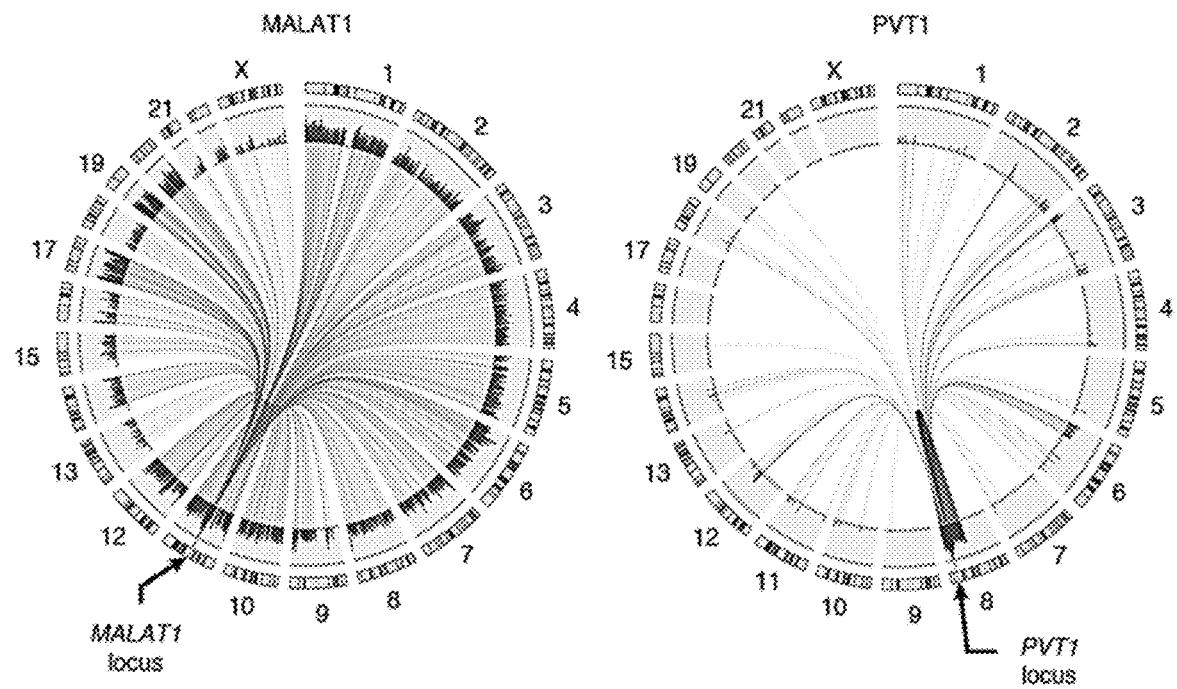

RNA-chromatin interaction ranges. Some RNAs appeared to interact within confined regions of chromatin, while others showed broader chromatin interactions within the same chromosomes, as well as, exhibited specific interactions across chromosomes. Hit RNAs were then characterized based on their chromatin-interacting ranges in local (±10 Kb from their genes), cis (beyond local regions) or trans (across chromosomes). We first analyzed the behaviors of lncRNAs, observing that the majority of lncRNAs had all three modes of chromatin interactions with a few exceptions (see FIG. 5C). A set of lncRNAs, as exemplified by HCG18, were rarely engaged in trans-chromosomal actions, while U2 snRNA showed no local action, likely because it interacts with chromatin during co-transcriptional splicing only after being assembled into small nuclear ribonucleoprotein particle (snRNP). Circos plots further illustrated the ability of MALAT1 to interact with chromatin in all three modes and with similar efficiency, while PVT1 was predominantly engaged in local and cis-chromosomal interactions (see FIG. 5D).

Figure 5E:
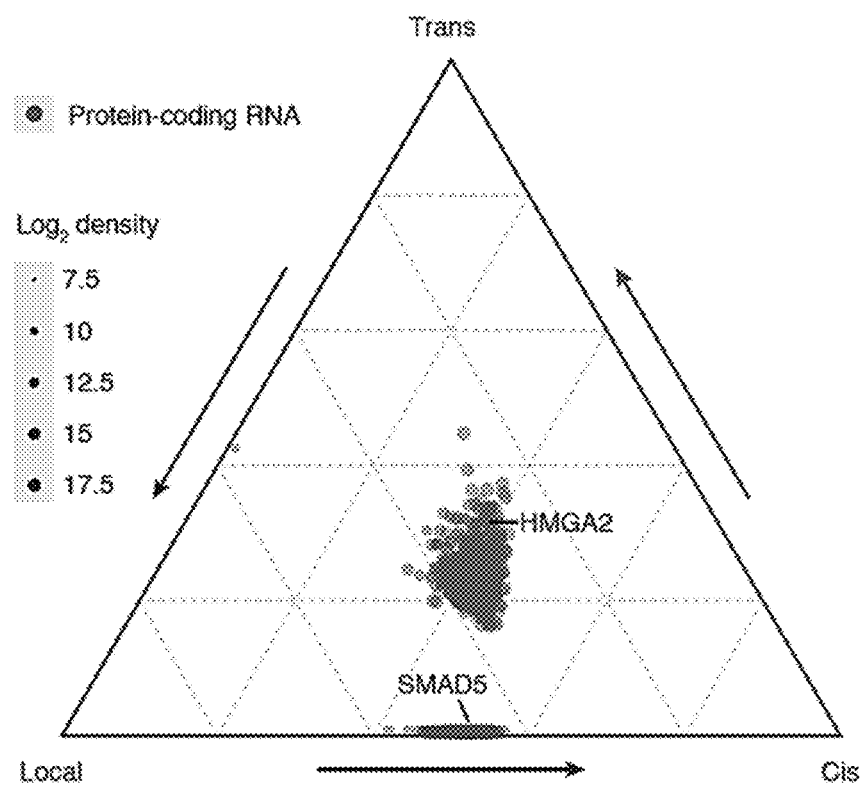
Figure 5F:
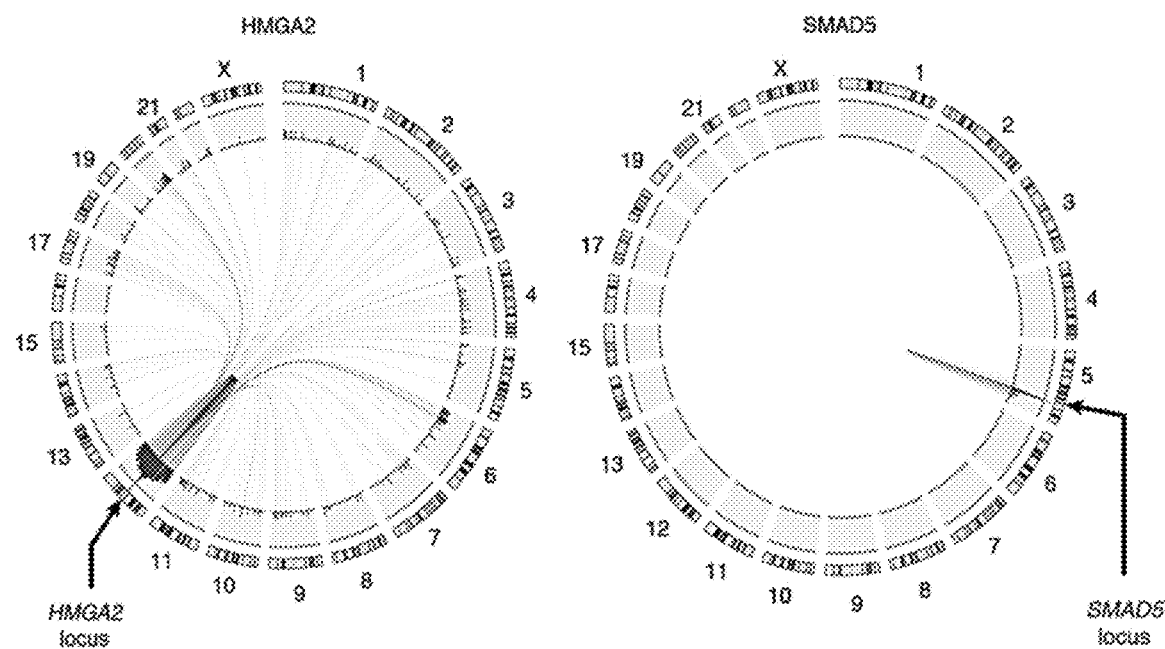

Interestingly, when the same analysis was applied to chromatin-interacting pre-mRNAs, the majority of them were able to participate in all three modes of interactions, but without any exclusively acting in trans (see FIG. 5E). Circos plots again showed HMGA2 pre-mRNA interacted with chromatin in all three modes, although with much reduced frequencies in trans-chromosomal interactions, while SMAD5 pre-mRNA interactions with chromatin were largely confined in local and cis-chromosomal interactions (see FIG. 5F). These findings suggest that many pre-mRNAs behave like lncRNAs in the nucleus. Additionally, while *Drosophila* S2 cells showed the same trend as human cells, a much larger number of small RNAs, predominantly snoRNAs, were involved in chromatin interactions in all three modes (See FIG. 9, and Table 4).

Figure 10A:
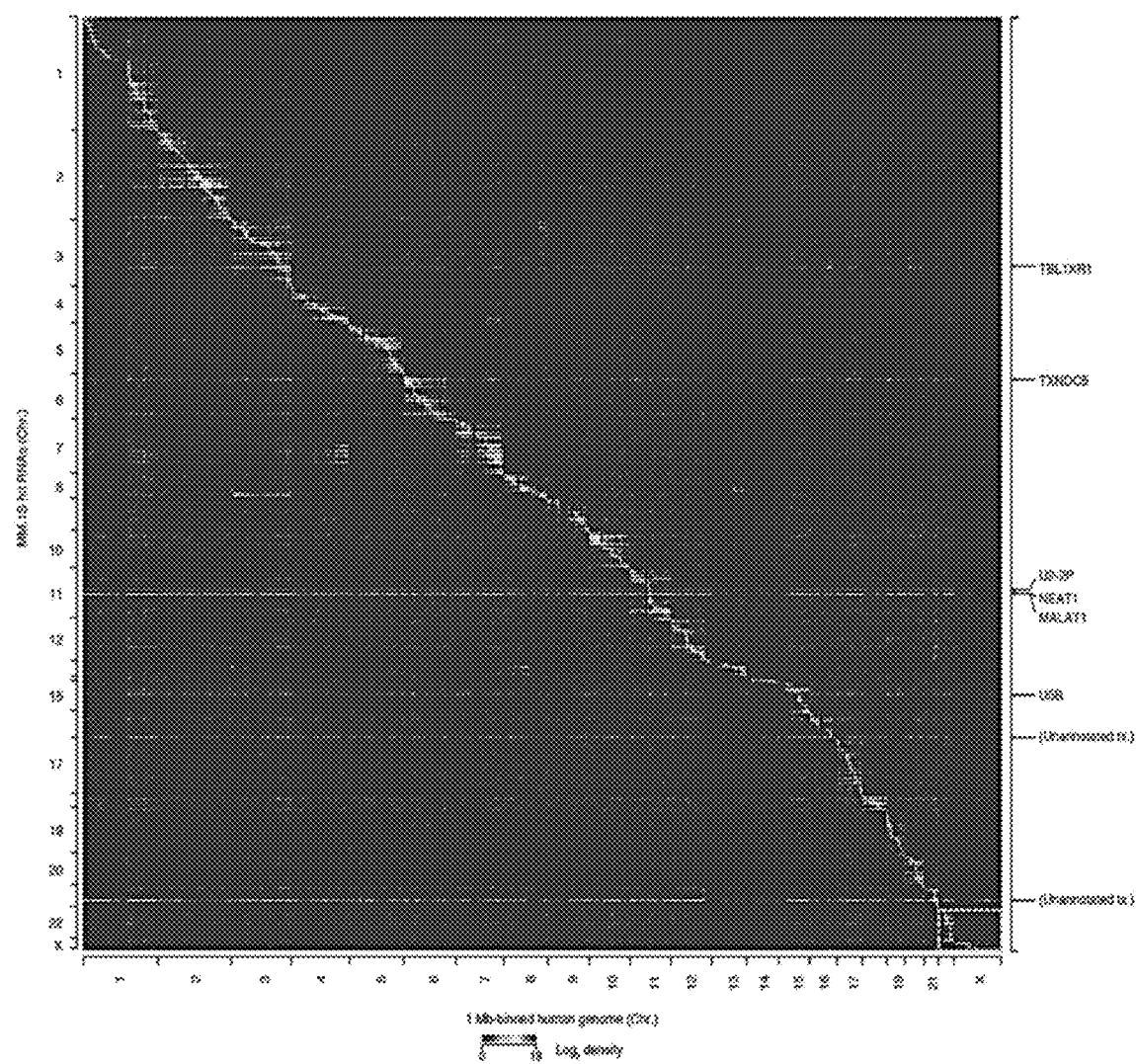
FIG. 10A-B presents a global view of RNA-chromatin interactions in human MM.1S cells. (A) A heatmap showing the chromatin interactions of all hit RNAs across the whole human genome in MM.1S cells. Row: hit RNAs from their origins of transcription. Column: hit RNAs linked to DNA in the 1 Mb-binned human genome. Labeled on the right are representative transchromosomal interacting RNAs. (B) Enlarged heatmaps of boxed Chromosome 22 and X in (A), showing detailed chromatin interactions of hit RNAs from Chromosome 22 (left) and Chromosome X (right). Representative hit RNAs are labeled on the left (pc: protein-coding RNAs, nc: non-coding RNAs), showing that the hit non-coding RNA XIST interacts predominantly with Chromosome X (note that XIST is expressed in MM.1S cells, but not in MDA-MD-231 cells). Top: The background deduced from endogenous trans-chromosomal chromatin-interacting RNAs from all protein-coding genes.
Figure 10B:
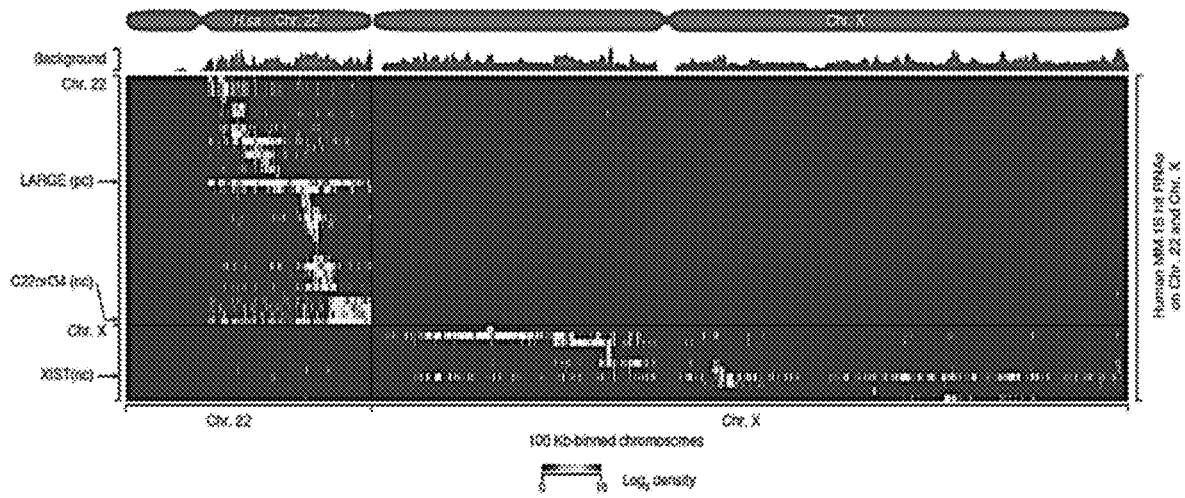
Figure 11A:
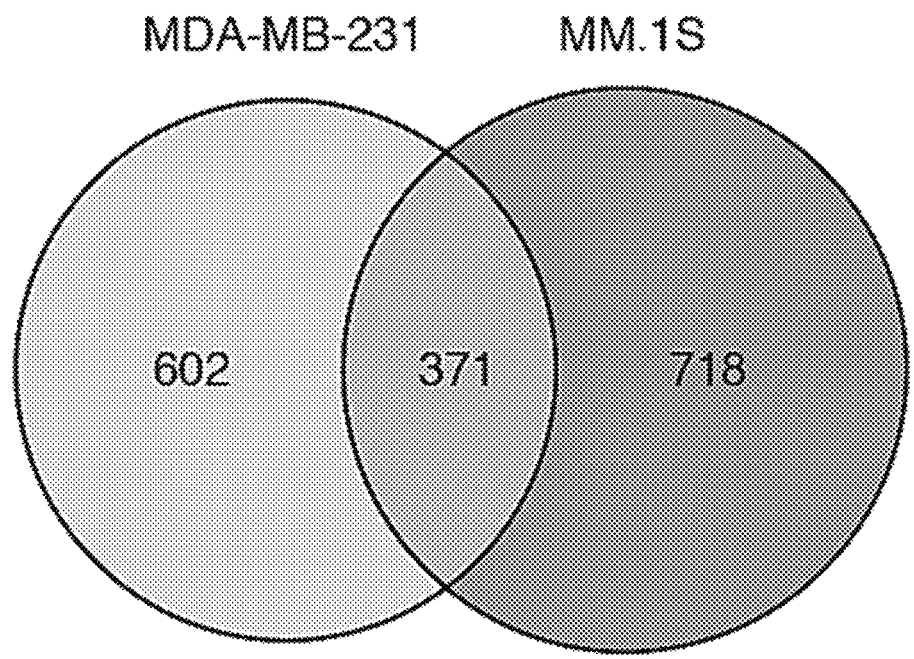
FIG. 11A-H presents cell type-specific RNA-chromatin interactions in mammalian cells. (A) A Venn diagram showing numbers of cell type-specific and common hit RNAs between MDA-MB-231 and MM.1S cells. (B) Comparison of individual GRID-seq RNA reads between the two cell types. Smoothed scatter plot (grey) represents non-hit RNAs and colored dots represent hit RNAs, a few of which are highlighted. (C) Comparison of hit RNAs and their chromatin interactions on Chromosome 4 between MDA-MB-231 and MM.1S cells. Two representative cell type-specific regions are shaded and shown with further details in panels (F) and (G). (D) A heatmap illustrating differential chromatin interactions of common hit RNAs between the two cell types on Chromosome 6. Lines indicate lower and higher levels of chromatin interactions in MDA-MB-231 cells relative to MM.1S cells. (E) Top: Meta-analysis demonstrating enrichment of hit RNAs on enhancers in MDA-MB-231 and MM.1S cells. Bottom: heatmaps of enhancers ranked by normalized GRID-seq RNA signals in the two cell types, showing both cell type-specific and common RNA-chromatin interactions on enhancers. (F), (G), and (H) examples showing broad chromatin interactions of hit RNAs from LEF1 (MM.1S cell specific), VEGFC (MDA-MB-231 cell-specific) and FAM49B (common) in comparison with mapped enhancers and promoters. Light grey overlay behind individual RNA binding tracks (dark grey) represents combined signals from all hit RNAs in the regions. RPM: RNA reads per million. Note that the commonly expressed hit RNAs from FAM49B showed distinct chromatin interactions between the two cell types. Also note different genomic and chromatin-interaction scales in different panels.
Figure 11B:
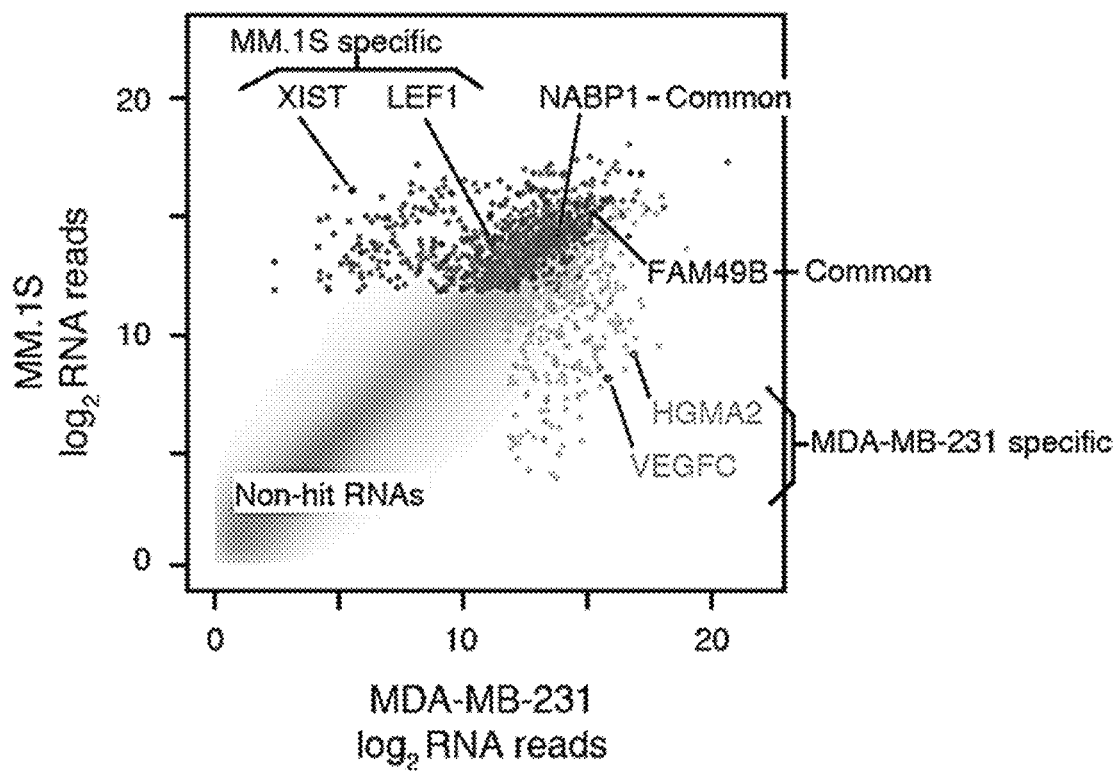
Figure 11C:
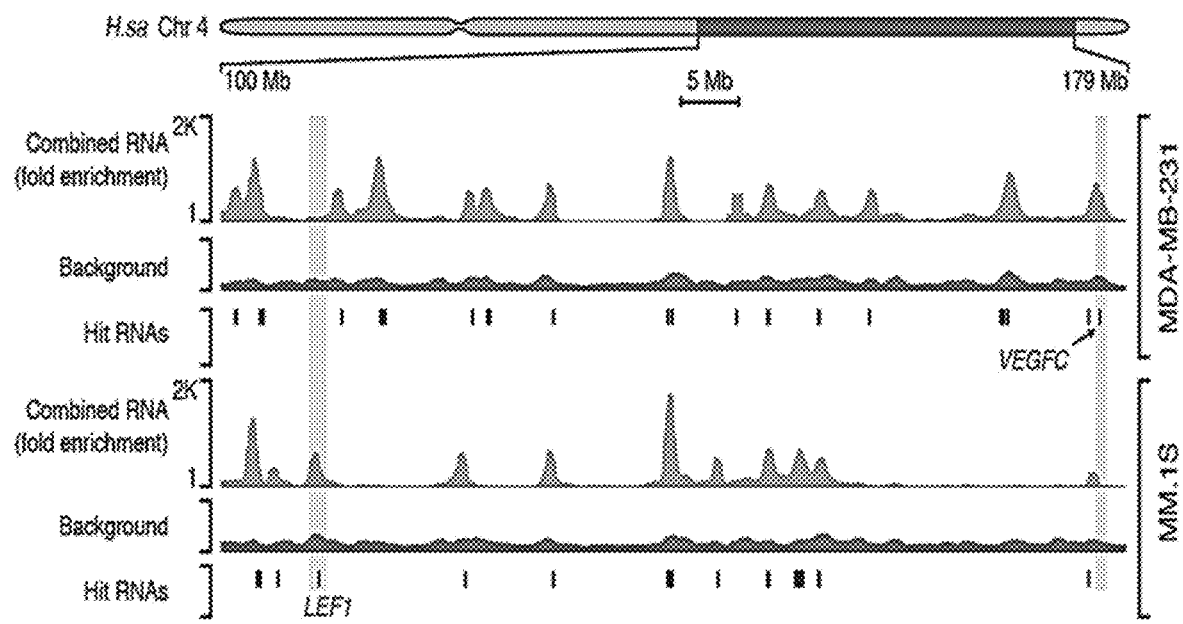
Figure 11D:
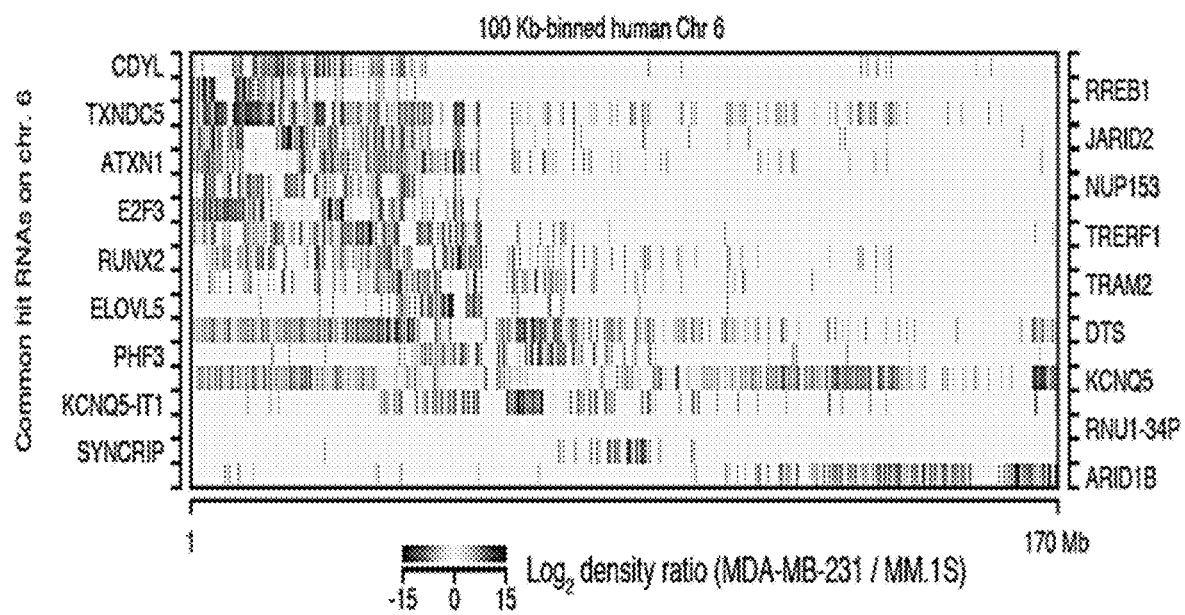
Figure 11E:
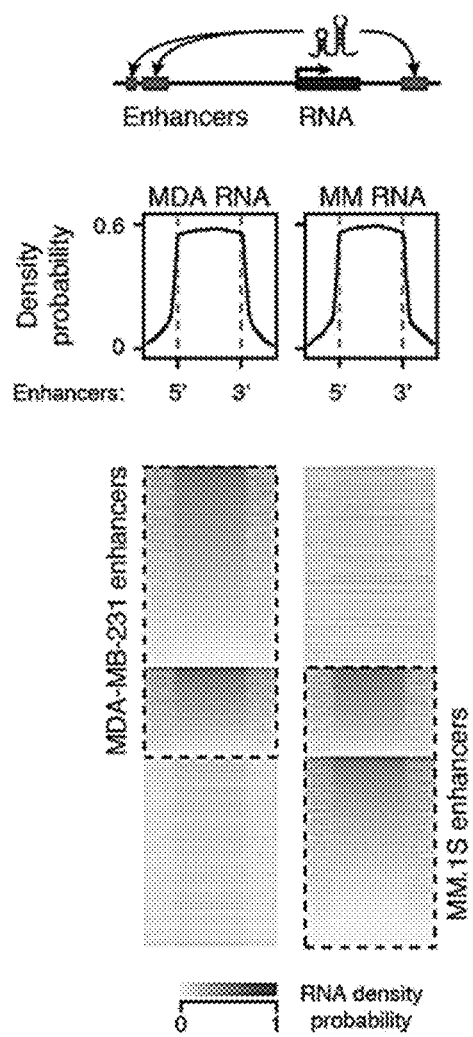
Figure 11F:
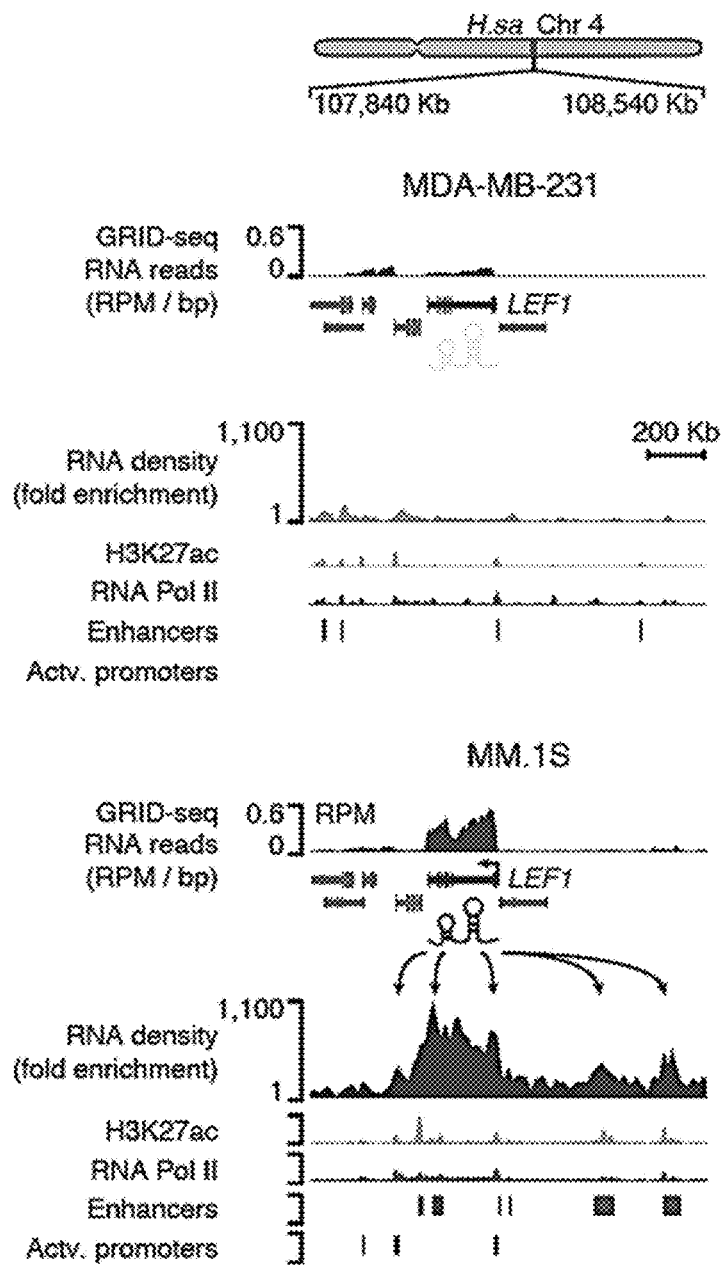
Figure 11G:
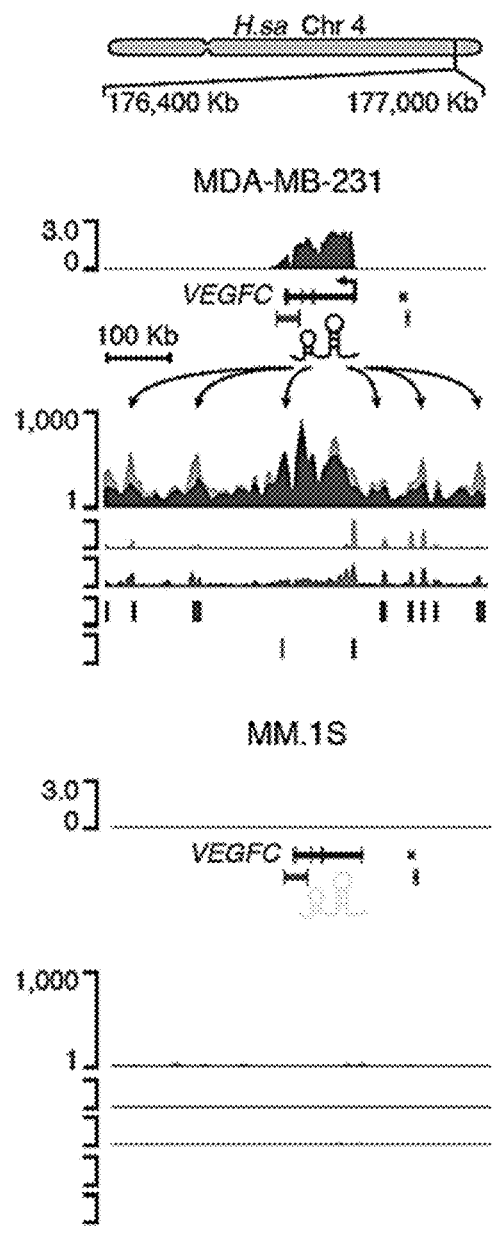
Figure 11H:
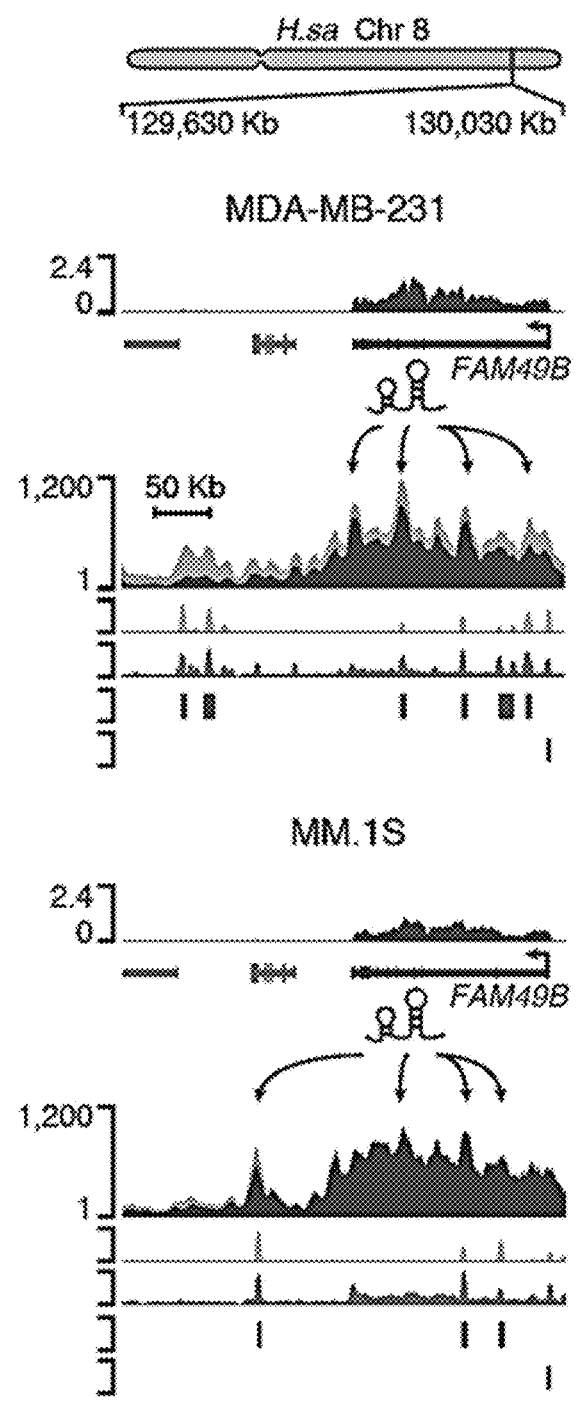
Figure 12A:
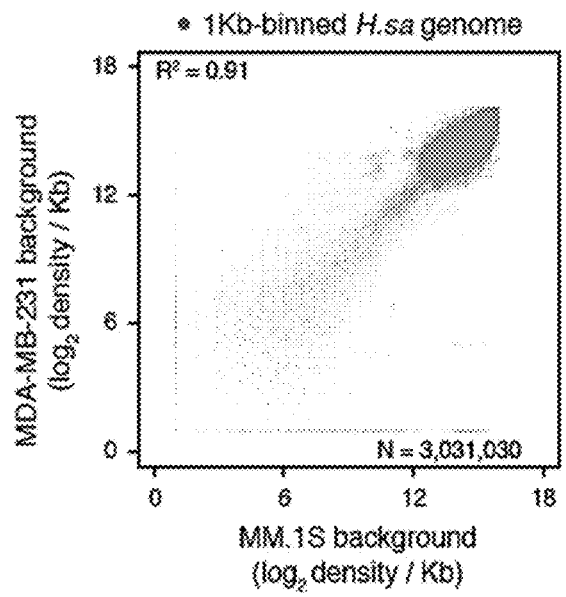
Figure 12B:
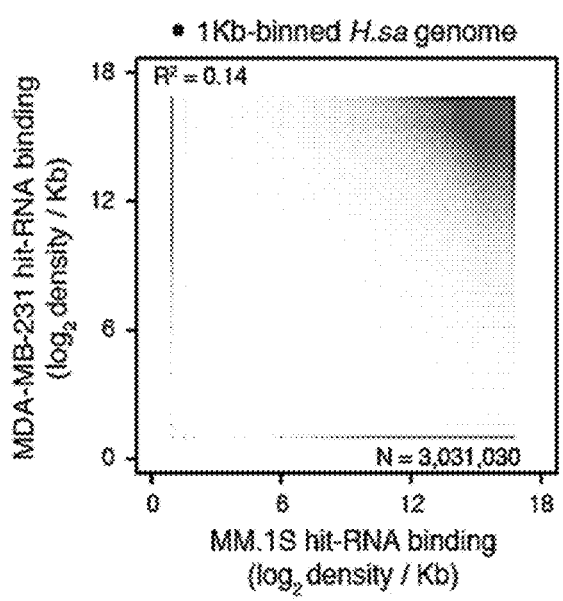
Figure 12C:
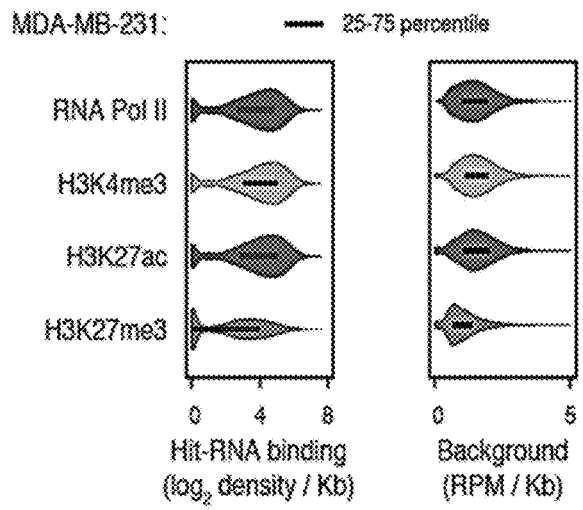
Figure 12D:
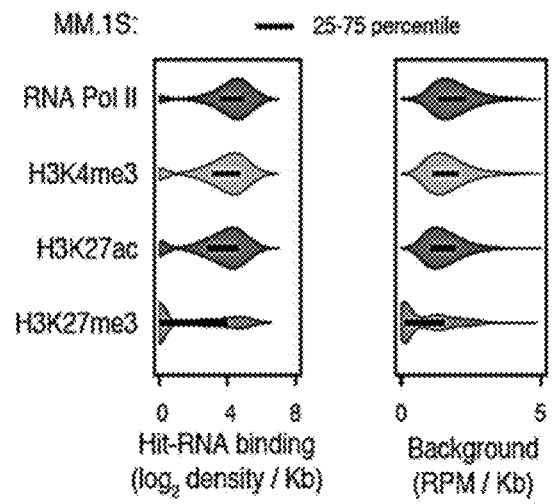

Cell type-specific interactions. Next was determined whether specific RNA-chromatin interactions were reflected in cell type-specific activities in mammals. The GRID-seq analysis was extended to another well-characterized human multiple myeloma cell line MM.1S. As with the MDA-MB-231 cells, a set of trans-acting RNAs were detected, including MALAT1 and NEAT1 (see FIG. 10A). Both coding and non-coding RNAs which broadly interacted with numerous loci near their sites of transcription were also detected. Interestingly, XIST (expressed in MM.1S cells, but not in MDA-MB-231 cells) was detected. XIST was extensively found with Chromosome X (see FIG. 10B), further demonstrating the power and accuracy of GRID-seq in identifying specific RNA-chromatin interactions. Interestingly, cross analysis between MDA-MD-231 and MM.1S cells revealed cell type-specific RNA-chromatin interactions (see FIGS. 11A and B), as exemplified by different RNA signals on Chromosome 4 (see FIG. 11C) and by differential binding of a selective set of hit RNAs on Chromosome 6 (see FIG. 11D). In contrast, background RNA-chromatin interactions were similar between MDA-MB-231 and MM.1S cells (See FIGS. 12 A and B). The results are reminiscent of enhancers, the majority of which are cell type and tissue-specific, as shown previously based on H3K4me1/2 and H3K27ac. Indeed, we noted that nearly all chromatin-interacting RNAs were linked to both shared and cell type-specific enhancers (see FIG. 11E, and FIGS. 12C and D) and in a quantitative fashion (see FIGS. 12E and F) in both MDA-MB-231 and MM.1S cells. This can be directly visualized on specific examples, showing not only cell type-specific interactions of RNAs with their own genes but also with nearby enhancers (see FIGS. 11F and G). Surprisingly, even though the same RNA was detected in both cells, the RNA bound to distinct enhancers (see FIG. 11H), suggesting cell type-specific rewiring of transcription program. Although there was not sufficient read density for eRNAs, which are believed to link enhancers to promoters, the data indicated that pre-mRNAs from actively transcribed genes were also associated with their enhancers, perhaps reflecting putative hubs for enhancer-promoter interactions in the nucleus.

Figure 13A:
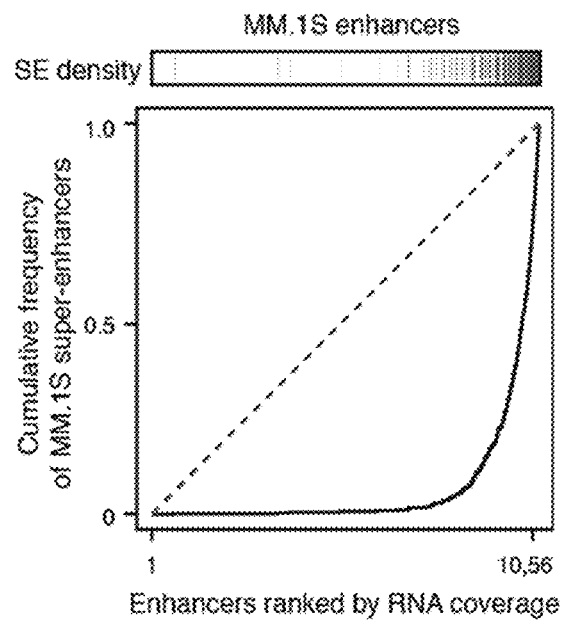
FIG. 13A-E demonstrates the preferential RNA decoration on super-enhancers in MM.1S cells. (A) Super-enhancers in relationship to RNA-chromatin interactions signals detected by GRID-seq. 10,567 mapped enhancers in MM.1S cells (based on the mapped H3K27ac signals in the same cell from GSM894083) are ranked by hit RNA density. Each bar on top represents a superenhancer. Curved line: The cumulative curve of rank-ordered RNA-chromatin interactions; Grey dashed line: Random distribution. (B) Probability density map of hit RNA coverage on superenhancers (SE) versus typical enhancers (TE). (C) Left: Rank-ordered RNA-chromatin interaction levels on all active enhancers. Right: Upper (SE enriched) and lower (TE enriched) 10 percentiles of enhancers selected for functional analysis. (D) Expression of genes associated with top 10% RNA-interacting enhancers (right box) relative to those associated with bottom 10% RNA-interacting enhancers (left box), both within the ±50 Kb range (based on the data from GSM1094100 and GSM1094101). (E) Fold changes in gene expression plotted in the accumulative fashion for the two groups of genes as defined in (C) in response to functional perturbation of enhancers on MM.1S cells by using the BRD4 inhibitor JQ1 (based on the data from GSM1094100, GSM1094101, GSM1094092, and GSM1094093). Statistical significance of comparison is estimated by t-test in panel (B), (D) and (E).
Figure 13B:
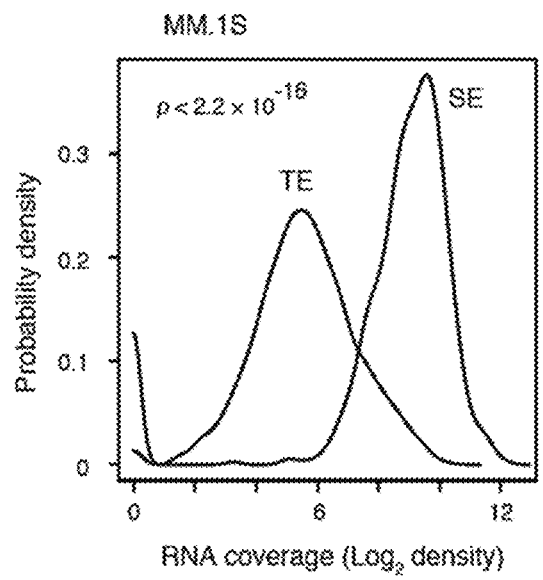

Prevalent RNAs on super-enhancers. Recent studies suggested that enhancers can be segregated into typical and super-enhancers, the latter of which were defined based on much higher density of enhancer marks, such as MED1 and BRD4 ChIP-seq signals, which generally tracked H3K27ac, and importantly, such "stitched" enhancers appeared to be more potent in activating nearby genes. Given most enhancers were associated with GRID-seq signals, it was determined whether such signals could also be used to define the strength of typical versus super-enhancers. By sorting enhancers based on RNA coverage, it was found that enhancers that were decorated with RNAs mostly correspond with super-enhancers in both MDA-MB-231 and MM.1S cells (see FIG. 13A, and FIG. 12G), which was further evidenced by having much higher RNA coverage on super-enhancers relative to typical enhancers in both cell types (see FIG. 13B, and FIG. 12H). Therefore, chromatin-associated RNAs may provide yet another independent measure of enhancer activities.

Figure 13C:
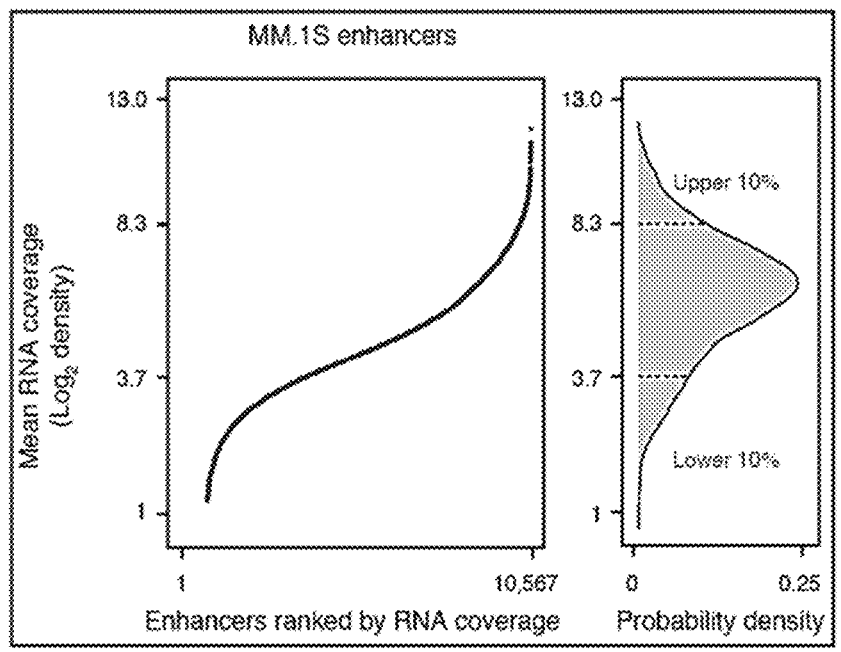
Figure 13D:
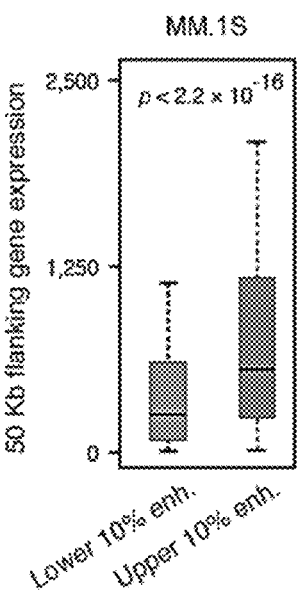
Figure 13E:
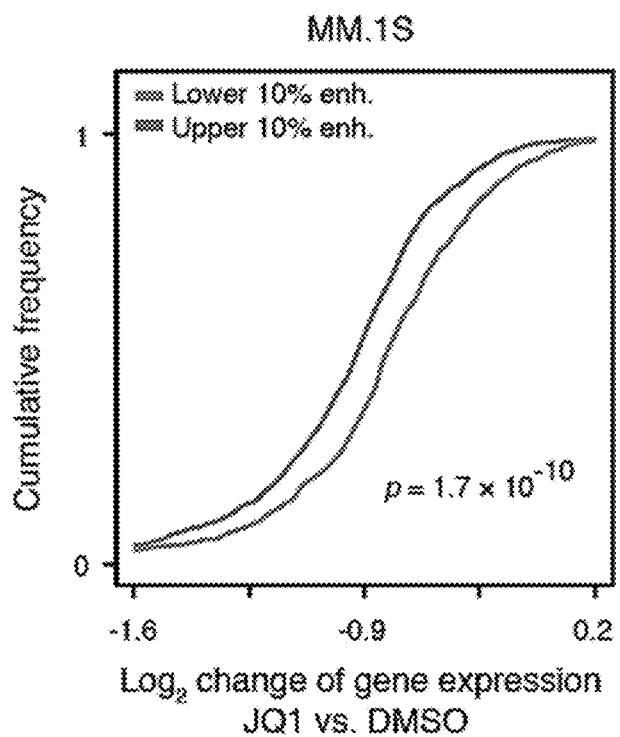

As super-enhancers are more potent than typical enhancers in activating nearby genes in MM.1S cells, the GRID-seq signals were sorted based on RNA coverage and compared with the expression of neighboring genes from 50 Kb flanking enhancers by using the published gene expression data on MM.1S cells. It was found that genes adjacent to top 10% RNA-decorated enhancers were more active than those adjacent to bottom 10% (see FIGS. 13C and D), and similarly, the genes associated with top 10% RNA-decorated enhancers were more responsive to functional perturbation by BRD4 inhibitor JQ1 than those in the bottom 10% (see FIG. 13E). The same set of experiments were performed with MDA-MB-231 cells by using GRO-seq to score nascent RNA production and transcriptional response to JQ1 (see FIGS. 12I, J, and K). The same conclusions were reached. Combined, the data suggest that the levels of chromatin-associated RNAs reflect enhancer activities in activating gene expression, which can be used to differentiate super from typical enhancers.

Figure 14A:
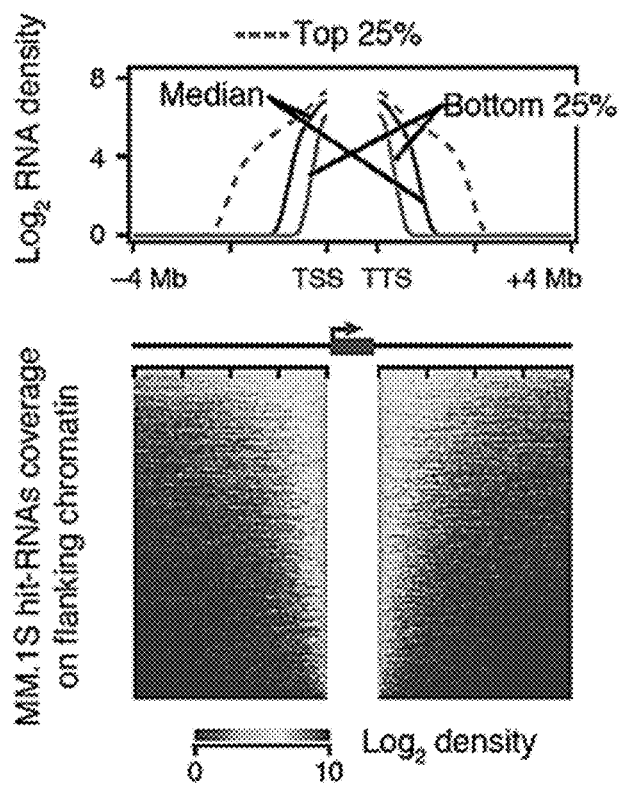
FIG. 14A-G demonstrates inferring enhancer-promoter connectivity by enhancer-associated RNAs. (A) The RNA-chromatin interaction range. Top: Meta-analysis of hit RNAs coverage relative to individual gene bodies. Dashed grey line and black line represent the distributions of top and bottom 25 percentile hit RNAs on chromatin relative to their sites of transcription, respectively. Bottom: A heatmap of hit RNA coverage on both sides of their respective genes loci. (B) A representative intra-chromosomal RNA-chromatin interaction map on Chromosome 1 in MM.1S cells with three potential enhancer-promoter hubs highlighted. (C) The number of genes controlled by typical (right bar) or super-(left bar) enhancers calculated based on inferred enhancer-promoter relationships from network analysis in (B). (D) The number of typical (right bar) and super-(left bar) enhancers involved in controlling a given gene calculated based on inferred enhancer-promoter relationships from network analysis in (B). (E) and (F) Fold changes in gene expression plotted in the accumulative fashion for the genes associated with typical (TE) and super-(SE) enhancers inferred by GRID-seq signals, within the conventional 50 Kb range (E) or without setting any range (F), in response to functional perturbation of enhancers on MM.1S cells by using the BRD4 inhibitor JQ1 (based on the data from GSM1094100, GSM1094101, GSM1094092 and GSM1094093). P-values were determined by Kolmogorov-Smirnov test. (G) Cytoscape visualization of global enhancer-promoter interaction networks inferred by all significant cis- and trans-RNA-chromatin interactions detected by GRID-seq in MM.1S cells.

Inferring enhancer-promoter connectivity. One of the fundamental problems in regulated gene expression is to pair enhancers and promoters. In fact, published ChIA-PET and Hi-C experiments have already indicated that enhancers may reach out to promoters that are far away in terms of linear DNA distance. However, numerous static long-distance DNA-DNA interactions tend to obscure true enhancer-promoter interactions in those experiments, as TADs are largely cell type invariant. Interestingly, as exemplified on MM.1S cells, it was found that RNAs reach out from their sites of transcription to a medium distance of ~1 Mb (see FIG. 14A).

Figure 15A:
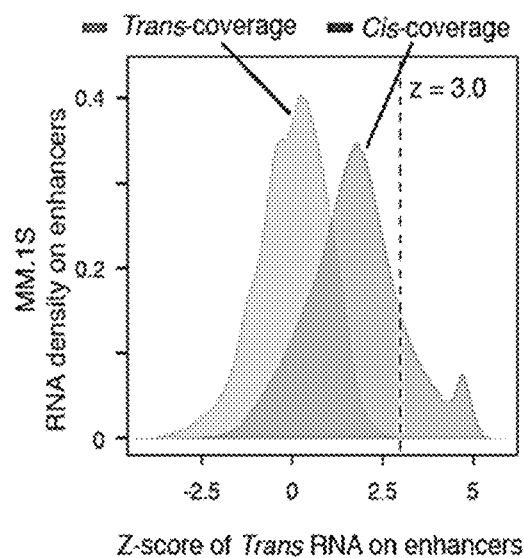
FIG. 15A-F provides inferred enhancer-promoter distance and examples. (A) Densities of hit RNA signals on typical and super-enhancers in MM.1S cells. x-axis: Z-scores of all trans-chromosomal RNA signals (teal). Z 3 was set to define significant RNA coverage on enhancers. (B) Distribution of linear DNA distance between super-enhancers and genes. (C) Distribution of linear DNA distance between typical enhancers and genes. The data indicate similar ranges reached out by typical and super-enhancers. (D) A Circos plot, showing a representative case of two hit RNAs from two genes RRBP1 and SNX5 on nearby seven enhancers, one of which corresponds to a super-enhancer in MM.1S cells. The RRBP1 RNA binding profile is shown on the outer track (green) and the SNX5 RNA binding profile on the inter track (blue). Ribbons connecting with enhancers illustrate inferred enhancer-promoter interactions. (E) and (F) Upon JQ1 treatment, fold changes in gene expression are shown in (E) (based on the data from GSM1094100, GSM1094101, GSM1094092 and GSM1094093) and fold changes in BRD4 binding on individual enhancers in (F) (based on the data from GSM1038271 and GSM1038275).
Figure 15B:
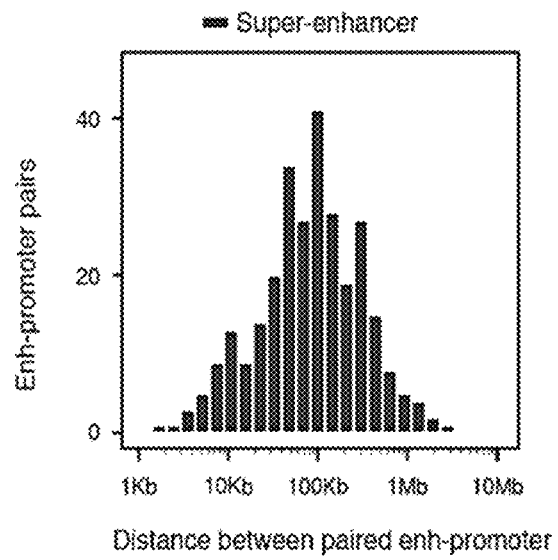
Figure 15C:
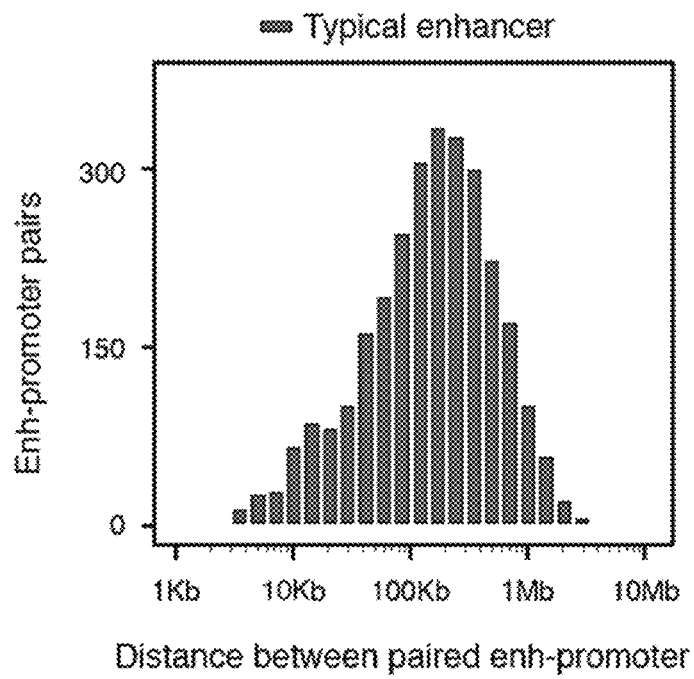

As enhancers tend to attract RNA in general, trans-chromosomal interaction signals of protein-coding RNAs were used to deduce a statistical model for trans-acting RNAs on enhancers. By using a highly stringent criterion of $z \geq 3$, RNA-chromatin interactions that likely reflect the physical proximity between gene loci and enhancers were identified (see FIG. 15A). This analysis clearly suggests that enhancers may reach out to promoters significantly beyond the traditional confinement of 50 Kb. Interestingly, typical and super-enhancers seem to have a similar action range (see FIGS. 15B and C).

Figure 14B:
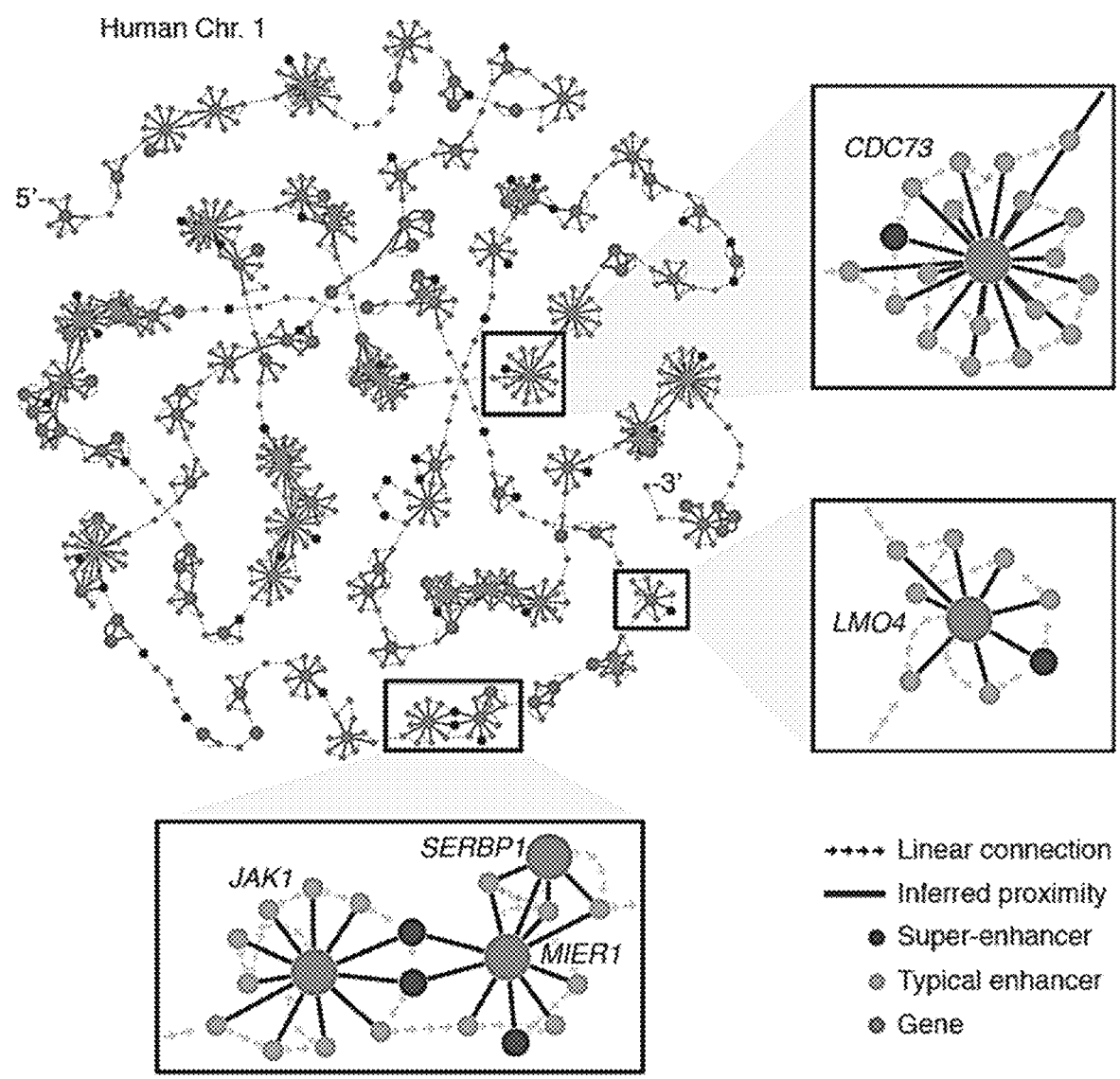
Figure 14:
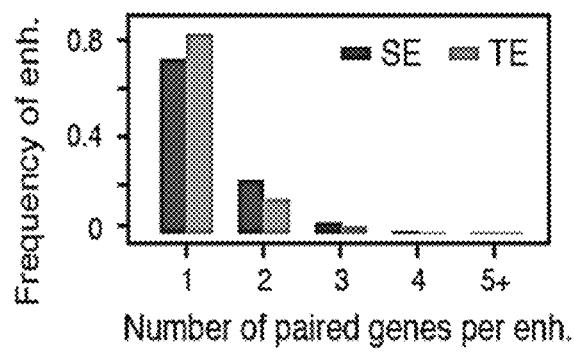
Figure 14D:
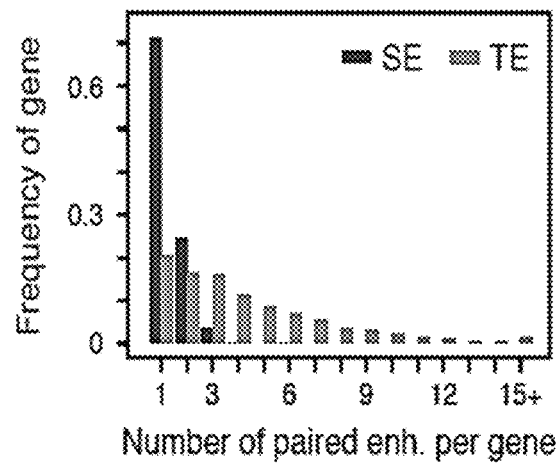

As illustrated on Chromosome 1 and with several enlarged views in MM.1S cells, the GRID-seq defined enhancer-promoter network was visualized with Cytoscape using a self-organized layout (see FIG. 14B, and Table 5). Based on this network, it was found that each enhancer, whether typical or super, seemed to control 1 or 2 genes in most cases (see FIG. 14C). In contrast, each gene seemed to be regulated by multiple typical enhancers, but a given gene is only associated with 1 or 2 super-enhancers (see FIG. 14D). Because these observations may be interpreted as indicating that super-enhancers comprise many individual enhancers stitched together, the findings at least suggest that super enhancers do not control more genes than typical enhancers.

Figure 14E:
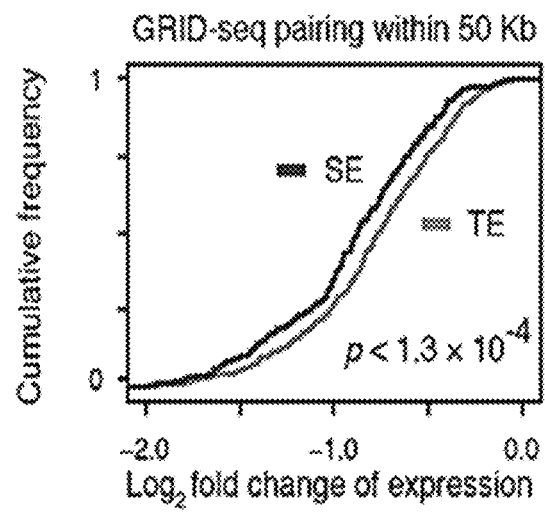
Figure 14F:
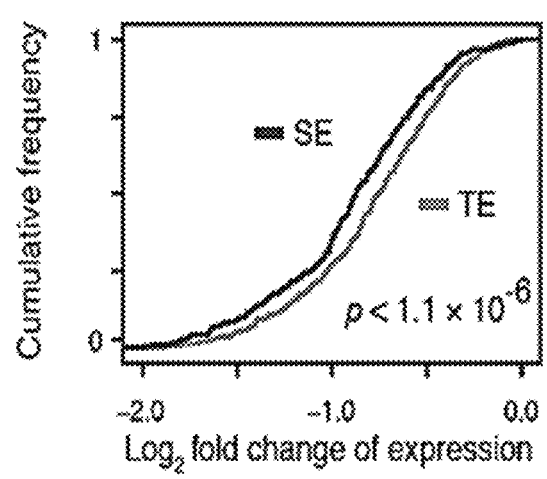
Figure 15D:
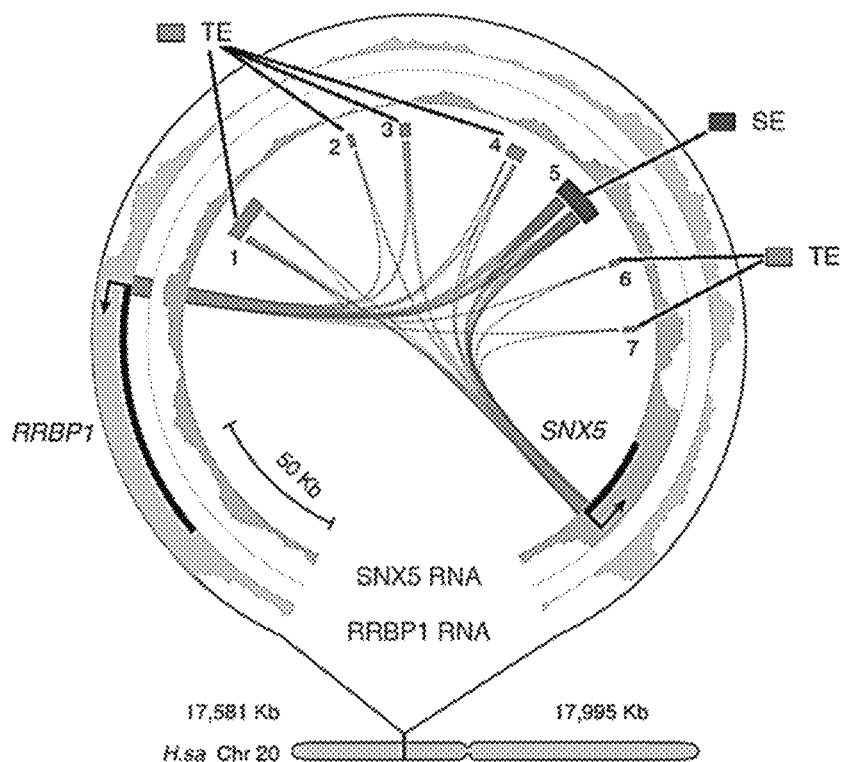
Figure 15E:
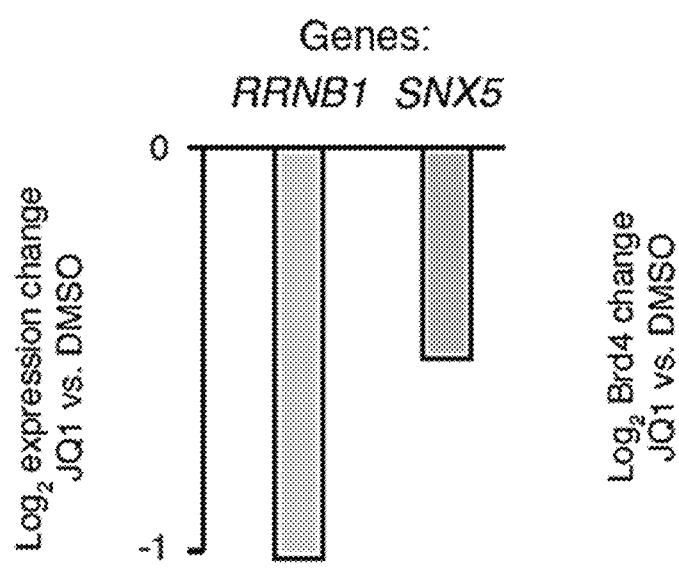
Figure 15F:
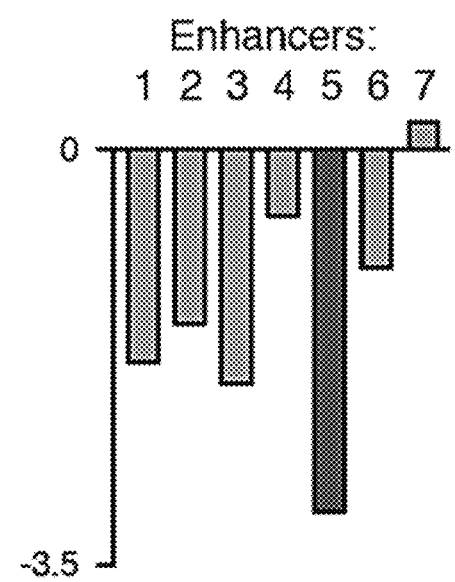

Functional evidence for connectivity. The chromatin-interacting RNAs enabled the estimation of long-distance enhancer-promoter connectivity significantly beyond the traditional framework. Next was determined whether there was any functional evidence for newly predicated enhancer-promoter partnerships. For example, in MM.1S cells, RNAs from two transcribing genes (SNX5 and RPBP1) were interacting with one super-enhancer and six typical enhancers (see FIG. 15D). In response to JQ1 treatment, both genes were down regulated (see FIG. 15E) and the super-enhancer showed more reduced BRD4 binding than all other typical enhancers (see FIG. 15F). Next the analysis was extended to all RNA connected enhancers and promoters in MM.1S cells, asking whether genes associated with at least one super-enhancers (plus typical enhancers) might be more sensitive to perturbation of enhancer activities by JQ1 than those only linked to typical enhancers. It was found that genes associated with at least one super-enhancer were indeed more responsive to JQ1 treatment than those only linked to typical enhancers based on GRID-seq signals within the traditional 50 Kb range (see FIG. 14E). More importantly, the same observation was made based on the connectivity without setting any action range (see FIG. 14F). These data suggest that chromatin-interacting RNAs may indeed be used to deduce long-distance enhancer-promoter interactions and that super-enhancers are superior in activating both local and distal genes.

Figure 14G:
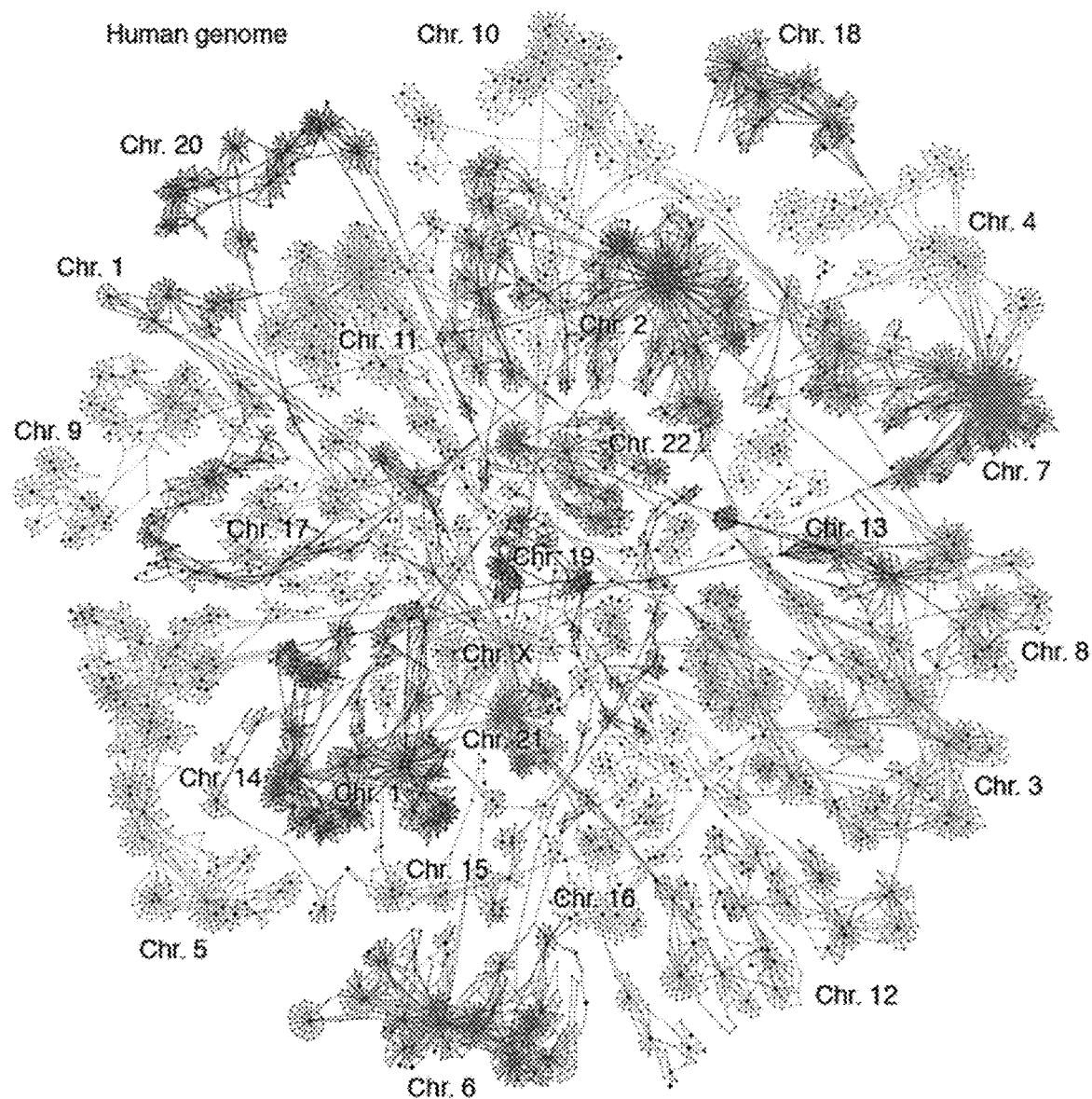

The analysis has been focused on cis-chromosomal interactions, but numerous RNAs were still able to reach out to loci in other chromosomes with sufficient interactions based on the trans-action model, implying the formation of enhancer-promoter hubs even between chromosomes in 3D genome. To visualize such interactions, the network of all deduced enhancer-promoter interactions in MM.1S cells was displayed with Cytoscape by using a self-organized layout. Strikingly, the resulting global network revealed that individual chromosome tended to cluster into multiple intra-chromosomal hubs, each centered by gene(s) expressing chromatin-associated RNAs, many of which were also connected with other chromosomes (see FIG. 14G). These findings suggest that chromatin-interacting RNAs may be used to construct a functional 3D map that resembles the chromosomal organization in the nucleus.

As shown herein, the majority of specific chromatin-interacting RNAs are associated with enhancers marked by H3K4me1/2 and H3K27ac. Recent studies suggest that a subset of enhancers may be considered super-enhancers because of their clustered distribution in mammalian genomes. Interestingly, about half of all chromatin-interacting RNAs detected by GRID-seq in two mammalian cell types are decorated on those super-enhancers, which provide an independent measure for enhancer activities. Based on functional perturbation of enhancer activities, previous studies also indicate that super-enhancers appear to be more potent than typical enhancers in enhancing gene expression and more sensitive to inhibition of BRD4. The GRID-seq signals confirmed the previous conclusions and further revealed that super-enhancers are similar to typical enhancers in action range.

Chromatin-interacting RNAs and enhancer-promoter connectivity. It has been inferred that there is enhancer-promoter connectivity based upon long-distance DNA-DNA interaction data, especially those enriched with important transcription factors, such as RNA Pol II, or indirectly deduced based on enhancer-promoter units (EPUs) based on their co-regulation patterns in different tissues. Functional studies also validated some of those inferred relationships in various biological contexts. Importantly, the data presented herein facilitates the study of global enhancer-promoter connectivity without the constraint of the traditional boundary of ~50 Kb, which is in fact in line with examples based on physical DNA-DNA interactions. It is envisioned that such "long-distance" interactions are actually quite local in the 3D space of the nucleus, and therefore, enhancers, particularly super-enhancers, may share hubs with gene promoters they regulate.

While chromatin-interacting RNAs can be used to detect various gene activities, those RNAs may actually play more active roles in nucleating enhancer-promoter hubs. Furthermore, while many of those chromatin-interacting RNAs are well-characterized lncRNAs, the majority are actually pre-mRNAs transcribed from typical protein-coding genes. Thus, the data presented herein implies that many pre-mRNAs may function as lncRNAs in the nucleus. In fact, increasing evidence suggests the functional importance of nascent RNAs from both pre-mRNAs and lncRNAs in mediating a range of regulatory activities on chromatin, as exemplified by the recruitment of a de novo DNA methyltransferase, transcriptional activators, or repressors. The GRID-seq technology described herein is expected to expedite the discovery of a variety of RNA-mediated regulatory activities on chromatin.

A number of embodiments have been described herein. Nevertheless, it will be understood that various modifications may be made without departing from the spirit and scope of this disclosure. Accordingly, other embodiments are within the scope of the following claims.

What is claimed is:

1. A method for global mapping and visualizing RNA-chromatin interactome sequencing reads to a reference genome, comprising:
   (1) ligating in situ a bivalent linker to endogenous RNA crosslinked with genomic DNA and protein of an isolated fixed nuclei to form a bivalent linker-RNA-protein complex, wherein the bivalent linker comprises a region of single-stranded RNA (ssRNA) and a region of double-stranded DNA (dsDNA),
   wherein the region of dsDNA of the bivalent linker comprises: (i) a top strand comprising a 5' phosphorylated DNA sequence, and (ii) a bottom strand comprising a region of RNA, a region of DNA, one or more recognition sites for restriction enzymes, and one or more capture moieties, and wherein the region of RNA of the bivalent linker is at the 5' end of the bottom strand, is pre-adenylated and comprises one or more bar code sequences, such that the ssRNA region of the bivalent linker is ligated to endogenous RNAs in the fixed isolated nuclei forming a ligated ssRNA-RNA region;

(2) extending the bivalent linker with a reverse transcriptase into the ligated ssRNA-RNA region;

(3) ligating in situ the dsDNA region of the bivalent linker to genomic DNA of the bivalent linker-RNA-DNA-protein complex to form a ligated dsDNA-DNA region, such that the bivalent linker that is ligated to endogenous RNA of the RNA-DNA-protein complex is also ligated to genomic DNA of the RNA-DNA-protein complex, such that ligation affords a ligated-bivalent linker-RNA-DNA-protein-complex comprising a looped structure;

(4) treating the isolated fixed nuclei comprising ligated-bivalent linker-RNA-DNA-protein-complex comprising a looped structure of step (6) with Proteinase K to afford a dsDNA-capture probe comprising total DNA;

(5) purifying the dsDNA-capture probe by affinity purification using a capture agent that is bound to a solid support that binds with the one or more capture moieties;

(6) denaturing the dsDNA-capture probe to form two single-stranded DNA (ssDNA) products, wherein one ssDNA product remains bound to the capture agent while the other ssDNA product is released into solution;

(7) converting the ssDNA product that is released into solution into a dsDNA product by second strand synthesis using a polymerase;

(8) cutting the dsDNA product using restriction enzymes that recognize the one or more recognition sites of the bivalent linker to form restriction fragment products having different sizes;

(9) purifying and resolving the dsDNA restriction fragment products by gel electrophoresis, then isolating a restriction fragment product band having the highest molecular weight to provide isolated restriction fragment products, wherein the double stranded dsDNA restriction fragment products comprises segments obtained from the isolated nucleic including RNA-related segments and a genomic DNA-related segments;

(10) attaching an adapter to the isolated restriction fragment products;

(11) deep sequencing the isolated restriction fragment products to generate raw sequencing reads;

(12) sorting the raw sequencing reads using the one or more barcode sequences to form library of sequencing reads;

(13) aligning the library of sequencing reads to a reference genome; and

(14) mapping and visualizing the binding locations of the library of sequence reads on the reference genome to provide the global mapping and visualizing of RNA-chromatin interactome, wherein steps (1) to (14) are performed in the order as listed.

2. The method of claim 1, further comprising before step (1):
(A) stabilizing RNAs on chromatin by fixing cells with one or more fixative agents to crosslink RNA, DNA and proteins in chromatin;
(B) isolating nuclei from the fixed cells to provide isolated fixed nuclei; and
(C) digesting DNA in situ in the isolated fixed nuclei with one or more restriction enzymes.

3. The method of claim 2, wherein the one or more fixative agents is selected from the group consisting of disuccinimidyl glutarate, formaldehyde, glutaraldehyde, acrolein, glyoxal, carbodiimides, osmium tetroxide, mercuric chloride, ethanol, ethanol, methanol, and acetone.

4. The method of claim 2, wherein the cells are doubly fixed with formaldehyde and disuccinimidyl glutarate.

5. The method of claim 2, wherein the genomic DNA is digested with one or more restriction enzymes selected from the group consisting of AciI, AluI, BfaI, BfuCI, BstUI, CviAII, CviKI-1, CviQI, DpnI, DpnII, FatI, HaeIII, HhaI, HinP1I, HpaII, HpyCH4IV, HpyCH4V, LpnPI, MboI, MluCI, MnlI, MseI, MspI, MspJI, NlaIII, PhoI, RsaI, Sau3AI, Taqα1, Tsp509I, AccII, AfaI, AluBI, AoxI, AspLEI, BscFI, Bsh1236I, BshFI, BshI, BsiSI, BsnI, Bsp143I, BspACI, BspANI, BspFNI, BssMI, BstENII, BstFNI, BstHHI, BstKTI, BstMBI, BsuRI, CfoI, Csp6I, CviJI, CviRI, CviTI, FaeI, FaiI, FnuDII, FspBI, GlaI, HapII, Hin1II, R9529, Hin6I, HpySE526I, Hsp92II, HspAI, Kzo9I, MaeI, MaeII, MaII, MvnI, NdeII, PalI, RsaNI, SaqAI, SetI, SgeI, SgrTI, Sse9I, SsiI, Sth132I, TaiI, TaqI, TasI, ThaI, TruII, Tru9I, TscI, TspEI, TthHB8I, and XspI.

6. The method of claim 5, wherein the one or more restriction enzymes is AluI.

7. The method of claim 1, wherein the bottom strand comprises a DNA nucleotide that is conjugated to a capture moiety.

8. The method of claim 7, wherein the capture moiety is a biotin residue and the capture agent bound to a solid support is streptavidin beads.

9. The method of claim 1, wherein the one or more bar code sequences is from 3 to 8 base pairs in length.

10. The method of claim 1, wherein the dsDNA capture probe is denatured by adding a denaturant.

11. The method of claim 10, where the denaturant is sodium hydroxide.

12. The method of claim 1, wherein the dsDNA product is cut with a MmeI restriction enzyme.

13. The method of claim 1, wherein the step of purifying and resolving the dsDNA restriction fragment products by gel electrophoresis, are carried out on an agarose gel.

14. The method of claim 2, wherein the cells are human cells.

15. The method of claim 1, wherein the method generates >200 million 100 nucleotide raw sequencing reads.

16. The method of claim 1, wherein the method generates ~40 million uniquely mapped read mates.

17. The method of claim 1, wherein the library of sequencing reads aligned to the reference genome is mapped and visualized using a bioinformatics software program for visualizing molecular interactions.

18. The method of claim 1, wherein the reference genome is a human genome.

* * * * *

SEQUENCE LISTING

```
<160> NUMBER OF SEQ ID NOS: 7

<210> SEQ ID NO 1
<211> LENGTH: 33
<212> TYPE: DNA
<213> ORGANISM: Artificial Sequence
<220> FEATURE:
<223> OTHER INFORMATION: Bivalent linker strand

<400> SEQUENCE: 1
gttggagttc ggtgtgtggg agtgagctgt gtc                             33

<210> SEQ ID NO 2
<211> LENGTH: 45
<212> TYPE: DNA
<213> ORGANISM: Artificial Sequence
<220> FEATURE:
<223> OTHER INFORMATION: Bivalent linker strand
<220> FEATURE:
<221> NAME/KEY: misc_feature
<222> LOCATION: (10)..(12)
<223> OTHER INFORMATION: N is a random nucleotide selected from A, U, G,
      and C

<400> SEQUENCE: 2
guuggauucn nngacacagc tcactcccac acaccgaact ccaac                45

<210> SEQ ID NO 3
```

```
<211> LENGTH: 21
<212> TYPE: DNA
<213> ORGANISM: Artificial Sequence
<220> FEATURE:
<223> OTHER INFORMATION: Adapter oligonucleotide

<400> SEQUENCE: 3
agatcggaag agcacacgtc t                                              21

<210> SEQ ID NO 4
<211> LENGTH: 35
<212> TYPE: DNA
<213> ORGANISM: Artificial Sequence
<220> FEATURE:
<223> OTHER INFORMATION: Adapter oligonucleotide
<220> FEATURE:
<221> NAME/KEY: misc_feature
<222> LOCATION: (34)..(35)
<223> OTHER INFORMATION: N is any nucleotide selected from A, T, G and C

<400> SEQUENCE: 4
acactctttc cctacacgac gctcttccga tctnn                               35

<210> SEQ ID NO 5
<211> LENGTH: 67
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (30)..(34)
<223> OTHER INFORMATION: Is a 5 nucleotide barcode of any nucleotide
      combination

<400> SEQUENCE: 5
aatgatacgg cgaccaccga gatctacacn nnnnacactc tttccctaca cgacgctctt    60
ccgatct                                                              67

<210> SEQ ID NO 6
<211> LENGTH: 41
<212> TYPE: DNA
<213> ORGANISM: Artificial Sequence
<220> FEATURE:
<223> OTHER INFORMATION: Oligonucleotide Primer

<400> SEQUENCE: 6
caagcagaag acggcatacg agacgtgtgc tcttccgatc t                        41

<210> SEQ ID NO 7
<211> LENGTH: 33
<212> TYPE: DNA
<213> ORGANISM: Artificial Sequence
<220> FEATURE:
<223> OTHER INFORMATION: Sequencing Primer

<400> SEQUENCE: 7
acactctttc cctacacgac gctcttccga tct                                 33
```